United States Patent
Kassab et al.

(10) Patent No.: US 8,075,532 B2
(45) Date of Patent: *Dec. 13, 2011

(54) DEVICES, SYSTEMS, AND METHODS FOR PERICARDIAL ACCESS

(75) Inventors: Ghassan S. Kassab, Zionsville, IN (US); Jose A. Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/596,968

(22) PCT Filed: Mar. 12, 2008

(86) PCT No.: PCT/US2008/056666
§ 371 (c)(1), (2), (4) Date: Mar. 10, 2010

(87) PCT Pub. No.: WO2008/134128
PCT Pub. Date: Nov. 6, 2008

(65) Prior Publication Data
US 2010/0160719 A1 Jun. 24, 2010

Related U.S. Application Data

(63) Continuation-in-part of application No. PCT/US2008/053061, filed on Feb. 5, 2008, which is a continuation-in-part of application No. PCT/US2007/015207, filed on Jun. 29, 2007.

(60) Provisional application No. 60/914,452, filed on Apr. 27, 2007, provisional application No. 60/817,421, filed on Jun. 30, 2006.

(51) Int. Cl.
*A61M 5/32* (2006.01)
*A61M 5/178* (2006.01)
*A61M 29/00* (2006.01)

(52) U.S. Cl. ..... 604/176; 604/511; 604/104; 604/164.01

(58) Field of Classification Search ............. 604/103.07, 604/104, 164.01, 164.03, 164.04, 164.08, 604/164.13, 174, 176, 511; 607/120, 122, 607/126, 129, 130
See application file for complete search history.

(56) References Cited

U.S. PATENT DOCUMENTS

| | | |
|---|---|---|
| 3,583,404 A | 6/1971 | McWhorter |
| 3,630,207 A | 12/1971 | Kahn et al. |
| 4,946,457 A | 8/1990 | Elliott |

(Continued)

OTHER PUBLICATIONS

Uchida et al. Angiogenic therapy of acute mycardial infarction by intrapericardial injection of basic fibroblast growth factor and heparin sulfate: An experimental study. 1995.*

(Continued)

*Primary Examiner* — Nicholas D Lucchesi
*Assistant Examiner* — Nathan R Price
(74) *Attorney, Agent, or Firm* — Ice Miller LLP

(57) ABSTRACT

Devices, systems, and methods for accessing tissue, including the internal and external tissues of the heart, are disclosed. At least some of the embodiments disclosed herein provide access to the external surface of the heart through the pericardial space for localized delivery of leads to the heart tissue. At least some of the embodiments disclosed herein provide access to the pericardial space for removal of accumulated fluid. In addition, various disclosed embodiments provide devices, systems, and methods for engaging a tissue, for removing fluid from a space within a body, and for the delivery of substances to a targeted site for therapeutic purposes.

41 Claims, 30 Drawing Sheets

U.S. PATENT DOCUMENTS

| | | | |
|---|---|---|---|
| 5,195,968 | A | 3/1993 | Lundquist et al. |
| 5,292,332 | A | 3/1994 | Lee |
| 5,715,817 | A | 2/1998 | Stevens-Wright et al. |
| 6,113,611 | A | 9/2000 | Allen et al. |
| 6,200,303 | B1 | 3/2001 | Verrior et al. |
| 6,338,345 | B1 | 1/2002 | Johnson et al. |
| 6,500,167 | B1 | 12/2002 | Webster, Jr. |
| 6,595,982 | B2 | 7/2003 | Sekino et al. |
| 6,613,062 | B1 | 9/2003 | Leckrone et al. |
| 6,626,930 | B1 | 9/2003 | Allen et al. |
| 6,663,633 | B1 | 12/2003 | Pierson, III |
| 6,692,458 | B2 | 2/2004 | Forman et al. |
| 6,776,784 | B2 | 8/2004 | Ginn |
| 6,837,893 | B2 | 1/2005 | Miller |
| 6,918,890 | B2 * | 7/2005 | Schmidt ............... 604/164.01 |
| 6,991,616 | B2 | 1/2006 | Bencini et al. |
| 7,029,468 | B2 | 4/2006 | Honebrink |
| 7,081,125 | B2 | 7/2006 | Edwards et al. |
| 7,326,231 | B2 | 2/2008 | Phillips et al. |
| 7,842,068 | B2 | 11/2010 | Ginn |
| 7,931,628 | B2 | 4/2011 | Zhu et al. |
| 7,942,897 | B2 | 5/2011 | Lafontaine |
| 2002/0072768 | A1 | 6/2002 | Ginn |
| 2002/0091354 | A1 | 7/2002 | Navia, Sr. |
| 2002/0165561 | A1 | 11/2002 | Ainsworth |
| 2002/0168317 | A1 * | 11/2002 | Daighighian et al. ....... 424/1.11 |
| 2003/0009145 | A1 | 1/2003 | Struijker-Boudier et al. |
| 2003/0109852 | A1 | 6/2003 | Peterson et al. |
| 2003/0225420 | A1 | 12/2003 | Wardle |
| 2004/0010216 | A1 | 1/2004 | Zhu et al. |
| 2004/0018228 | A1 | 1/2004 | Fischell et al. |
| 2004/0087938 | A1 | 5/2004 | Leckrone et al. |
| 2004/0230131 | A1 | 11/2004 | Kassab et al. |
| 2005/0054994 | A1 | 3/2005 | Cioanta et al. |
| 2005/0113760 | A1 * | 5/2005 | Chachques et al. ........... 604/174 |
| 2005/0256450 | A1 * | 11/2005 | Palasis et al. ................... 604/82 |
| 2005/0261673 | A1 | 11/2005 | Bonner |
| 2006/0106442 | A1 | 5/2006 | Richardson et al. |
| 2006/0207612 | A1 | 9/2006 | Jackson et al. |
| 2006/0217764 | A1 | 9/2006 | Abbott et al. |
| 2006/0240113 | A1 | 10/2006 | Hunter et al. |
| 2007/0010708 | A1 | 1/2007 | Ness |
| 2007/0010793 | A1 | 1/2007 | Callas et al. |

OTHER PUBLICATIONS

International Searching Authority, International Search Report, mailed Sep. 11, 2008 (PCT/US07/15207).

International Searching Authority, International Written Opinion, mailed Sep. 11, 2008 (PCT/US07/15207).

Huang, Engineering RGC-Modified Loposomes for Targeted Drug Delivery to Activated Platelets, PhD Thesis, Case Western Reserve University, Aug. 2006.

International Searching Authority, International Search Report, mailed Oct. 1, 2008 (PCT/US08/53061).

International Searching Authority, International Written Opinion, mailed Oct. 1, 2008 (PCT/US08/53061).

International Searching Authority, International Search Report, mailed Aug. 29, 2008 (PCT/US08/56666).

International Searching Authority, International Written Opinion, mailed Aug. 29, 2008 (PCT/US08/56666).

Uchida et al. "Angiogenic therapy of acute myocardial infarction by intrapericardial injection of . . . " American Heart Journal, vol. 130, No. 6, pp. 1182-1188 (Dec. 1995).

* cited by examiner

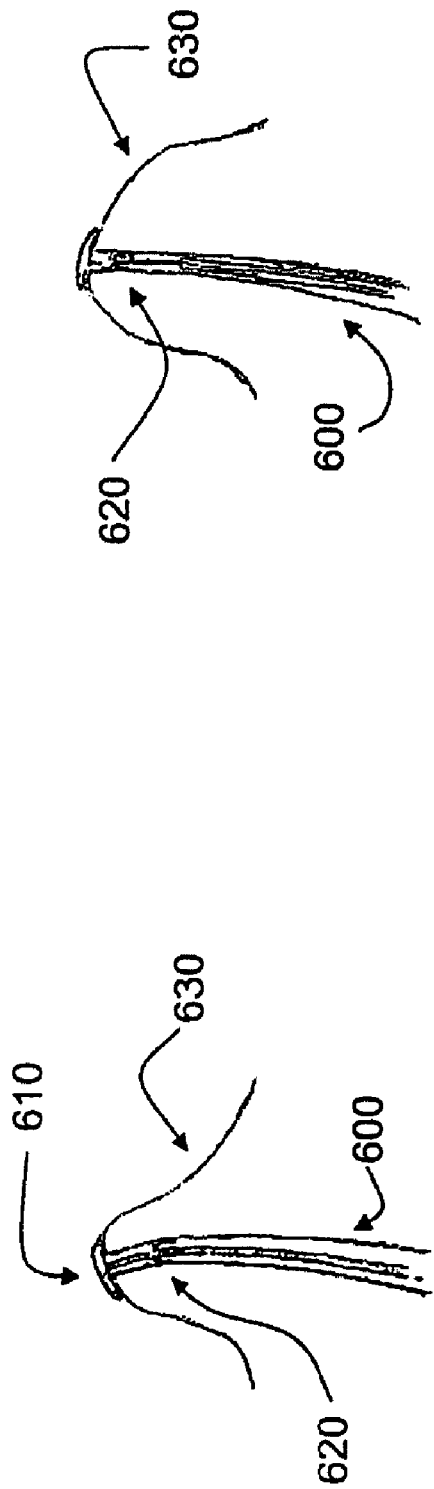
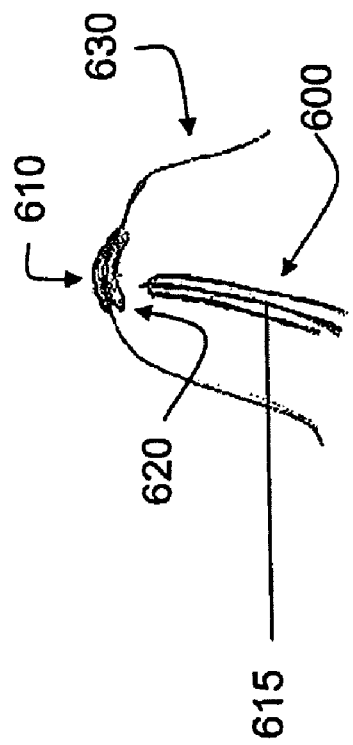
Fig. 4A
Fig. 4B
Fig. 4C

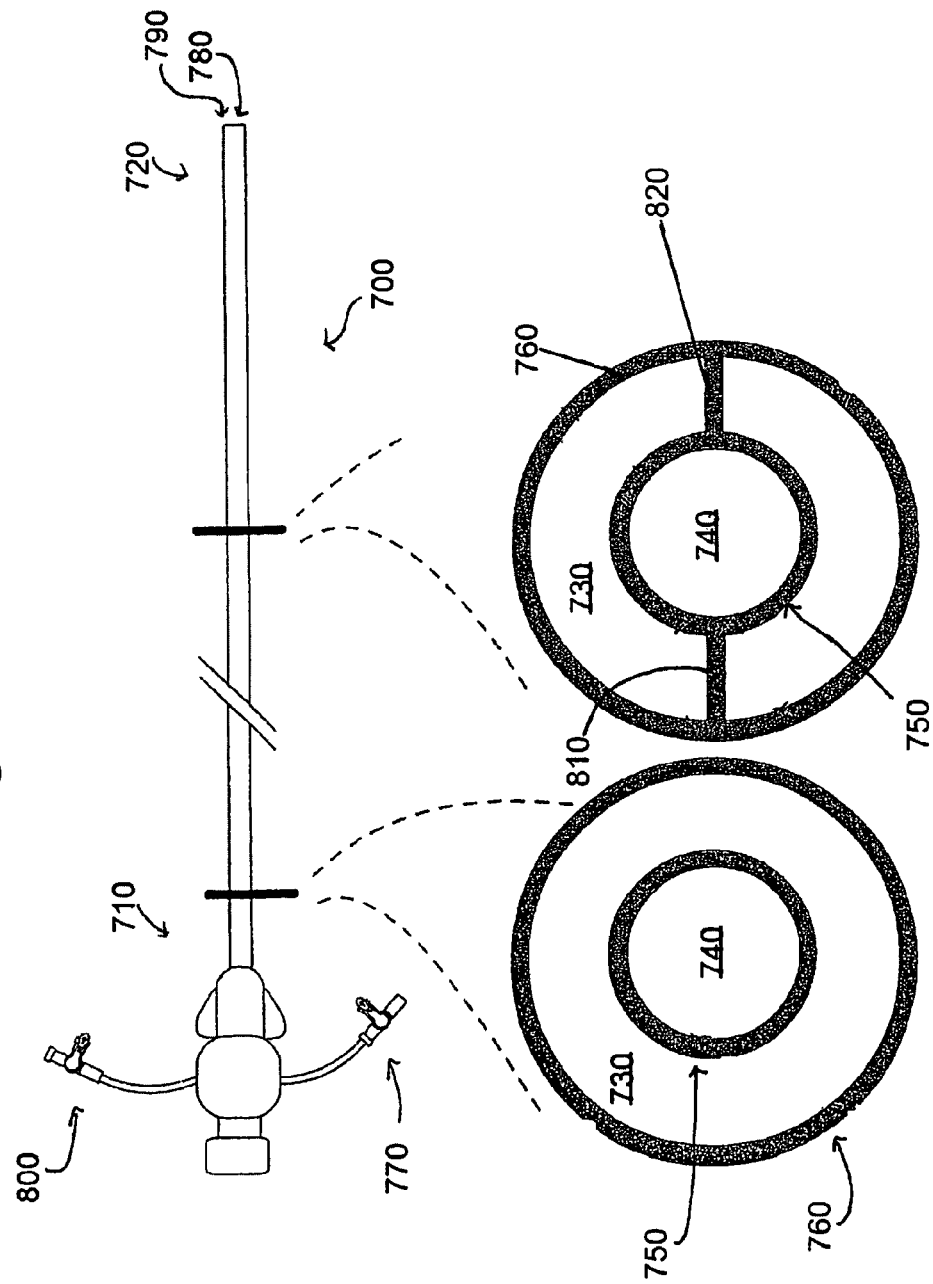

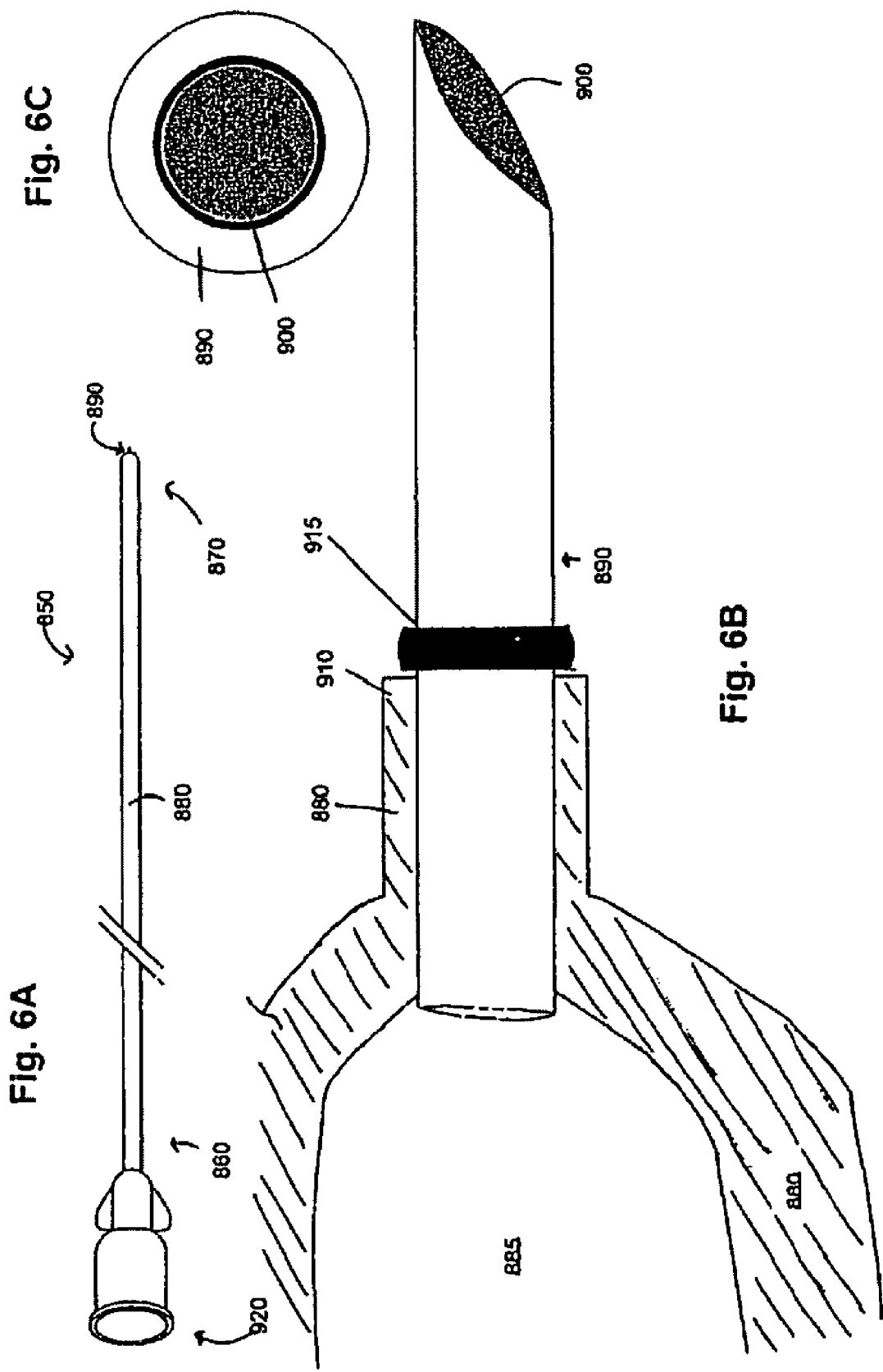

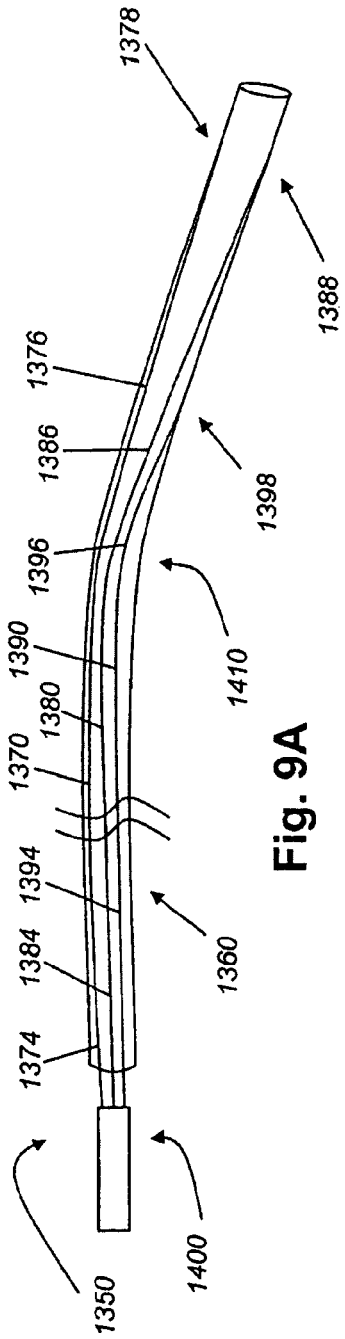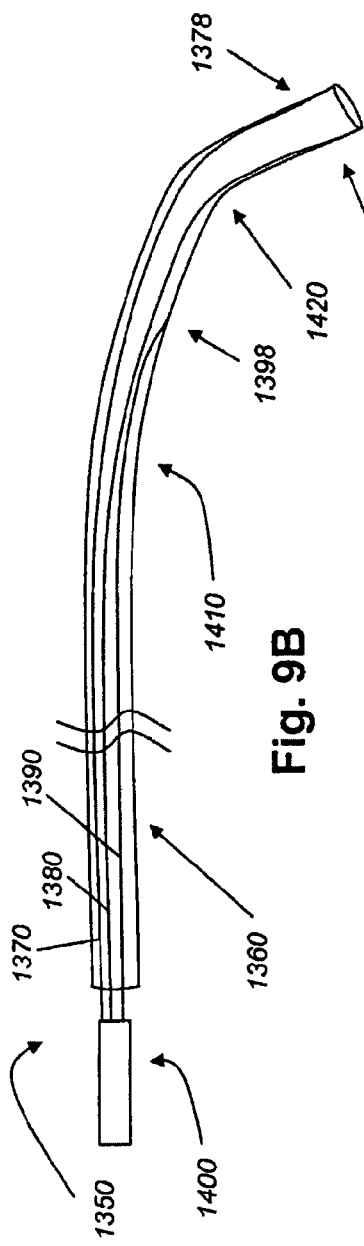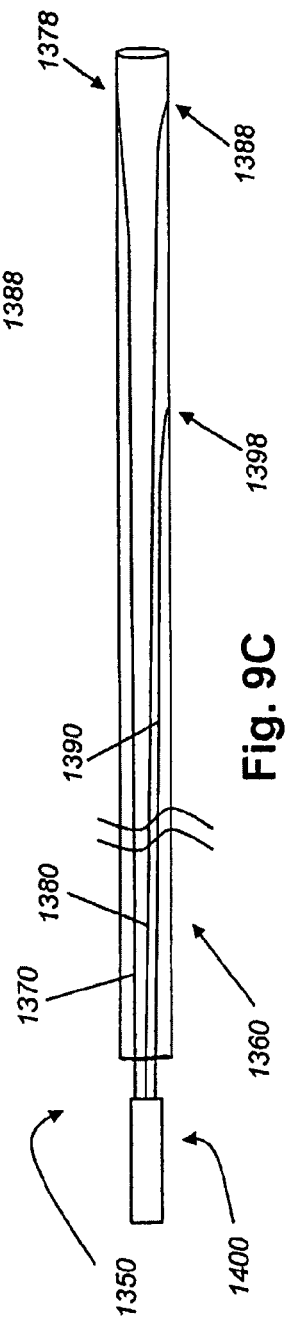

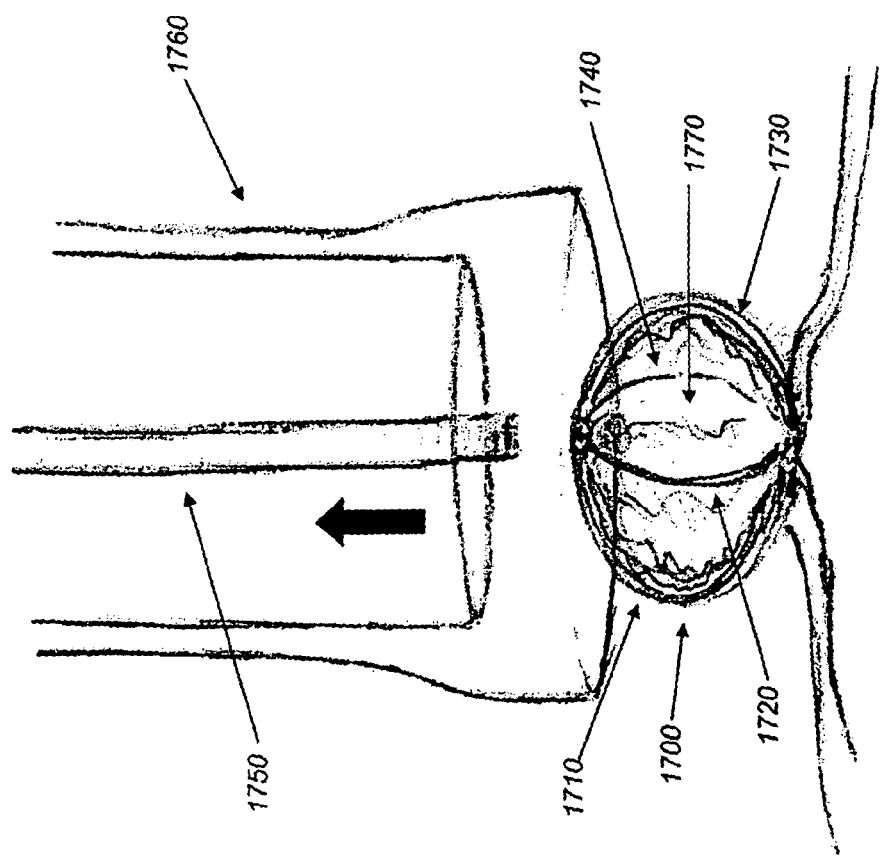

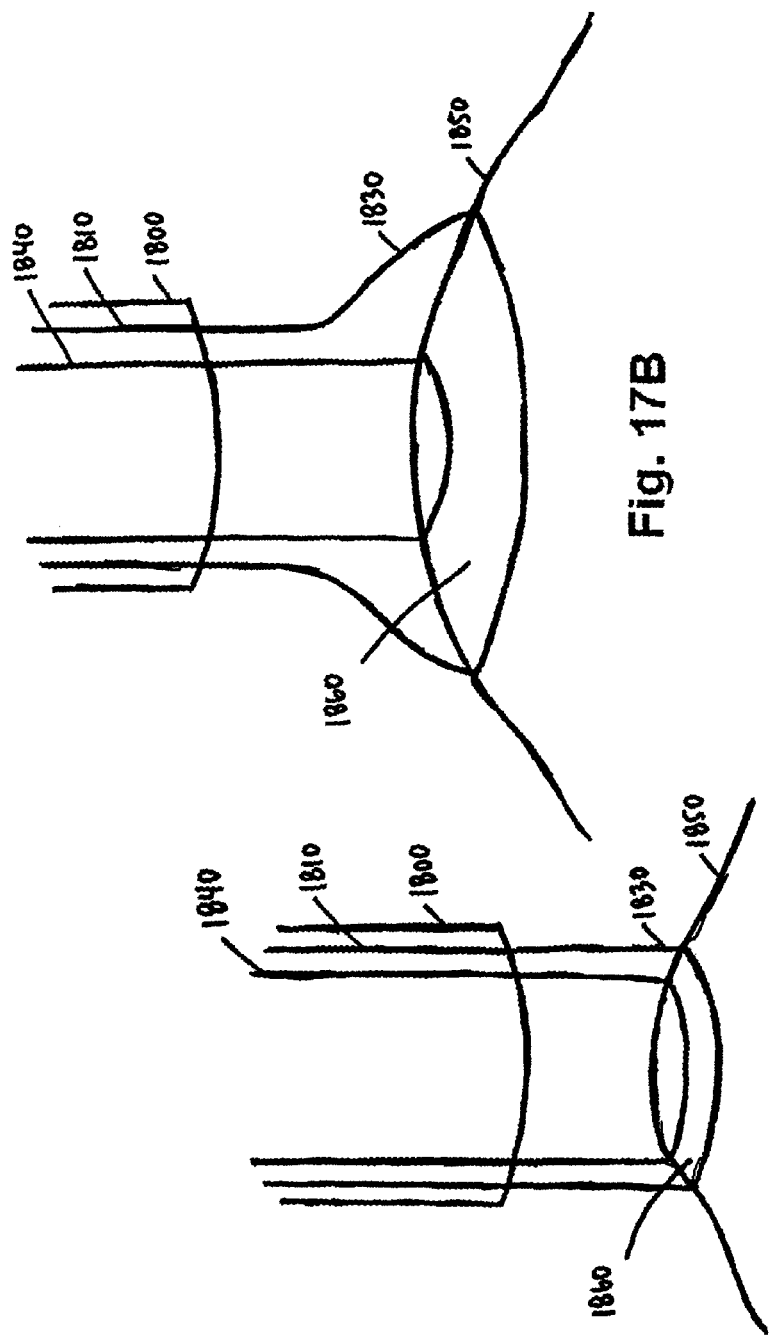

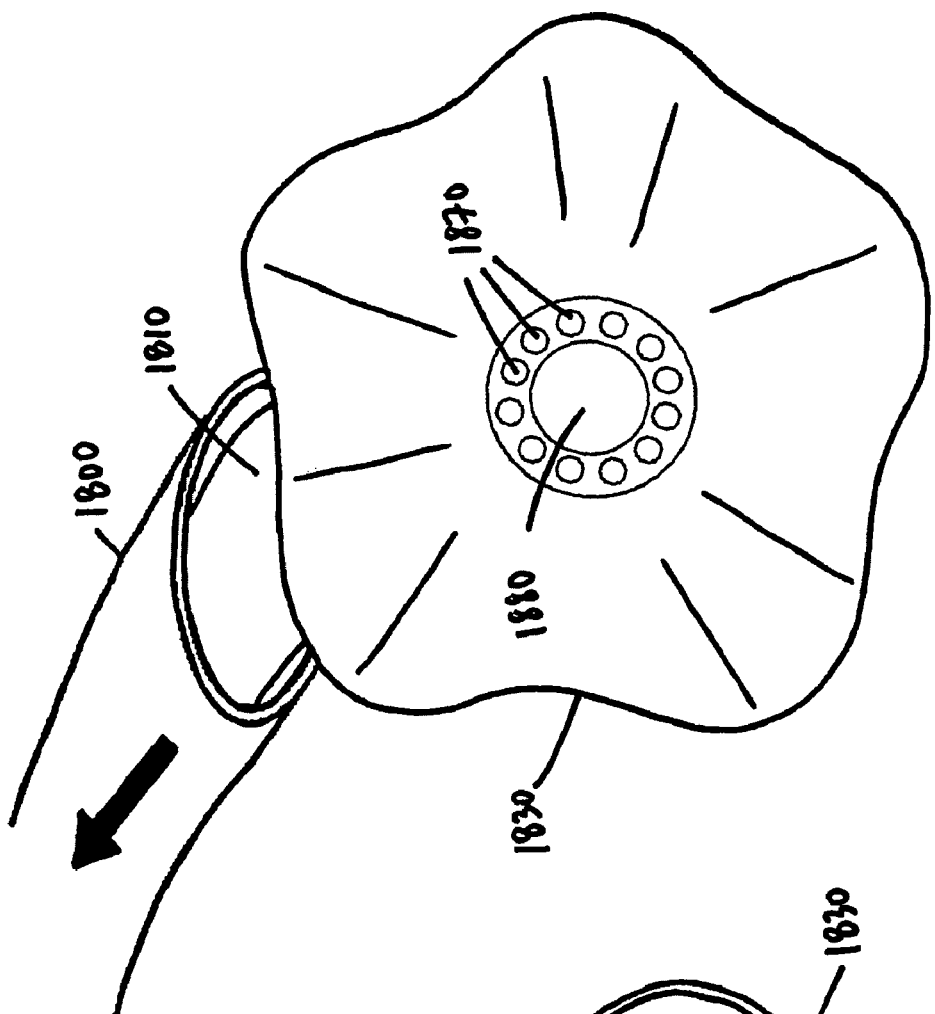
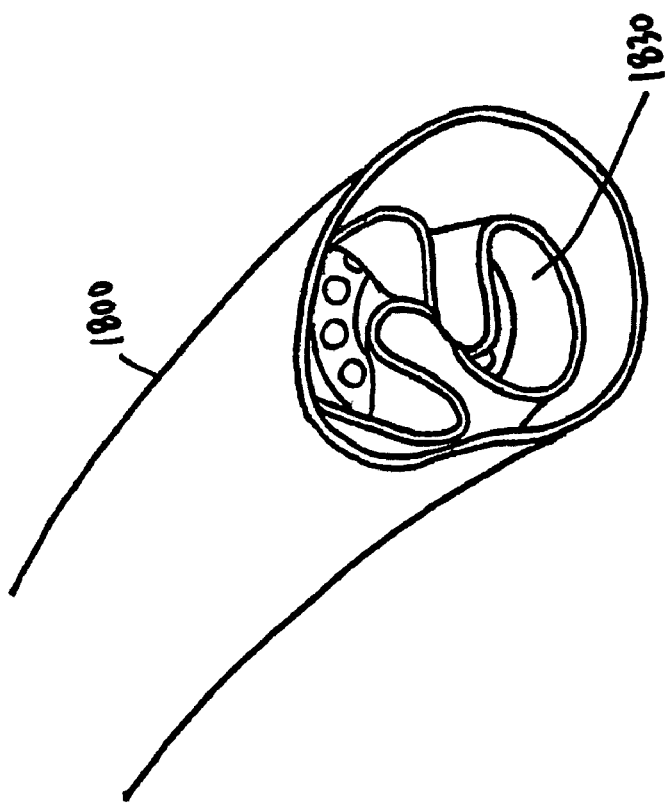

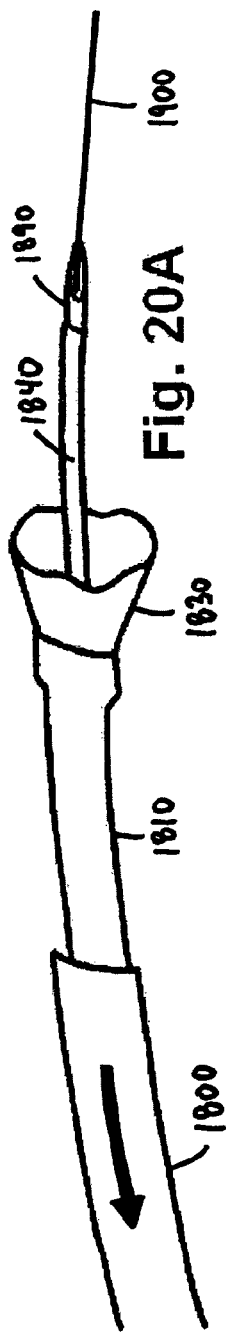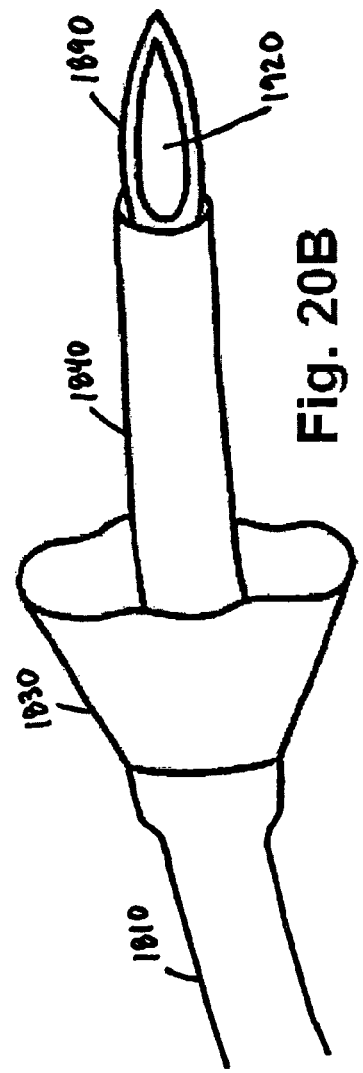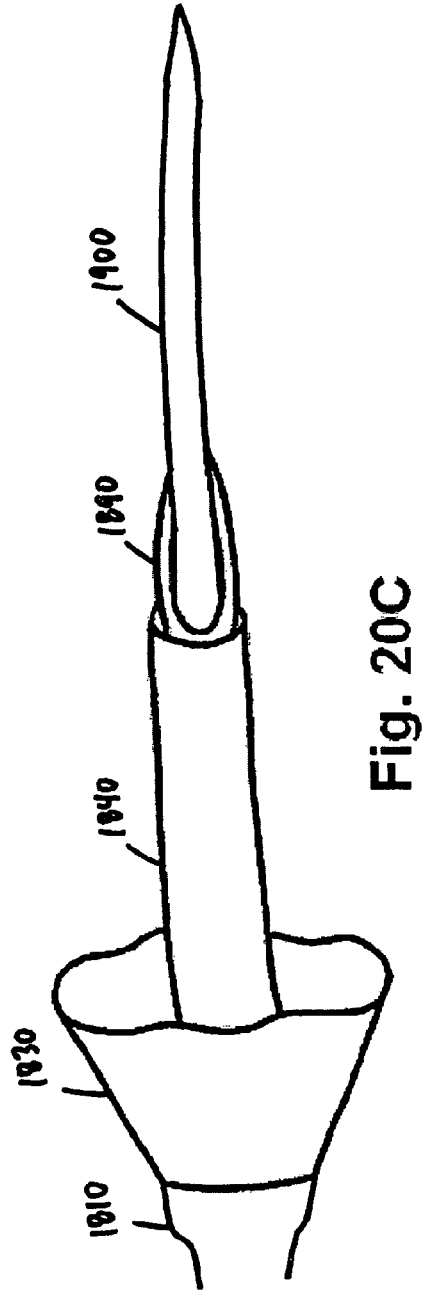

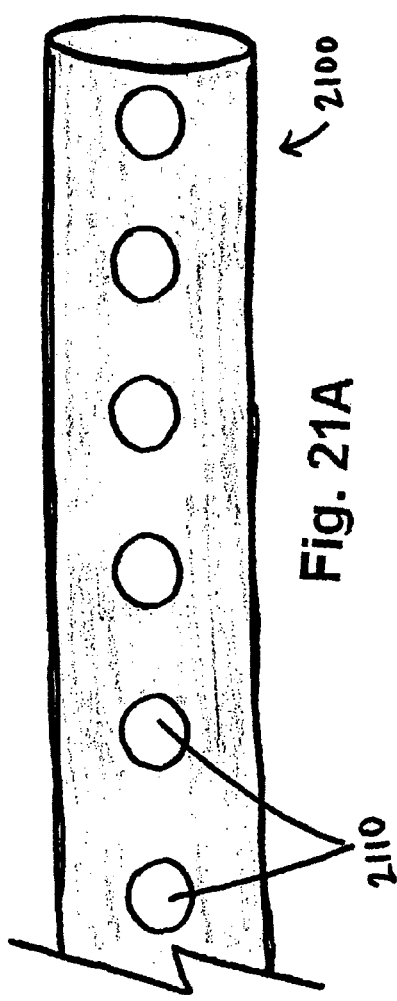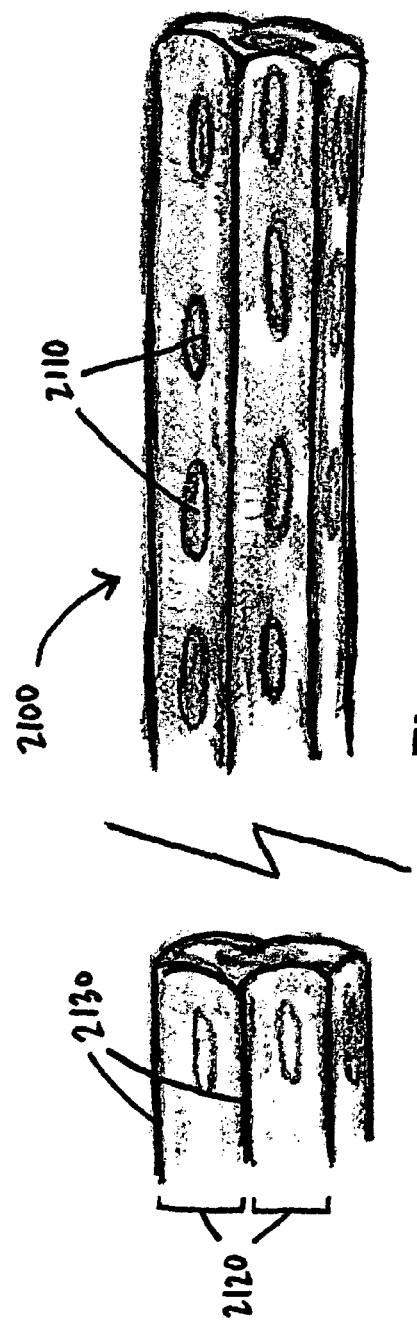
Fig. 21A
Fig. 21B

DEVICES, SYSTEMS, AND METHODS FOR PERICARDIAL ACCESS

The present application is related to, and claims the priority benefit of, International Patent Application Serial No. PCT/US2008/056666, filed Mar. 12, 2008, which is related to, claims the priority benefit of, and in at least some designated countries should be considered a continuation-in-part application of, International Patent Application Serial No. PCT/US2008/053061, filed Feb. 5, 2008, which is related to, claims the priority benefit of, and in at least some designated countries should be considered a continuation-in-part application of, International Patent Application No. PCT/US2007/015207, filed Jun. 29, 2007, which is related to, and claims the priority benefit of, U.S. Provisional Patent Application Ser. No. 60/914,452, filed Apr. 27, 2007, and U.S. Provisional Patent Application Ser. No. 60/817,421, filed Jun. 30, 2006. The present application also claims the priority benefit of International Patent Application Serial No. PCT/US2008/053061, filed Feb. 5, 2008, International Patent Application No. PCT/US2007/015207, filed Jun. 29, 2007, and U.S. Provisional Patent Application Ser. No. 60/914,452, filed Apr. 27, 2007. The contents of each of these applications are hereby incorporated by reference in their entirety into this disclosure.

BACKGROUND

Ischemic heart disease, or coronary heart disease, kills more Americans per year than any other single cause. In 2004, one in every five deaths in the United States resulted from ischemic heart disease. Indeed, the disease has had a profound impact worldwide. If left untreated, ischemic heart disease can lead to chronic heart failure, which can be defined as a significant decrease in the heart's ability to pump blood. Chronic heart failure is often treated with drug therapy.

Ischemic heart disease is generally characterized by a diminished flow of blood to the myocardium and is also often treated using drug therapy. Although many of the available drugs may be administered systemically, local drug delivery ("LDD") directly to the heart can result in higher local drug concentrations with fewer systemic side effects, thereby leading to improved therapeutic outcomes.

Cardiac drugs may be delivered locally via catheter passing through the blood vessels to the inside of the heart. However, endoluminal drug delivery has several shortcomings, such as: (1) inconsistent delivery, (2) low efficiency of localization, and (3) relatively rapid washout into the circulation.

To overcome such shortcomings, drugs may be delivered directly into the pericardial space, which surrounds the external surface of the heart. The pericardial space is a cavity formed between the heart and the relatively stiff pericardial sac that encases the heart. Although the pericardial space is usually quite small because the pericardial sac and the heart are in such close contact, a catheter may be used to inject a drug into the pericardial space for local administration to the myocardial and coronary tissues. Drug delivery methods that supply the agent to the heart via the pericardial space offer several advantages over endoluminal delivery, including: (1) enhanced consistency and (2) prolonged exposure of the drug to the cardiac tissue.

In current practice, drugs are delivered into the pericardial space either by the percutaneous transventricular method or by the transthoracic approach. The percutaneous transventricular method involves the controlled penetration of a catheter through the ventricular myocardium to the pericardial space. The transthoracic approach involves accessing the pericardial space from outside the heart using a sheathed needle with a suction tip to grasp the pericardium, pulling it away from the myocardium to enlarge the pericardial space, and injecting the drug into the space with the needle.

For some patients with chronic heart failure, cardiac resynchronization therapy ("CRT") can be used in addition to drug therapy to improve heart function. Such patients generally have an abnormality in conduction that causes the right and left ventricles to beat (i.e., begin systole) at slightly different times, which further decreases the heart's already-limited function. CRT helps to correct this problem of dyssynchrony by resynchronizing the ventricles, thereby leading to improved heart function. The therapy involves the use of an implantable device that helps control the pacing of at least one of the ventricles through the placement of electrical leads onto specified areas of the heart. Small electrical signals are then delivered to the heart through the leads, causing the right and left ventricles to beat simultaneously.

Like the local delivery of drugs to the heart, the placement of CRT leads on the heart can be challenging, particularly when the target placement site is the left ventricle. Leads can be placed using a transvenous approach through the coronary sinus, by surgical placement at the epicardium, or by using an endocardial approach. Problems with these methods of lead placement can include placement at an improper location (including inadvertent placement at or near scar tissue, which does not respond to the electrical signals), dissection or perforation of the coronary sinus or cardiac vein during placement, extended fluoroscopic exposure (and the associated radiation risks) during placement, dislodgement of the lead after placement, and long and unpredictable times required for placement (ranging from about 30 minutes to several hours).

Clinically, the only approved non-surgical means for accessing the pericardial space include the subxiphoid and the ultrasound-guided apical and parastemal needle catheter techniques, and each methods involves a transthoracic approach. In the subxiphoid method, a sheathed needle with a suction tip is advanced from a subxiphoid position into the mediastinum under fluoroscopic guidance. The catheter is positioned onto the anterior outer surface of the pericardial sac, and the suction tip is used to grasp the pericardium and pull it away from the heart tissue, thereby creating additional clearance between the pericardial sac and the heart. The additional clearance tends to decrease the likelihood that the myocardium will be inadvertently punctured when the pericardial sac is pierced.

Although this technique works well in the normal heart, there are major limitations in diseased or dilated hearts—the very hearts for which drug delivery and CRT lead placement are most needed. When the heart is enlarged, the pericardial space is significantly smaller and the risk of puncturing the right ventricle or other cardiac structures is increased. Additionally, because the pericardium is a very stiff membrane, the suction on the pericardium provides little deformation of the pericardium and, therefore, very little clearance of the pericardium from the heart.

As referenced above, the heart is surrounded by a "sac" referred to as the pericardium. The space between the surface of the heart and the pericardium can normally only accommodate a small amount of fluid before the development of cardiac tamponade, defined as an emergency condition in which fluid accumulates in the pericardium. Therefore, it is not surprising that cardiac perforation can quickly result in tamponade, which can be lethal. With a gradually accumulating effusion, however, as is often the case in a number of diseases, very large effusions can be accommodated without tamponade. The key factor is that once the total intrapericardial volume has caused the pericardium to reach the noncompliant region of its pressure-volume relation, tamponade rapidly develops. Little W. C., Freeman G. L. (2006). "Pericardial Disease." Circulation 113(12): 1622-1632.

Cardiac tamponade occurs when fluid accumulation in the intrapericardial space is sufficient to raise the pressure surrounding the heart to the point where cardiac filling is affected. Ultimately, compression of the heart by a pressurized pericardial effusion results in markedly elevated venous pressures and impaired cardiac output producing shock which, if untreated, it can be rapidly fatal. Id.

The frequency of the different causes of pericardial effusion varies depending in part upon geography and the patient population. Corey G. R. (2007). "Diagnosis and treatment of pericardial effusion." http://patients.uptodate.com. A higher incidence of pericardial effusion is associated with certain diseases. For example, twenty-one percent of cancer patients have metastases to the pericardium. The most common are lung (37% of malignant effusions), breast (22%), and leukemia/lymphoma (17%). Patients with HIV, with or without AIDS, are found to have increased prevalence, with 41-87% having asymptomatic effusion and 13% having moderate-to-severe effusion. Strimel W. J. e. a. (2006). "Pericardial Effusion." http://www.emedicine.com/med/topic1786.htm.

End-stage renal disease is a major public health problem. In the United States, more than 350,000 patients are being treated with either hemodialysis or continuous ambulatory peritoneal dialysis. Venkat A., Kaufmann K. R., Venkat K. (2006). "Care of the end-stage renal disease patient on dialysis in the ED." Am J Emerg Med 24(7): 847-58. Renal failure is a common cause of pericardial disease, producing large pericardial effusions in up to 20% of patients. Task Force members, Maisch B., Seferovic P. M., Ristic A. D., Erbel R., Rienmuller R., Adler Y., Tomkowski W. Z., Thiene G., Yacoub M. H., ESC Committee for Practice Guidelines, Priori S. G., Alonso Garcia M. A., Blanc J.-J., Budaj A., Cowie M., Dean V., Deckers J., Fernandez Burgos E., Lekakis J., Lindahl B., Mazzotta G., Moraies J., Oto A., Smiseth O. A., Document Reviewers, Acar J., Arbustini E., Becker A. E., Chiaranda G., Hasin Y., Jenni R., Klein W., Lang I., Luscher T. F., Pinto F. J., Shabetai R., Simoons M. L., Soler Soler J., Spodick D. H. (2004). "Guidelines on the Diagnosis and Management of Pericardial Diseases Executive Summary: The Task Force on the Diagnosis and Management of Pericardial Diseases of the European Society of Cardiology." Eur Heart J 25(7): 587-610.

Viral pericarditis is the most common infection of the pericardium. Inflammatory abnormalities are due to direct viral attack, the immune response (antiviral or anticardiac), or both. Id. Purulent (bacterial) pericarditis in adults is rare, but always fatal if untreated. Mortality rate in treated patients is 40%, mostly due to cardiac tamponade, toxicity, and constriction. It is usually a complication of an infection originating elsewhere in the body, arising by contiguous spread or haematogenous dissemination. Id. Other forms of pericarditis include tuberculous and neoplastic.

The most common secondary malignant tumors are lung cancer, breast cancer, malignant melanoma, lymphomas, and leukemias. Effusions may be small or large with an imminent tamponade. In almost two-thirds of the patients with documented malignancy pericardial effusion is caused by non-malignant diseases, e.g., radiation pericarditis, or opportunistic infections. The analyses of pericardial fluid, pericardial or epicardial biopsy are essential for the confirmation of malignant pericardial disease. Id.

Management of pericardial effusions continues to be a challenge. There is no uniform consensus regarding the best way to treat this difficult clinical entity. Approximately half the patients with pericardial effusions present with symptoms of cardiac tamponade. In these cases, symptoms are relieved by pericardial decompression, irrespective of the underlying cause. Georghiou G. P., Stamler A., Sharoni E., Fichman-Horn S., Berman M., Vidne B. A., Saute M. (2005). "Video-Assisted Thoracoscopic Pericardial Window for Diagnosis and Management of Pericardial Effusions." Ann Thorac Surg 80(2): 607-610. Symptomatic pericardiac effusions are common and may result from a variety of causes. When medical treatment has failed to control the effusion or a diagnosis is needed, surgical intervention is required. Id.

The most effective management of pericardial effusions has yet to be identified. The conventional procedure is a surgically placed pericardial window under general anesthesia. This procedure portends significant operative and anesthetic risks because these patients often have multiple comorbidities. Less invasive techniques such as blind needle pericardiocentesis have high complication and recurrence rates. The technique of echocardiographic-guided pericardiocentesis with extended catheter drainage is performed under local anesthetic with intravenous sedation. Creating a pericardiostomy with a catheter in place allows for extended drainage and sclerotherapy. Echocardiographic-guided pericardiocentesis has been shown to be a safe and successful procedure when performed at university-affiliated or academic institutions. However, practices in community hospitals have rarely been studied in detail. Buchanan C. L., Sullivan V. V., Lampman R., Kulkarni M. G. (2003). "Pericardiocentesis with extended catheter drainage: an effective therapy." Ann Thorac Surg 76(3): 817-82.

The treatment of cardiac tamponade is drainage of the pericardial effusion. Medical management is usually ineffective and should be used only while arrangements are made for pericardial drainage. Fluid resuscitation may be of transient benefit if the patient is volume depleted (hypovolemic cardiac tamponade).

Surgical drainage (or pericardiectomy) is excessive for many patients. The best option is pericardiocentesis with the Seldinger technique, leaving a pigtail drainage catheter that should be kept in place until drainage is complete. Sagrista Sauleda J., Permanyer Miralda G., Soler Soler J. (2005). "[Diagnosis and management of acute pericardial syndromes]." Rev Esp Cardiol 58(7): 830-41. This less-invasive technique resulted in a short operative time and decreased supply, surgeon, and anesthetic costs. When comparing procedure costs of a pericardial window versus an echo-guided pericardiocentesis with catheter drainage at our institution, there was a cost savings of approximately $1,800/case in favor of catheter drainage. In an era of accelerating medical costs, these savings are of considerable importance. Buchanan C. L., Sullivan V. V., Lampman R., Kulkarni M. G. (2003). "Pericardiocentesis with extended catheter drainage: an effective therapy." Ann Thorac Surg 76(3): 817-82.

Clearly, there is a clinical need for a mini-invasive, safe and effective approach to treatment of pericardial effusion and tamponade. The present application takes advantage of a safe and effective pericardial access approach previously disclosed in combination with a special catheter used specifically for fluid drainage, fluid diagnosis, resuscitation and therapy delivery to treat the underlying cause of the effusion.

Thus, there is need for an efficient, easy to use, and relatively inexpensive device, system and technique that can be used to access the heart for local delivery of therapeutic and diagnostic substances, as well as of CRT leads and other types of leads. There is also a need for an efficient, easy to use, and relatively inexpensive device, system and technique that can be used to access a space containing fluid within a tissue to remove the fluid and to optionally deliver a substance if necessary.

BRIEF SUMMARY

Disclosed herein are devices, systems, and methods for engaging a tissue, including, but not limited to, accessing the internal and external tissues of the heart. At least some of the disclosed embodiments provide access to the external surface of the heart through the pericardial space for localized delivery of leads to the heart tissue. In addition, various disclosed embodiments provide devices, systems, and methods for engaging a tissue.

In at least one embodiment of a system for use with a vacuum source for engaging a tissue according to the present disclosure, the system comprises an engagement catheter comprising a proximal end, a distal end, first and second lumens extending between the proximal end and the distal end, and a skirt operatively connected to the distal end, the skirt comprising a proximal end having a circumference substantially similar to an outer circumference of the engagement catheter, the skirt further comprising a distal end having a circumference larger than the outer circumference of the engagement catheter, a delivery catheter comprising a proximal end, a distal end, and a hollow tube extending between the proximal end and the distal end, the delivery catheter configured such that the hollow tube is capable of insertion into the second lumen of the engagement catheter, a needle located at the distal end of the delivery catheter, and a vacuum port located at the proximal end of the engagement catheter, the vacuum port being operatively connected to the first lumen of the engagement catheter and capable of operative connection to the vacuum source, wherein the first lumen of the engagement catheter includes a suction port located at or near the distal end of the engagement catheter, the suction port configured to allow the proximal end of the skirt to removably engage a surface of a tissue such that the skirt is capable of forming a reversible seal with the surface of the tissue when a vacuum source is operatively attached to the vacuum port. In another embodiment, the system is capable of enlarging a pericardial space between the targeted tissue and a pericardial sac that surrounds a heart by retracting the targeted tissue away from the pericardial sac. In yet another embodiment, the tissue engaged by the system is a heart. In an additional embodiment, the system is capable of enlarging a pericardial space between the heart and a pericardial sac when the skirt is attached to an interior wall of the heart.

In at least one embodiment of a system for use with a vacuum source for engaging a tissue according to the present disclosure, the skirt comprises a deformable configuration. In another embodiment, the deformable configuration of the skirt is capable of expanding to an expanded configuration. In yet another embodiment, the expanded configuration is a frusto-conical configuration. In an additional embodiment, the expanded configuration is a an irregular frusto-conical configuration.

In at least one embodiment of a system for use with a vacuum source for engaging a tissue according to the present disclosure, the system further comprises a sleeve comprising a proximal end, a distal end, and a lumen extending between the proximal end and the distal end, wherein the sleeve is positioned circumferentially around the engagement catheter, wherein the sleeve slidingly engages the engagement catheter. In another embodiment, the sleeve may be positioned at the distal end of the engagement catheter, wherein the sleeve at least partially surrounds the skirt. In yet another embodiment, the deformable configuration of the skirt is collapsed when at least partially surrounded by the sleeve.

In at least one embodiment of a system for use with a vacuum source for engaging a tissue according to the present disclosure, the sleeve is positioned along the engagement catheter so not to surround the skirt, wherein the skirt is capable of expanding to an expanded configuration. In another embodiment, the expanded configuration is a frusto-conical configuration. In yet another embodiment, the expanded configuration is a an irregular frusto-conical configuration.

In at least one embodiment of a system for use with a vacuum source for engaging a tissue according to the present disclosure, the targeted tissue comprises a portion of an atrial wall. In another embodiment, the targeted tissue comprises a portion of an atrial appendage. In yet another embodiment, the needle is positioned to be capable of piercing the targeted tissue when the hollow tube is inserted into the second lumen and the suction port is attached to the targeted tissue, such that, when the targeted tissue is pierced, access to the pericardial space is achieved. In an additional embodiment, the system further comprises a guide wire for insertion into the pericardial space. In yet an additional embodiment, the needle comprises a hollow needle in communication with the hollow tube, and the guide wire is capable of insertion through the hollow tube and the hollow needle into the pericardial space.

In at least one embodiment of a system for use with a vacuum source for engaging a tissue according to the present disclosure, the engagement catheter further comprises an injection channel in fluid communication with the second lumen of the engagement catheter, the injection channel being configured to administer a fluid to the targeted tissue. In another embodiment, the fluid comprises an adhesive. In yet another embodiment, the injection channel is ring-shaped.

In at least one embodiment of a system for use with a vacuum source for engaging a tissue according to the present disclosure, the engagement catheter further comprises an injection channel formed along the length of the engagement catheter, the injection channel having at its distal end at least one opening for administering a fluid to the targeted tissue, the injection channel being capable of operable attachment to an external fluid source at the proximal end of the injection channel, such that fluid from the external fluid source can flow through the injection channel to the targeted tissue when the external fluid source is operatively attached to the injection channel. In another embodiment, the needle comprises a needle wire for piercing the targeted tissue. In yet another embodiment, the needle comprises a pressure tip needle.

In at least one embodiment of a system for use with a vacuum source for engaging a tissue according to the present disclosure, the engagement catheter comprises a curvature along a length of the engagement catheter. In another embodiment, the curvature of the engagement catheter forms an angle that is approximately forty-five degrees. In yet another embodiment, the curvature of the engagement catheter forms an angle that is approximately ninety degrees, so that a portion of the engagement catheter is approximately perpendicular to another portion of the engagement catheter. In an additional embodiment, the curvature of the engagement catheter forms an angle so that a portion of the engagement catheter is approximately parallel to another portion of the engagement catheter.

In at least one embodiment of an engagement catheter for use with a vacuum source for engaging a tissue according to the present disclosure, the engagement catheter comprises an elongated tube comprising a proximal end, a distal end, an outer wall positioned circumferentially along the length of the tube, and an inner wall positioned circumferentially along the length of the tube, wherein the outer wall and the inner wall form at least one suction channel along the length of the tube between the outer wall and the inner wall, a skirt operatively connected to the distal end of the tube, the skirt comprising a proximal end having a circumference substantially similar to an outer circumference of the tube, the skirt further comprising a distal end having a circumference larger than the circumference of the tube, a vacuum port in communication with the proximal end of the tube, the vacuum port being operatively connected to the at least one suction channel and capable of operative connection to the vacuum source, and a suction port in communication with the at least one suction channel at the distal end of the tube, the suction port configured to allow the proximal end of the skirt to removably engage a surface of a tissue such that the skirt is capable of forming a reversible seal with the surface of the tissue when a vacuum source is operatively attached to the vacuum port. In another embodiment, the skirt comprises a deformable configuration. In yet another embodiment, the deformable configuration of the skirt is capable of expanding to an expanded configuration. In an additional embodiment, the expanded configuration is a frusto-conical configuration. In yet an additional embodiment, the expanded configuration is a an irregular frusto-conical configuration.

In at least one embodiment of an engagement catheter for use with a vacuum source for engaging a tissue according to the present disclosure, the skirt has a collapsed configuration when the skirt is at least partially surrounded by a sleeve, and wherein the skirt has an expanded configuration when the skirt is not surrounded by the sleeve. In another embodiment, wherein the tissue engaged by the skirt of the engagement catheter is a heart. In yet another embodiment, wherein the skirt is capable of enlarging a pericardial space between the heart and a pericardial sac when the skirt is attached to an interior wall of the heart.

In at least one embodiment of an engagement catheter for use with a vacuum source for engaging a tissue according to the present disclosure, the engagement catheter further comprises at least one internal lumen support positioned within the at least one suction channel and attached to the outer wall and the inner wall, the at least one internal lumen support extending from the distal end of the tube along at least a substantial portion of the length of the tube. In another embodiment, wherein the at least one internal lumen support comprises two internal lumen supports, and the at least one suction channel comprises two suction channels. In yet another embodiment, further comprising an injection channel formed along the length of the tube, the injection channel having at its distal end at least one opening for administering a fluid to the targeted tissue, the injection channel being capable of operable attachment to an external fluid source at the proximal end of the injection channel, such that fluid from the external fluid source can flow through the injection channel to the targeted tissue when the external fluid source is operatively attached to the injection channel.

In at least one embodiment of a method for engaging a tissue according to the present disclosure, the method comprises the steps of providing a system, comprising an engagement catheter comprising a proximal end, a distal end, first and second lumens extending between the proximal end and the distal end, and a skirt operatively connected to the distal end, the skirt comprising a proximal end having a circumference substantially similar to an outer circumference of the engagement catheter, the skirt further comprising a distal end having a circumference larger than the outer circumference of the engagement catheter, a delivery catheter comprising a proximal end, a distal end, and a hollow tube extending between the proximal end and the distal end, the delivery catheter configured such that the hollow tube is capable of insertion into the second lumen of the engagement catheter, a needle located at the distal end of the delivery catheter, and a vacuum port located at the proximal end of the engagement catheter, the vacuum port being operatively connected to the first lumen of the engagement catheter and capable of operative connection to the vacuum source, wherein the first lumen of the engagement catheter includes a suction port located at or near the distal end of the engagement catheter, the suction port configured to allow the proximal end of the skirt to removably engage a surface of a targeted tissue such that the skirt is capable of forming a reversible seal with the surface of the targeted tissue when a vacuum source is operatively attached to the vacuum port, and inserting the engagement catheter into a body such that the distal end of the engagement catheter is positioned at or near the targeted tissue.

In another embodiment, the system is capable of enlarging a pericardial space between the targeted tissue and a pericardial sac that surrounds a heart by retracting the targeted tissue away from the pericardial sac. In yet another embodiment, the step of inserting the engagement catheter into a body comprises the insertion of the engagement catheter such that the distal end of the engagement catheter is positioned inside the heart and the skirt is in contact with the targeted tissue on the interior of a wall of the heart. In an additional embodiment, the method further comprises the step of operatively connecting a vacuum source to the vacuum port such that the skirt is reversibly attached to the targeted tissue on the interior of a wall of the heart. In at least one embodiment of a method for engaging a tissue according to the present disclosure, the method further comprises the step of inserting the delivery catheter into the second lumen of the engagement catheter In another embodiment, the method further comprises the step of piercing the targeted tissue on the interior of a wall of the heart with the needle. In yet another embodiment, the method further comprises the step of administering a substance into the pericardial space. In an additional embodiment, the method further comprises the steps of withdrawing the needle from the targeted tissue and administering a substance to the targeted tissue after withdrawal of the needle. In yet an additional embodiment, the substance comprises an adhesive for sealing a puncture wound in the targeted tissue.

In at least one embodiment of a method for engaging a tissue according to the present disclosure, the targeted tissue comprises a portion of an atrial wall. In another embodiment, the targeted tissue comprises a portion of an atrial appendage. In yet another embodiment, the method further comprises the step of accessing the pericardial space by inserting a guide wire through the wall of the heart into the pericardial space.

In at least one embodiment of catheter for use with a vacuum source for removing fluid from a tissue according to the present disclosure, the catheter comprises an elongated tube comprising a proximal end, a distal end, an outer wall positioned circumferentially along the length of the tube, and an inner wall positioned circumferentially along the length of the tube defining a lumen within the tube, wherein the inner wall forms at least one suction channel along the length of the tube, one or more apertures defined along the tube, wherein the one or more apertures extend from the outer wall of the tube to the inner wall of the tube, the one or more apertures present at or near the distal end of the tube, wherein at least one of the one or more apertures is/are in communication with the at least one suction channel, a vacuum port in communication with the proximal end of the tube, the vacuum port being operatively connected to the at least one suction channel and capable of operative connection to the vacuum source, the suction channel configured to allow fluid present within a space in a body to enter the one or more apertures in communication with the at least one suction channel and be removed via the at least one suction channel when the vacuum source is operatively attached to the vacuum port. In another embodiment, at least one concave groove is defined on the outer wall extending along at least part of the length of the tube. In yet another embodiment, the one or more apertures defined along the tube are defined along the at least one concave groove. In an additional embodiment, the at least one concave groove defines one or more ridges extending along at least part of the length of the tube, wherein said ridges are configured and arranged to allow for a clearance between a tissue and the one or more apertures.

In at least one embodiment of catheter for use with a vacuum source for removing fluid from a tissue according to the present disclosure, the at least one concave groove comprises at least three concave grooves. In another embodiment, the one or more apertures comprise at least three apertures. In yet another embodiment, the catheter comprises a curvature along a length of the catheter. In an additional embodiment, the catheter further comprises at least one delivery channel defined within the tube and positioned along the length of the tube, wherein at least one of the one or more apertures is/are in communication with the at least one delivery channel.

In at least one embodiment of catheter for use with a vacuum source for removing fluid from a tissue according to the present disclosure, the at least one delivery catheter is operable to deliver a substance from a delivery source present at a proximal end of the delivery channel through at least one of the one or more apertures in communication with the at least one delivery channel for delivery to a target site. In another embodiment, the substance comprises a substance of at least one from the group consisting of a gas, a liquid, and a particulate. In yet another embodiment, the substance comprises a substance of at least one from the group consisting of an antibiotic, a cytostatic agent, a sclerosing agent, a cytotoxic agent, an immunomodulator, and a crystalloid glucocorticoid. In an additional embodiment, the vacuum port is further capable of operative connection to a delivery source, and wherein the suction channel is configured to deliver a substance when a delivery source containing the substance is operatively attached to the vacuum port, wherein the substance is delivered from the delivery source through the suction channel and through at least one of the one or more apertures in communication with the at least one suction channel to a target site. In yet an additional embodiment, the vacuum source comprises a syringe.

In at least one embodiment of a system for use with a vacuum source for removing fluid from a tissue according to the present disclosure, the system comprises an engagement catheter comprising a proximal end, a distal end, and a lumen extending between the proximal end and the distal end, a suction catheter comprising an elongated tube comprising a proximal end, a distal end, an outer wall positioned circumferentially along the length of the tube, and an inner wall positioned circumferentially along the length of the tube defining a lumen within the tube, wherein the inner wall forms at least one suction channel along the length of the tube, one or more apertures defined along the tube, wherein the one or more apertures extend from the outer wall of the tube to the inner wall of the tube, the one or more apertures present at or near the distal end of the tube, wherein at least one of the one or more apertures is/are in communication with the at least one suction channel, a vacuum port in communication with the proximal end of the tube, the vacuum port being operatively connected to the at least one suction channel and capable of operative connection to the vacuum source, the suction channel configured to allow fluid present within a space in a body to enter the one or more apertures in communication with the at least one suction channel and be removed via the at least one suction channel when the vacuum source is operatively attached to the vacuum port, wherein the suction catheter is configured so that it is capable of insertion into the lumen of the engagement catheter. In another embodiment, the suction catheter is operable to enter a space of a tissue via insertion through the lumen of the engagement catheter. In yet another embodiment, the suction catheter is operable to enter a right atrial appendage of a heart via insertion through the lumen of the engagement catheter. In an additional embodiment, the suction catheter is further operable to enter a visceral pericardium of a heart to access a pericardial sac.

In at least one embodiment of a system for use with a vacuum source for removing fluid from a tissue according to the present disclosure, at least one concave groove is defined on the outer wall of the suction catheter extending along at least part of the length of the tube. In another embodiment, the one or more apertures defined along the tube are defined along the at least one concave groove. In yet another embodiment, the at least one concave groove defines one or more ridges extending along at least part of the length of the tube, wherein said ridges are configured and arranged to allow for a clearance between a tissue and the one or more apertures. In an additional embodiment, the catheter suction comprises a curvature along a length of the suction catheter.

In at least one embodiment of a system for use with a vacuum source for removing fluid from a tissue according to the present disclosure, wherein the suction catheter further comprises at least one delivery channel defined within the tube and positioned along the length of the tube, wherein at least one of the one or more apertures is/are in communication with the at least one delivery channel. In another embodiment, the at least one delivery catheter is operable to deliver a substance from a delivery source present at a proximal end of the delivery channel through at least one of the one or more apertures in communication with the at least one delivery channel for delivery to a target site. In yet another embodiment, the substance comprises a substance of at least one from the group consisting of a gas, a liquid, and a particulate.

In at least one embodiment of a system for use with a vacuum source for removing fluid from a tissue according to the present disclosure, the substance comprises a substance of at least one from the group consisting of an antibiotic, a cytostatic agent, a sclerosing agent, a cytotoxic agent, an immunomodulator, and a crystalloid glucocorticoid. In another embodiment, the vacuum port is further capable of operative connection to a delivery source, and wherein the suction channel is configured to deliver a substance when a delivery source containing the substance is operatively attached to the vacuum port, wherein the substance is delivered from the delivery source through the suction channel and through at least one of the one or more apertures in communication with the at least one suction channel to a target site. In yet another embodiment, the vacuum source comprises a syringe.

In at least one embodiment of a method for using a suction catheter to remove fluid from a tissue according to the present disclosure, the method comprising the steps of providing a system, comprising an engagement catheter comprising a proximal end, a distal end, and a first lumen extending between the proximal end and the distal end, and a suction catheter comprising an elongated tube comprising a proximal end, a distal end, an outer wall positioned circumferentially along the length of the tube, and an inner wall positioned circumferentially along the length of the tube defining a lumen within the tube, wherein the inner wall forms at first channel along the length of the tube, one or more apertures defined along the tube, wherein the one or more apertures extend from the outer wall of the tube to the inner wall of the tube, the one or more apertures present at or near the distal end of the tube, wherein at least one of the one or more apertures is/are in communication with the first channel, a first port in communication with the proximal end of the tube, the first port being operatively connected to the first channel and capable of operative connection to the first vacuum source, the channel configured to allow fluid present within a space in a body to enter the one or more apertures in communication with the first channel and be removed via the first channel when the first vacuum source is operatively attached to the first port, wherein the suction catheter is configured so that it is capable of insertion into the first lumen of the engagement catheter, inserting the engagement catheter into a body such that the distal end of the engagement catheter is positioned at or near a tissue wall surrounding a space within a tissue, and inserting the suction catheter into the first lumen of the engagement catheter wherein the suction catheter exits the distal end of the engagement catheter through the tissue wall so that the distal end of the suction catheter is present within the space surrounded by the tissue wall and in contact with a fluid present within said space. In another embodiment, the method further comprises the step of operatively connecting a first vacuum source to the first port such that at least a portion of the fluid present within said space enters the one or more apertures in communication with the first channel and is removed via the first channel. In yet another embodiment, at least one concave groove is defined on the outer wall extending along at least part of the length of the tube.

In at least one embodiment of a method for using a suction catheter to remove fluid from a tissue according to the present disclosure, the one or more apertures defined along the tube are defined along the at least one concave groove. In another embodiment, the at least one concave groove defines one or more ridges extending along at least part of the length of the tube, wherein said ridges are configured and arranged to allow for a clearance between a tissue and the one or more apertures. In yet another embodiment, the tissue wall is a right atrial appendage of a heart. In an additional embodiment, the tissue wall is a visceral pericardium of a heart.

In at least one embodiment of a method for using a suction catheter to remove fluid from a tissue according to the present disclosure, the first port is further capable of operative connection to a delivery source, and wherein the first channel is configured to deliver a substance when a delivery source containing the substance is operatively attached to the first port. In another embodiment, the method further comprises the step of operatively connecting a delivery source containing a substance to the first port such that at least a portion of the substance present within the delivery source is delivered from the delivery source through the first channel and through at least one of the one or more apertures in communication with the first channel to a target site. In yet another embodiment, the substance comprises a substance of at least one from the group consisting of an antibiotic, a cytostatic agent, a sclerosing agent, a cytotoxic agent, an immunomodulator, and a crystalloid glucocorticoid. In an additional embodiment, the method further comprises the step of operatively connecting a first vacuum source to the first port such that at least a portion of the substance present within said space enters the one or more apertures in communication with the first channel and is removed via the first channel.

In at least one embodiment of a method for using a suction catheter to remove fluid from a tissue according to the present disclosure, the suction catheter further comprises a second lumen defining a second channel positioned within and along the length of the tube, wherein one or more delivery apertures are defined along the tube, and wherein the one or more delivery apertures extend from the outer wall of the tube to the second lumen of the tube, the one or more delivery apertures present at or near the distal end of the tube. In another embodiment, a second port is in communication at or near the proximal end of the tube, the second port being operably connected to the second channel, wherein the second port is further capable of operative connection to a delivery source, and wherein the second channel is configured to deliver a substance when a delivery source containing the substance is operatively attached to the second port. In yet another embodiment, the method further comprises the step of operatively connecting a delivery source containing a substance to the second port such that at least a portion of the substance present within the delivery source is delivered from the delivery source through the second channel and through at least one of the one or more delivery apertures in communication with the second channel to a target site.

In at least one embodiment of a method for using a suction catheter to remove fluid from a tissue according to the present disclosure, the method comprises the steps of providing a system, comprising, an engagement catheter comprising a proximal end, a distal end, and a first lumen extending between the proximal end and the distal end, a piercing catheter comprising a proximal end, a distal end, and a hollow cylinder extending between the proximal end and the distal end, the piercing catheter having a needle at the distal end of the delivery catheter, the piercing catheter configured such that the hollow cylinder is capable of insertion into the first lumen of the engagement catheter, and a suction catheter comprising an elongated tube comprising a proximal end, a distal end, an outer wall positioned circumferentially along the length of the tube, and an inner wall positioned circumferentially along the length of the tube defining a lumen within the tube, wherein the inner wall forms at first channel along the length of the tube, one or more apertures defined along the tube, wherein the one or more apertures extend from the outer wall of the tube to the inner wall of the tube, the one or more apertures present at or near the distal end of the tube, wherein at least one of the one or more apertures is/are in communication with the first channel, a first port in communication with the proximal end of the tube, the first port being operatively connected to the first channel and capable of operative connection to the first vacuum source, the channel configured to allow fluid present within a space in a body to enter the one or more apertures in communication with the first channel and be removed via the first channel when the first vacuum source is operatively attached to the first port, wherein the suction catheter is configured so that it is capable of insertion into the first lumen of the engagement catheter, inserting the engagement catheter into a body such that the distal end of the engagement catheter is positioned at or near a tissue wall surrounding a space within a tissue, inserting the piercing catheter into the first lumen of the engagement catheter wherein the piercing catheter exists the distal end of the engagement catheter and pierces the tissue wall with the needle of the piercing catheter, removing the piercing catheter from the engagement catheter, inserting the suction catheter into the first lumen of the engagement catheter wherein the suction catheter exits the distal end of the engagement catheter through the tissue wall so that the distal end of the suction catheter is present within the space surrounded by the tissue wall and in contact with a fluid present within said space, and operatively connecting a first vacuum source to the first port such that at least a portion of the fluid present within said space enters the one or more apertures in communication with the first channel and is removed via the first channel.

In at least one embodiment of a method for engaging a tissue according to the present disclosure, the method further comprises the step of removing the delivery catheter from the engagement catheter. In another embodiment, the method further comprises the step of inserting a suction catheter into the second lumen of the engagement catheter, wherein the suction catheter exits the distal end of the engagement catheter through the pierced tissue so that a distal end of the suction catheter is present within a space at least partially surrounded by the pierced tissue and in contact with a fluid present within said space. In yet another embodiment, the suction catheter comprises an elongated suction tube comprising a proximal end, a distal end, an outer wall positioned circumferentially along the length of the suction tube, and an inner wall positioned circumferentially along the length of the suction tube defining a lumen within the suction tube, wherein the inner wall forms at first channel along the length of the suction tube, one or more apertures defined along the tube, wherein the one or more apertures extend from the outer wall of the tube to the inner wall of the suction tube, the one or more apertures present at or near the distal end of the suction tube, wherein at least one of the one or more apertures is/are in communication with the first channel, a suction catheter port in communication with the proximal end of the suction tube, the suction catheter port being operatively connected to the first channel and capable of operative connection to a suction catheter vacuum source, the first channel configured to allow fluid present within a space in a body to enter the one or more apertures in communication with the first channel and be removed via the first channel when the suction catheter vacuum source is operatively attached to the suction catheter port, wherein the suction catheter is configured so that it is capable of insertion into the second lumen of the engagement catheter. In an additional embodiment, the method further comprises the step of operatively connecting a suction catheter vacuum source to the suction catheter port such that at least a portion of the fluid present within said space enters the one or more apertures in communication with the first channel and is removed via the first channel.

BRIEF DESCRIPTION OF THE DRAWINGS

FIG. 4A to 4C show a closure of a hole in the atrial wall using an embodiment as disclosed herein;

FIG. 5A shows an embodiment of an engagement catheter as disclosed herein;

FIG. 5B shows a cross-sectional view of the proximal end of the engagement catheter shown in FIG. 5A;

FIG. 5C shows a cross-sectional view of the distal end of the engagement catheter shown in FIG. 5A;

FIG. 6A shows an embodiment of a delivery catheter as disclosed herein; FIG. 6B shows a close-up view of the needle shown in FIG. 6A;

FIG. 6C shows a cross-sectional view of the needle shown in FIGS. 6A and 6B;

FIG. 9A shows another embodiment of a steering wire system as disclosed herein, the embodiment being deflected in one location;

FIG. 9B shows the steering wire system shown in FIG. 9A, wherein the steering wire system is deflected at two locations;

FIG. 9C shows the steering wire system shown in FIGS. 9A and 9B in its original position;

FIG. 15C shows the embodiment of FIGS. 15A-15C deployed on the cardiac tissue;

FIG. 17A shows an embodiment of a portion of an apparatus for engaging a tissue that has engaged a tissue, as disclosed herein;

FIG. 17B shows an embodiment of a portion of an apparatus for engaging a tissue having an expanded skirt that has engaged a tissue, as disclosed herein;

FIG. 18A shows an embodiment of a portion of an apparatus for engaging a tissue having a collapsed skirt present within a sleeve, as disclosed herein;

FIG. 18B shows an embodiment of a portion of an apparatus for engaging a tissue having an expanded skirt, as disclosed herein;

FIG. 20A shows an embodiment of a portion of an apparatus for engaging a tissue having a lead positioned therethrough, as disclosed herein;

FIG. 20B shows an embodiment of a portion of an apparatus for engaging a tissue showing a needle, as disclosed herein;

FIG. 20C shows the embodiment of FIG. 20B having a lead positioned therethrough.

FIG. 21A shows an embodiment of a portion of an apparatus for removing fluid from a tissue, as disclosed herein;

FIG. 21B shows an embodiment of a portion of an apparatus comprising grooves for removing fluid from a tissue, as disclosed herein.

DETAILED DESCRIPTION

It will be appreciated by those of skill in the art that the following detailed description of the disclosed embodiments is merely exemplary in nature and is not intended to limit the scope of the appended claims.

The disclosed embodiments include devices, systems, and methods useful for accessing various tissues of the heart from inside the heart. For example, various embodiments provide for percutaneous, intravascular access into the pericardial space through an atrial wall or the wall of an atrial appendage. In at least some embodiments, the heart wall is aspirated and retracted from the pericardial sac to increase the pericardial space between the heart and the sac and thereby facilitate access into the space.

Unlike the relatively stiff pericardial sac, the atrial wall and atrial appendage are rather soft and deformable. Hence, suction of the atrial wall or atrial appendage can provide significantly more clearance of the cardiac structure from the pericardium as compared to suction of the pericardium. Furthermore, navigation from the intravascular region (inside of the heart) provides more certainty of position of vital cardiac structures than does intrathoracic access (outside of the heart).

Access to the pericardial space may be used for identification of diagnostic markers in the pericardial fluid; for pericardiocentesis; and for administration of therapeutic factors with angiogenic, myogenic, and antiarrhythmic potential. In addition, as explained in more detail below, epicardial pacing leads may be delivered via the pericardial space, and an ablation catheter may be used on the epicardial tissue from the pericardial space.

Figure 1A:
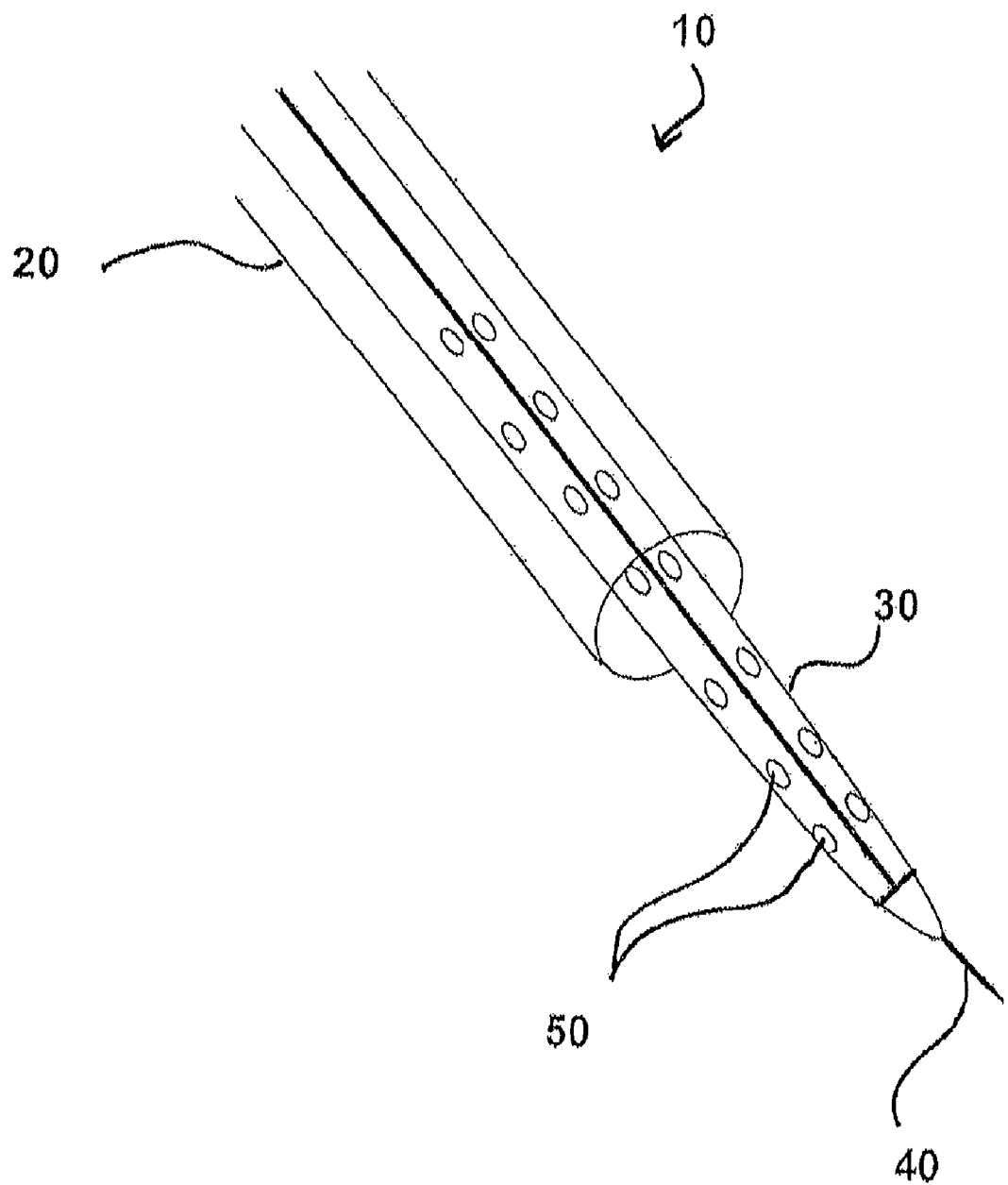
FIG. 1A shows an embodiment of an engagement catheter and an embodiment of a delivery catheter as disclosed herein.

In the embodiment of the catheter system shown in FIG. 1A, catheter system 10 includes an engagement catheter 20, a delivery catheter 30, and a needle 40. Although each of engagement catheter 20, delivery catheter 30, and needle 40 has a proximal end and a distal end, FIG. 1A shows only the distal end. Engagement catheter 20 has a lumen through which delivery catheter 30 has been inserted, and delivery catheter 30 has a lumen through which needle 40 has been inserted. Delivery catheter 30 also has a number of openings 50 that can be used to transmit fluid from the lumen of the catheter to the heart tissue in close proximity to the distal end of the catheter.

Figure 2A:
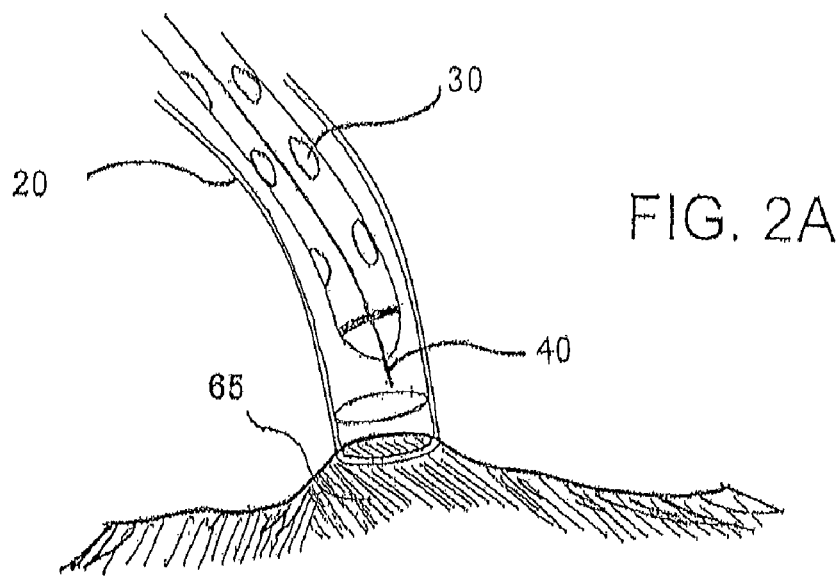
FIG. 2A shows a percutaneous intravascular technique for accessing the pericardial space through a right atrial wall or atrial appendage using the engagement and delivery catheters shown in FIG. 1A.
Figure 2B:
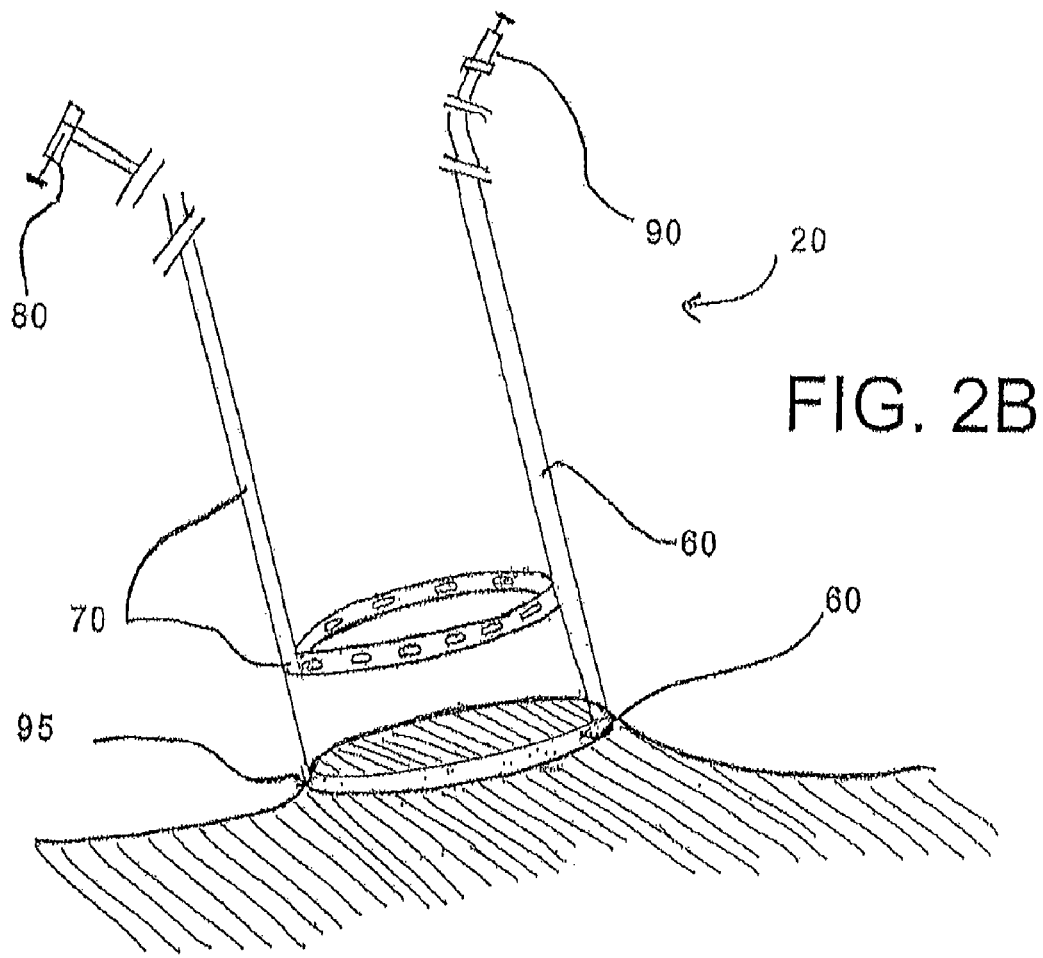
FIG. 2B shows the embodiment of an engagement catheter shown in FIG. 2A.
Figure 2C:
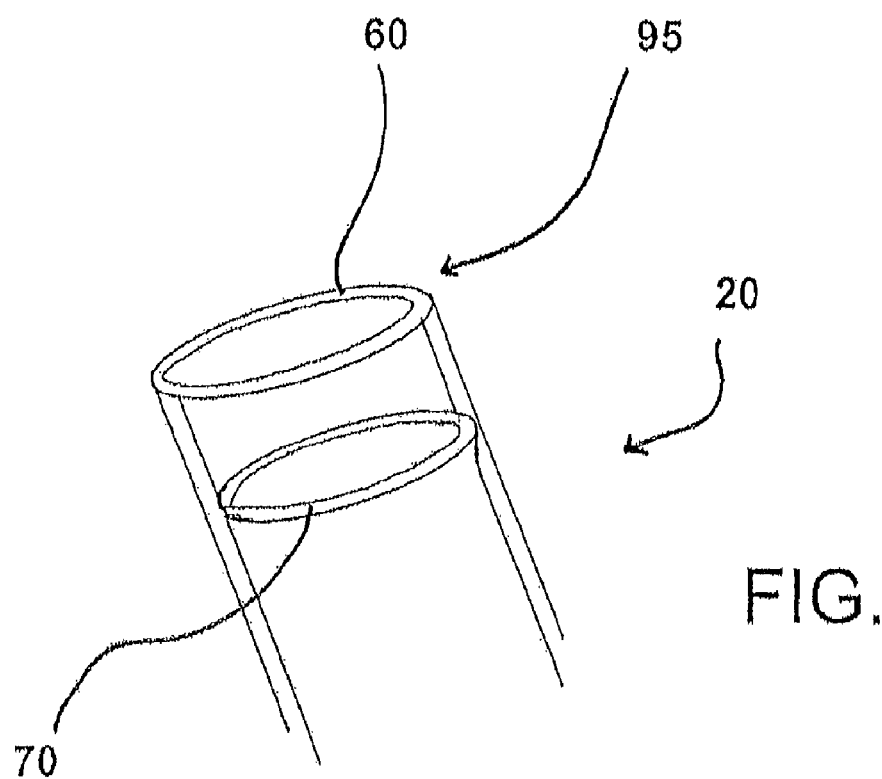
FIG. 2C shows another view of the distal end of the engagement catheter embodiment shown in FIGS. 2A and 2B.

As shown in more detail in FIGS. 2A, 2B, 2C, engagement catheter 20 includes a vacuum channel 60 used for suction of a targeted tissue 65 in the heart and an injection channel 70 used for infusion of substances to targeted tissue 65, including, for example, a biological or non-biological degradable adhesive. As is shown in FIGS. 2B and 2C, injection channel 70 is ring-shaped, which tends to provide relatively even dispersal of the infused substance over the targeted tissue, but other shapes of injection channels may be suitable. A syringe 80 is attached to injection channel 70 for delivery of the appropriate substances to injection channel 70, and a syringe 90 is attached to vacuum channel 60 through a vacuum port (not shown) at the proximal end of engagement catheter 20 to provide appropriate suction through vacuum channel 60. At the distal end of engagement catheter 20, a suction port 95 is attached to vacuum channel 60 for contacting targeted tissue 65, such that suction port 95 surrounds targeted tissue 65, which is thereby encompassed within the circumference of suction port 95. Although syringe 90 is shown in FIG. 2B as the vacuum source providing suction for engagement catheter 20, other types of vacuum sources may be used, such as a controlled vacuum system providing specific suction pressures. Similarly, syringe 80 serves as the external fluid source in the embodiment shown in FIG. 2B, but other external fluid sources may be used.

A route of entry for use of various embodiments disclosed herein is through the jugular or femoral vein to the superior or inferior vena cavae, respectively, to the right atrial wall or atrial appendage (percutaneously) to the pericardial sac (through puncture).

Figure 1B:
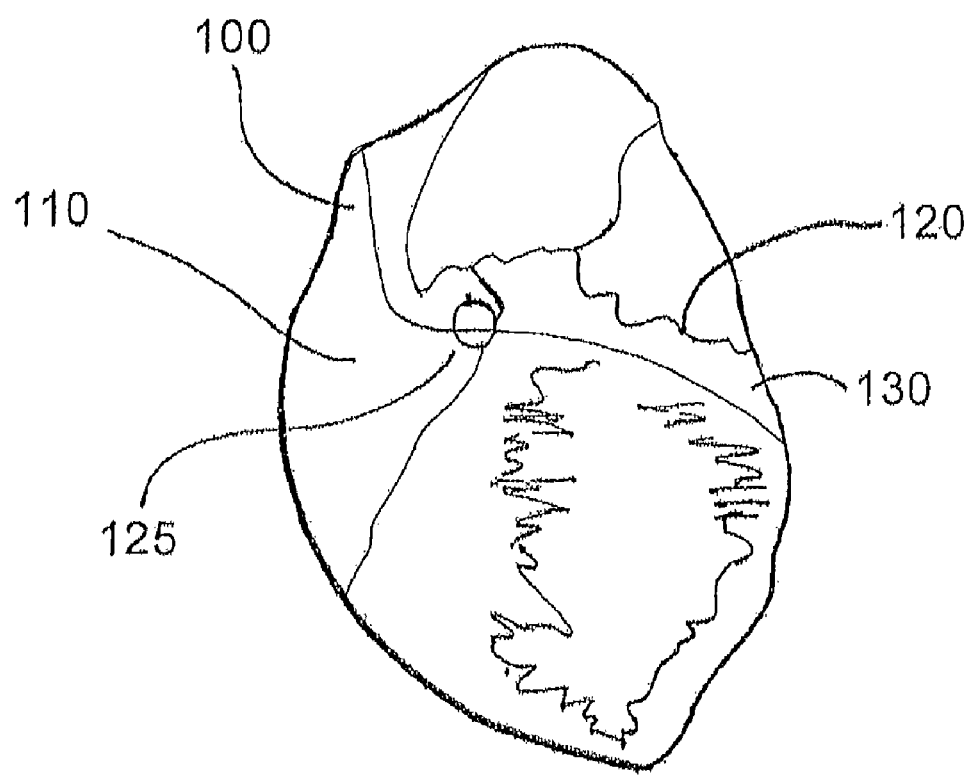
FIG. 1B shows a percutaneous intravascular pericardial delivery using another embodiment of an engagement catheter and another embodiment of a delivery catheter as disclosed herein.

Referring now to FIG. 1B, an engagement catheter 100 is placed via standard approach into the jugular or femoral vein. The catheter, which may be 4 or 5 Fr., is positioned under fluoroscopic or echocardiographic guidance into the right atrial appendage 110. Suction is initiated to aspirate a portion of atrial appendage 110 away from the pericardial sac 120 that surrounds the heart. As explained herein, aspiration of the heart tissue is evidenced when no blood can be pulled back through engagement catheter 100 and, if suction pressure is being measured, when the suction pressure gradually increases. A delivery catheter 130 is then inserted through a lumen of engagement catheter 100. A small perforation can be made in the aspirated atrial appendage 110 with a needle such as needle 40, as shown in FIGS. 1A and 2A. A guide wire (not shown) can then be advanced through delivery catheter 130 into the pericardial space to secure the point of entry 125 through the atrial appendage and guide further insertion of delivery catheter 130 or another catheter. Flouroscopy or echocardiogram can be used to confirm the position of the catheter in the pericardial space. Alternatively, a pressure tip needle can sense the pressure and measure the pressure change from the atrium (about 10 mmHg) to the pericardial space (about 2 mmHg). This is particularly helpful for transseptal access where puncture of arterial structures (e.g., the aorta) can be diagnosed and sealed with an adhesive, as described in more detail below.

Although aspiration of the atrial wall or the atrial appendage retracts the wall or appendage from the pericardial sac to create additional pericardial space, $CO_2$ gas can be delivered through a catheter, such as delivery catheter 130, into the pericardial space to create additional space between the pericardial sac and the heart surface.

Figure 3A:
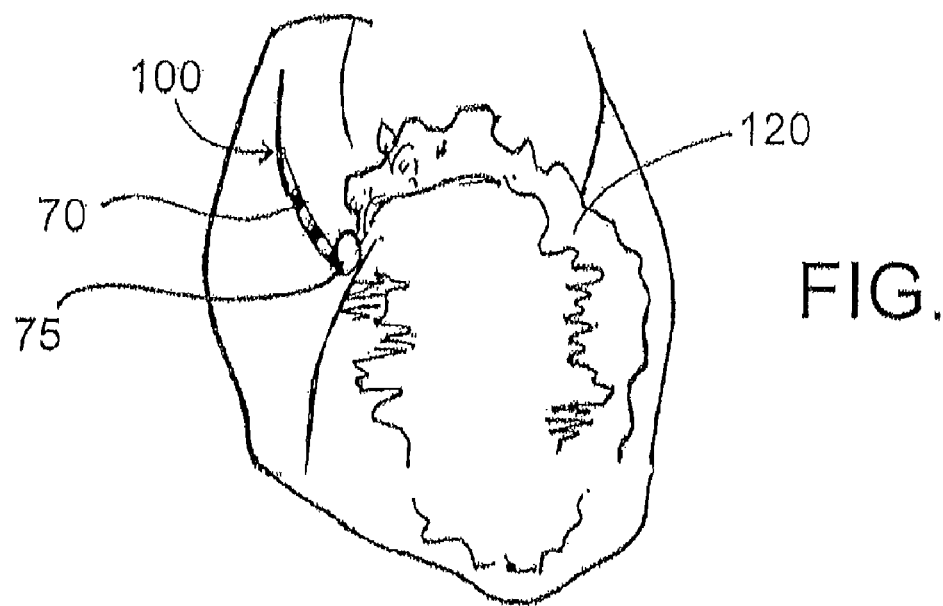
FIG. 3A shows removal of an embodiment of a catheter as disclosed herein.

Referring now to FIG. 3A, the catheter system shown in FIG. 1B is retrieved by pull back through the route of entry.

Figure 3B:
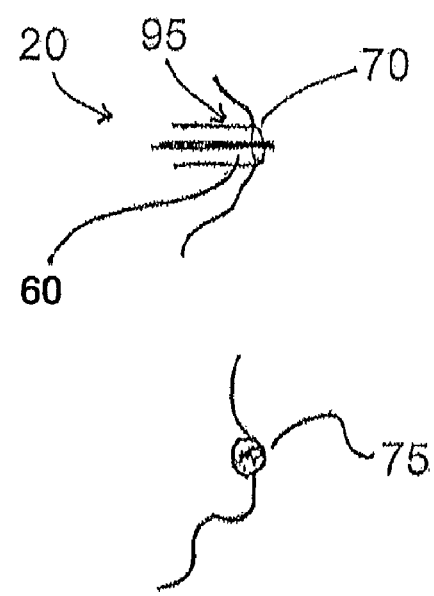
FIG. 3B shows the resealing of a puncture according to an embodiment as disclosed herein.

However, the puncture of the targeted tissue in the heart (e.g., the right atrial appendage as shown in FIG. 3A) may be sealed upon withdrawal of the catheter, which prevents bleeding into the pericardial space. The retrieval of the catheter may be combined with a sealing of the tissue in one of several ways: (1) release of a tissue adhesive or polymer 75 via injection channel 70 to seal off the puncture hole, as shown in FIG. 3B; (2) release of an inner clip or mechanical stitch to close off the hole from the inside of the cavity or the heart, as discussed herein; or (3) mechanical closure of the heart with a sandwich type mechanical device that approaches the hole from both sides of the wall (see FIGS. 4A, 4B, and 4C). In other words, closure may be accomplished by using, for example, a biodegradable adhesive material (e.g., fibrin glue or cyanomethacrylate), a magnetic system, or an umbrella-shaped nitinol stent. An example of the closure of a hole in the atrium is shown in FIG. 3B. Engagement catheter 20 is attached to targeted tissue 95 using suction through suction port 60. Tissue adhesive 75 is injected through injection channel 70 to coat and seal the puncture wound in targeted tissue 95. Engagement catheter 20 is then withdrawn, leaving a plug of tissue adhesive 75 attached to the atrial wall or atrial appendage.

Figure 4D:
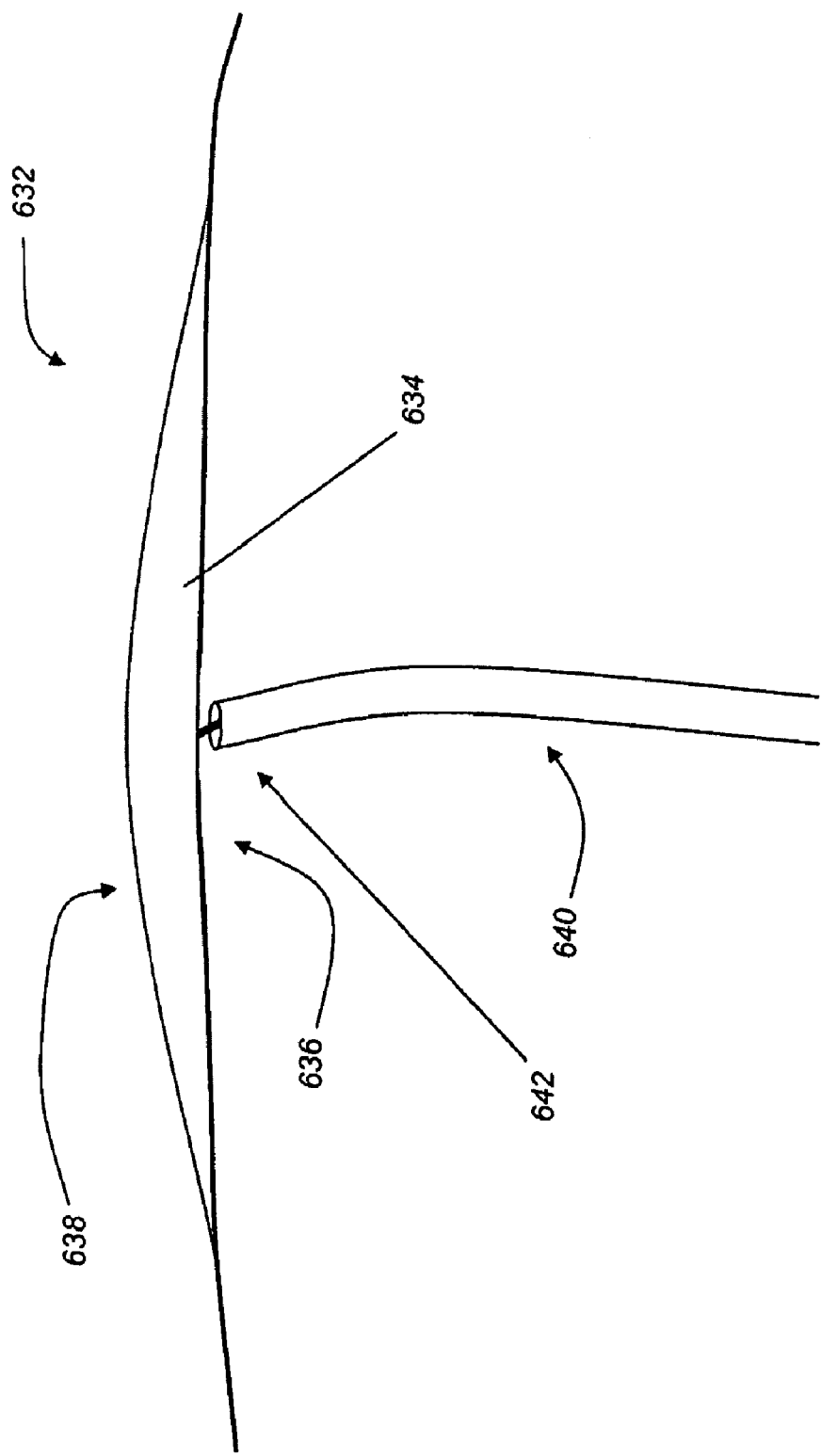
FIG. 4D shows another closure of a hole in cardiac tissue using another embodiment as disclosed herein.

Other examples for sealing the puncture wound in the atrial wall or appendage are shown in FIGS. 4A-4F. Referring now to FIGS. 4A-4C, a sandwich-type closure member, having an external cover 610 and an internal cover 620, is inserted through the lumen of engagement catheter 600, which is attached to the targeted tissue of an atrial wall 630. Each of external and internal covers 610 and 620 is similar to an umbrella in that it can be inserted through a catheter in its folded configuration and expanded to an expanded configuration once it is outside of the catheter. As shown in FIG. 4A, external cover 610 is deployed (in its expanded configuration) on the outside of the atrial wall to seal a puncture wound in the targeted tissue, having already been delivered through the puncture wound into the pericardial space. Internal cover 620 is delivered through engagement catheter 600 (in its folded configuration), as shown in FIGS. 4A and 4B, by an elongated delivery wire 615, to which internal cover 620 is reversibly attached (for example, by a screw-like mechanism). Once internal cover 620 is in position on the inside of atrial wall 630 at the targeted tissue, internal cover 620 is deployed to help seal the puncture wound in the targeted tissue (see FIG. 4C).

Internal cover 620 and external cover 610 may be made from a number of materials, including a shape-memory alloy such as nitinol. Such embodiments are capable of existing in a catheter in a folded configuration and then expanding to an expanded configuration when deployed into the body. Such a change in configuration can result from a change in temperature, for example. Other embodiments of internal and external covers may be made from other biocompatible materials and deployed mechanically.

After internal cover 620 is deployed, engagement catheter 600 releases its grip on the targeted tissue and is withdrawn, leaving the sandwich-type closure to seal the puncture wound, as shown in FIG. 4C. External cover 610 and internal cover 620 may be held in place using a biocompatible adhesive. Similarly, external cover 610 and internal cover 620 may be held in place using magnetic forces, such as, for example, by the inside face (not shown) of external cover 610 comprising a magnet, by the inside face (not shown) of internal cover 620 comprising a magnet, or both inside faces of external cover 610 or internal cover 620 comprising magnets.

In the embodiment shown in FIGS. 4A, 4B, and 4C, the closure member comprises external cover 610 and internal cover 620. However, in at least certain other embodiments, the closure member need not have two covers. For example, as shown in FIG. 4D, closure member 632 is made of only one cover 634. Cover 634 has a first face 636 and a second face 638, and first face 636 is configured for reversible attachment to distal end 642 of delivery wire 640. Closure member 632 may be made of any suitable material, including nitinol, which is capable of transitioning from a folded configuration to an expanded configuration.

Figure 4E:
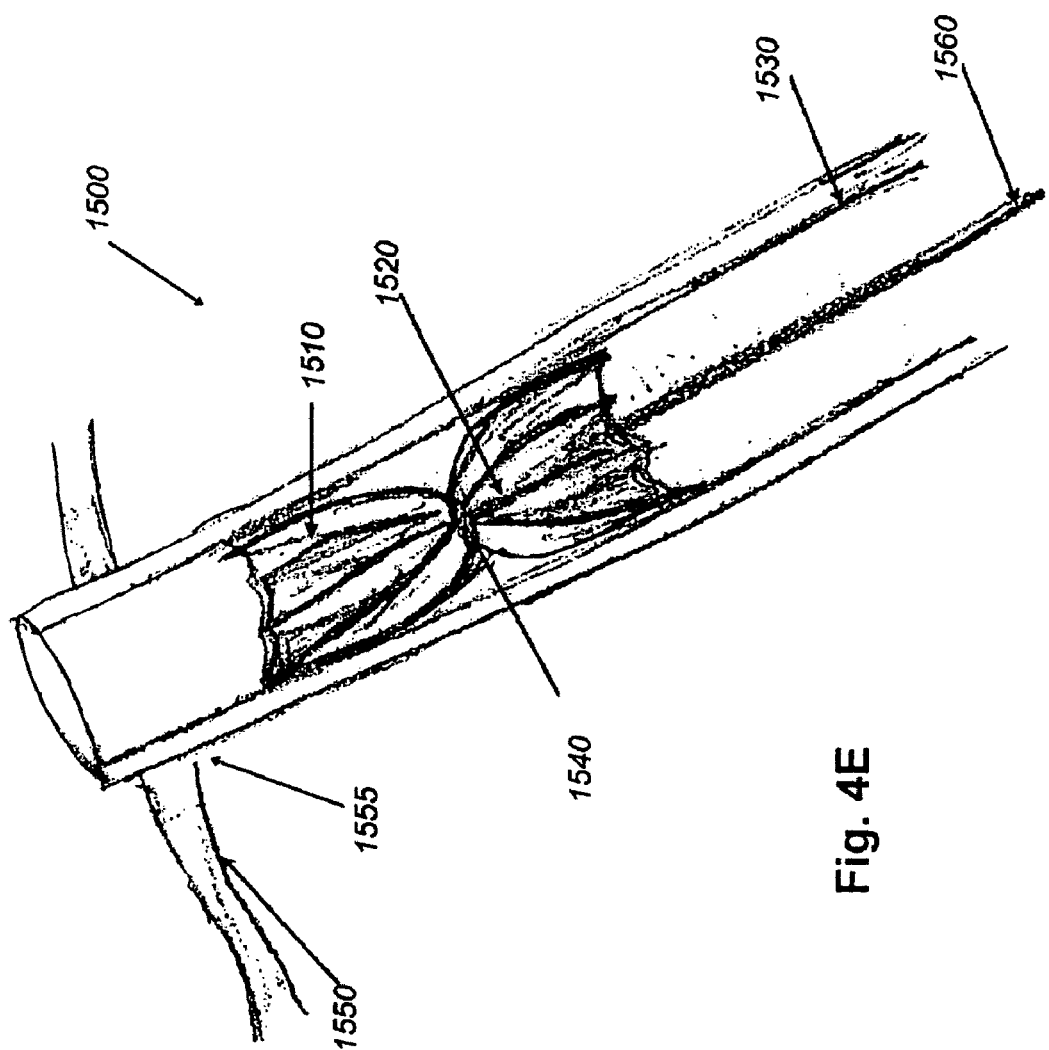
FIG. 4E shows yet another closure of a hole in cardiac tissue using another embodiment as disclosed herein.

In the embodiment shown in FIG. 4E, a closure member 1500 comprises an external cover 1510 and an internal cover 1520 within a delivery catheter 1530. External cover 1510 and internal cover 1520 are attached at a joint 1540, which may be formed, for example, by a mechanical attachment or by a magnetic attachment. In embodiments having a magnetic attachment, each of the external cover and the internal cover may have a ferromagnetic component that is capable of magnetically engaging the other ferromagnetic component.

Delivery catheter 1530 is shown after insertion through hole 1555 of atrial wall 1550. Closure member 1500 may be advanced through delivery catheter 1530 to approach atrial wall 1550 by pushing rod 1560. Rod 1560 may be reversibly attached to internal cover 1520 so that rod 1560 may be disconnected from internal cover 1520 after closure member 1500 is properly deployed. For example, rod 1560 may engage internal cover 1520 with a screw-like tip such that rod 1560 may be easily unscrewed from closure member 1500 after deployment is complete. Alternatively, rod 1560 may simply engage internal cover 1520 such that internal cover 1520 may be pushed along the inside of delivery catheter 1530 without attachment between internal cover 1520 and rod 1560.

Closure member 1500 is advanced through delivery catheter 1530 until external cover 1510 reaches a portion of delivery catheter 1530 adjacent to atrial wall 1550; external cover 1510 is then pushed slowly out of delivery catheter 1530 into the pericardial space. External cover 1510 then expands and is positioned on the outer surface of atrial wall 1550. When external cover 1510 is properly positioned on atrial wall 1550, joint 1540 is approximately even with atrial wall 1550 within hole 1555. Delivery catheter 1530 is then withdrawn slowly, causing hole 1555 to close slightly around joint 1540. As delivery catheter 1530 continues to be withdrawn, internal cover 1520 deploys from delivery catheter 1530, thereby opening into its expanded formation. Consequently, atrial wall 1550 is pinched between internal cover 1520 and external cover 1510, and hole 1555 is closed to prevent leakage of blood from the heart.

Figure 4F:
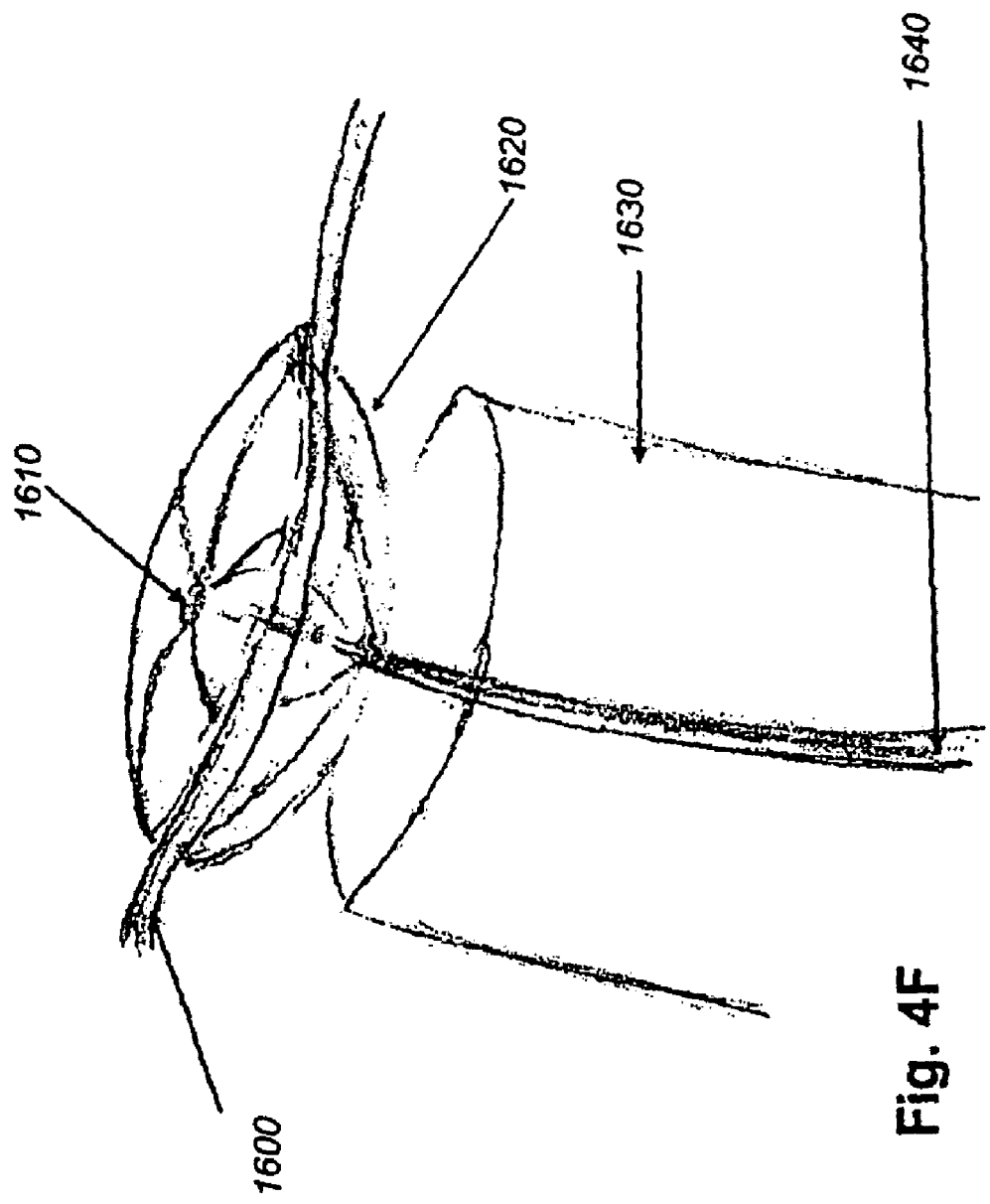
FIG. 4F shows still another closure of a hole in cardiac tissue using another embodiment as disclosed herein.

FIG. 4F shows the occlusion of a hole (not shown) in atrial wall 1600 due to the sandwiching of atrial wall 1600 between an external cover 1610 and an internal cover 1620. External cover 1610 is shown deployed on the outside surface of atrial wall 1600, while delivery catheter 1630 is deployed on the inside surface of atrial wall 1600. As shown, rod 1640 is engaged with internal cover 1620, and delivery catheter 1650 is in the process of being withdrawn, which allows internal cover 1620 to fully deploy. Rod 1640 is then withdrawn through delivery catheter 1630. An engagement catheter (not shown) may surround delivery catheter 1650, as explained more fully herein.

Other examples for sealing a puncture wound in the cardiac tissue are shown in FIGS. 12-15. Referring now to FIG. 12A, there is shown a plug 650 having a first end 652, a second end 654, and a hole 656 extending from first end 652 to second end 654. Plug 650 may be made from any suitable material, including casein, polyurethane, silicone, and polytetrafluoroethylene. Wire 660 has been slidably inserted into hole 656 of plug 650. Wire 660 may be, for example, a guide wire or a pacing lead, so long as it extends through the hole in the cardiac tissue (not shown). As shown in FIG. 12A, first end 652 is covered with a radiopaque material, such as barium sulfate, and is therefore radiopaque. This enables the clinician to view the placement of the plug in the body using radiographic imaging. For example, the clinician can confirm the location of the plug during the procedure, enabling a safer and more effective procedure for the patient.

As shown in FIG. 12A, first end 652 of plug 650 has a smaller diameter than second end 654 of plug 650. Indeed, plug 680 shown FIG. 12B and plug 684 shown in FIGS. 13 and 14 have first ends that are smaller in diameter than their respective second ends. However, not all embodiments of plug have a first end that is smaller in diameter than the second end. For example, plug 682 shown in FIG. 12C has a first end with a diameter that is not smaller than the diameter of the second end. Both types of plug can be used to close holes in cardiac tissue.

Referring again to FIG. 12A, elongated shaft 670 has a proximal end (not shown), a distal end 672, and a lumen 674 extending from the proximal end to distal end 672. Although no catheter is shown in FIG. 12A, plug 650, wire 660, and shaft 670 are configured for insertion into a lumen of a catheter (see FIG. 14), such as an embodiment of an engagement catheter disclosed herein. Plug 650 and shaft 670 are also configured to be inserted over wire 660 and can slide along wire 660 because each of lumen 656 of plug 650 and lumen 674 of shaft 670 is slightly larger in circumference than wire 660.

Figure 13:
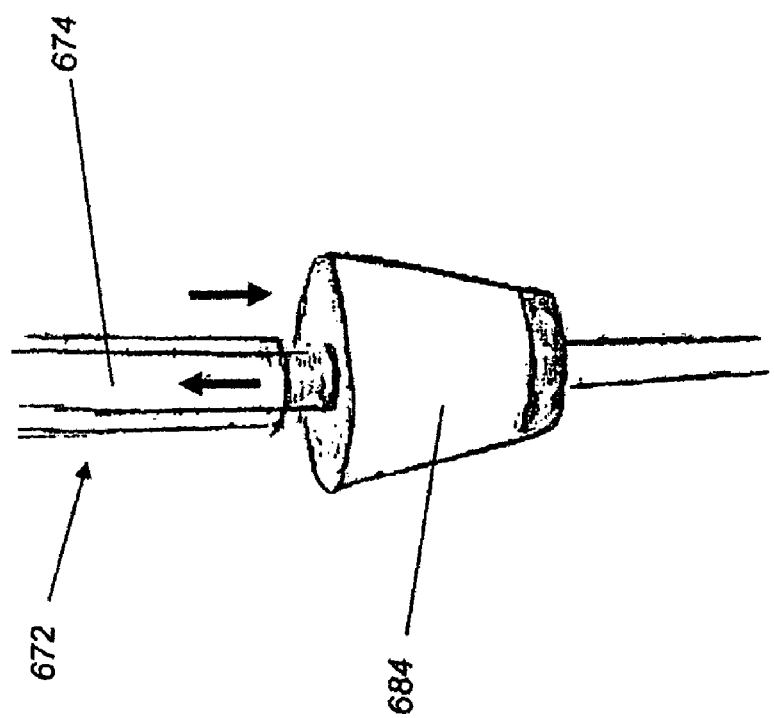
FIG. 13 shows another embodiment of a system for closing a hole in cardiac tissue, as disclosed herein.
Figure 14:
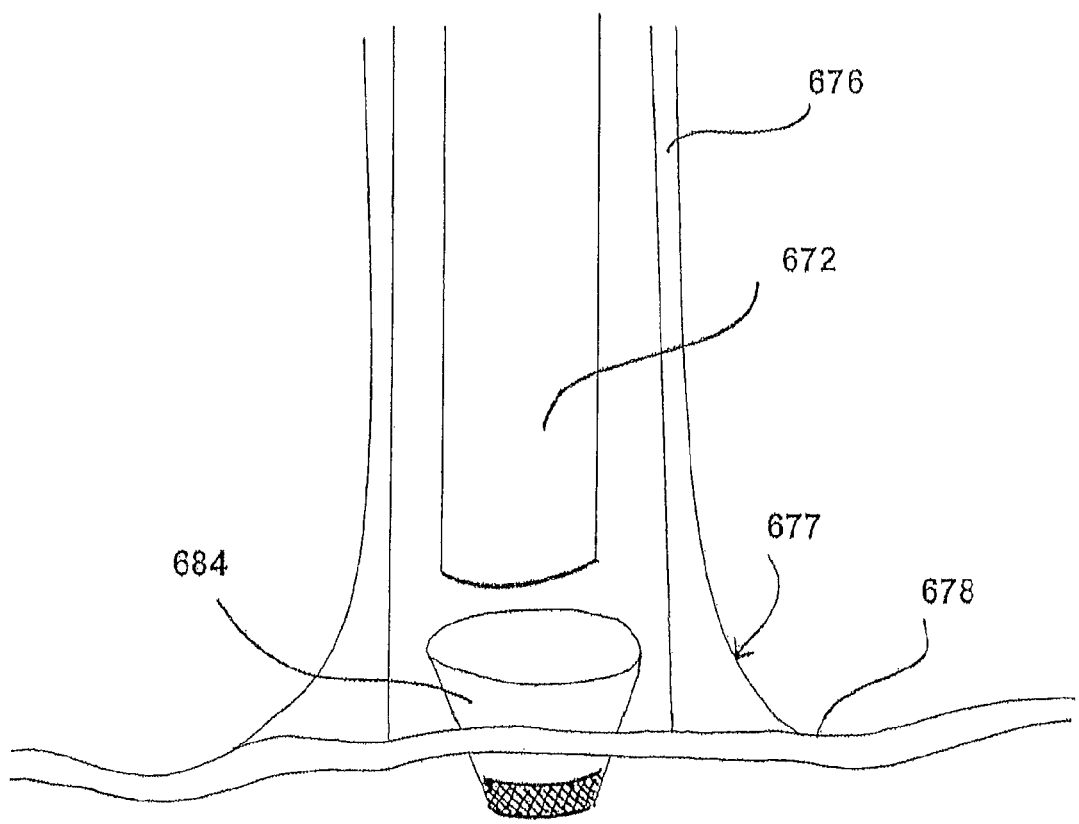
FIG. 14 shows another embodiment of a system for closing a hole in cardiac tissue, as disclosed herein.

As shown in FIGS. 13 and 14, shaft 672 is used to push plug 684 along wire 674 within elongated tube 676 to and into the hole in the targeted cardiac tissue 678. Distal end 677 of elongated tube 676 is shown attached to cardiac tissue 678, but distal end 677 need not be attached to cardiac tissue 678 so long as distal end 677 is adjacent to cardiac tissue 678. Once plug 684 is inserted into the hole, wire 674 may be withdrawn from the hole in plug 684 and the interior of the heart (not shown) and shaft 672 is withdrawn from elongated tube 676. In some embodiments, the plug is self-sealing, meaning that the hole of the plug closes after the wire is withdrawn. For example, the plug may be made from a dehydrated protein matrix, such as casein or ameroid, which swells after soaking up fluid. After shaft 672 is withdrawn, elongated tube 676 can be withdrawn from the heart.

It should be noted that, in some embodiments, the wire is not withdrawn from the hole of the plug. For example, where the wire is a pacing lead, the wire may be left within the plug so that it operatively connects to the CRT device.

Referring now to FIG. 12B, there is shown a plug 680 that is similar to plug 684. However, plug 680 comprises external surface 681 having a ridge 683 that surrounds plug 680 in a helical or screw-like shape. Ridge 683 helps to anchor plug 680 into the hole of the targeted tissue (not shown). Other embodiments of plug may include an external surface having a multiplicity of ridges surrounding the plug, for example, in a circular fashion.

Figure 15A:
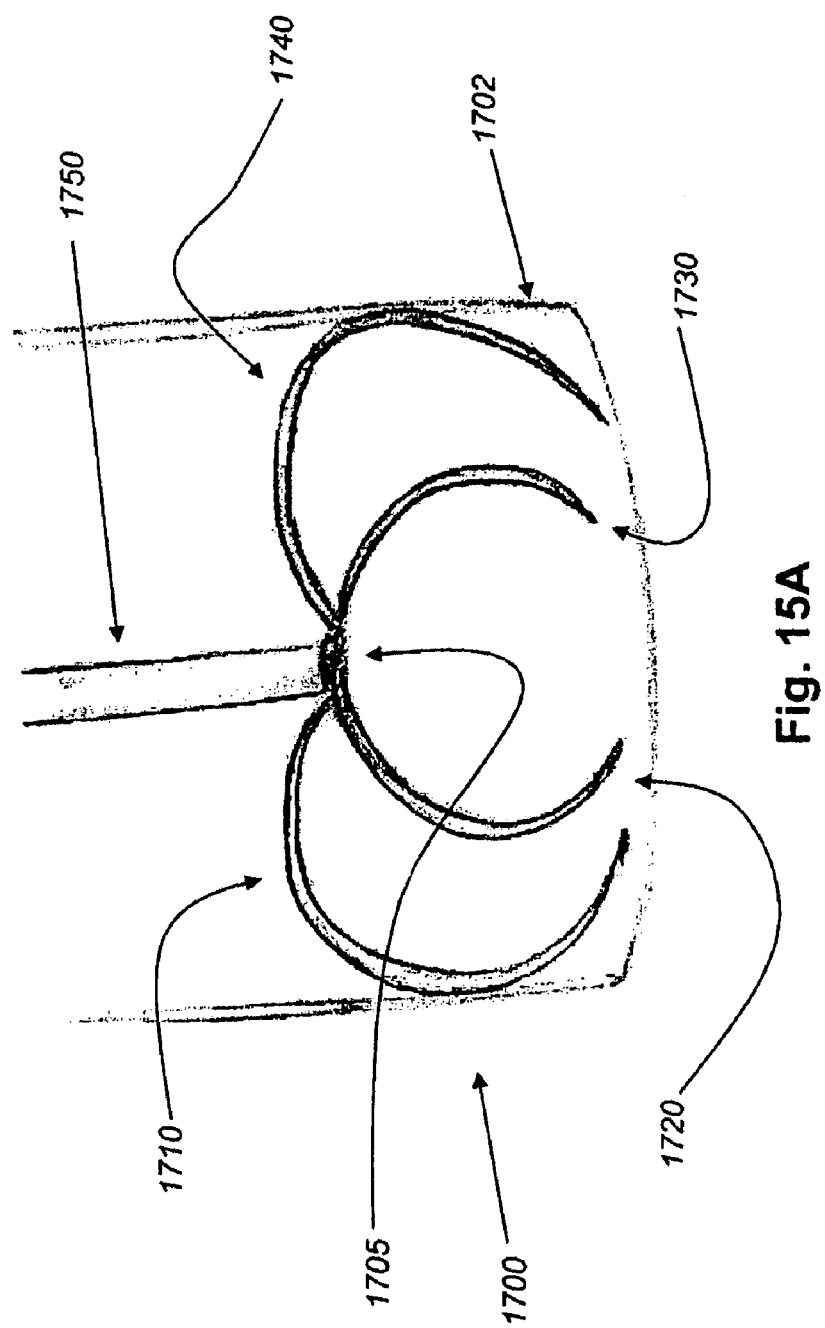
FIG. 15A shows another embodiment of a system for closing a hole in cardiac tissue, as disclosed herein.
Figure 15B:
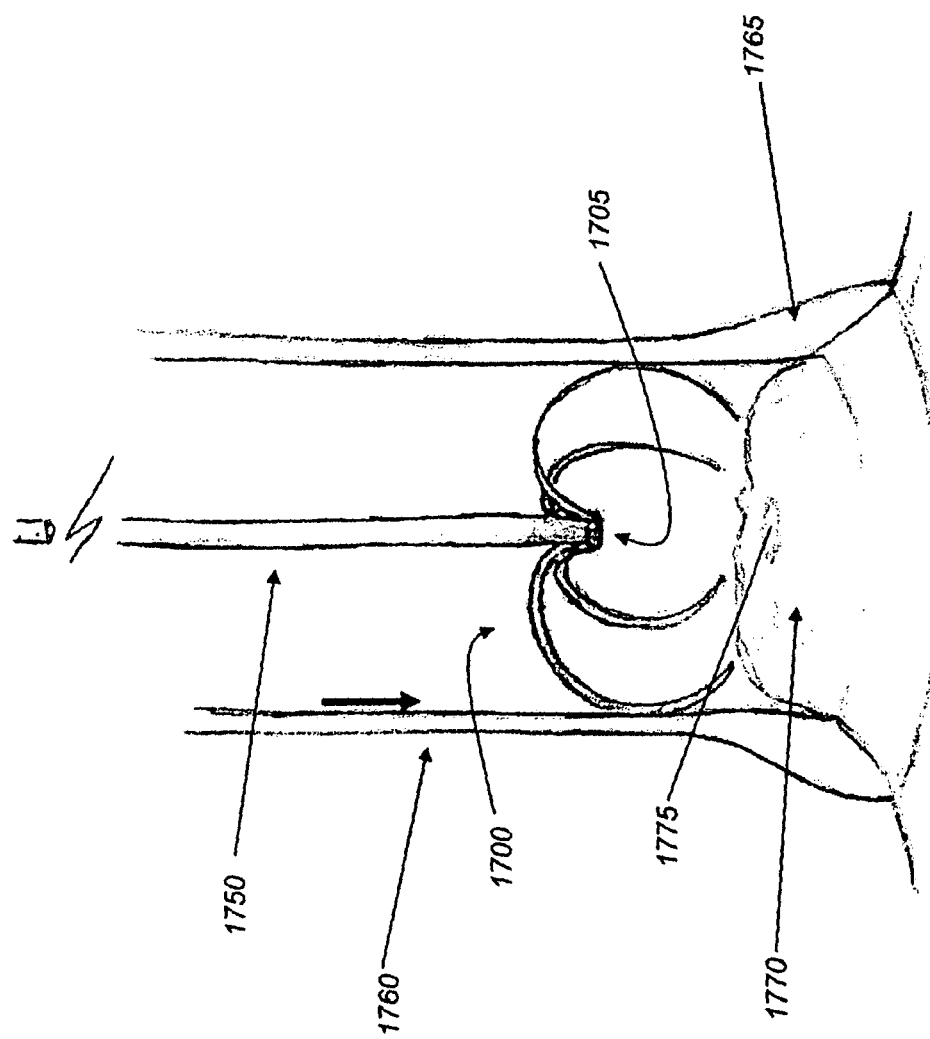
FIG. 15B shows the embodiment of FIG. 15A approaching cardiac tissue.

FIGS. 15A-15C show yet another embodiment of a closure member for closing a hole in a tissue. Spider clip 1700 is shown within catheter 1702 and comprises a head 1705 and a plurality of arms 1710, 1720, 1730, and 1740. Each of arms 1710, 1720, 1730, and 1740 is attached at its proximal end to head 1705. Although spider clip 1700 has four arms, other embodiments of spider clip include fewer than, or more than, four arms. For example, some embodiments of spider clip have three arms, while others have five or more arms.

Referring again to FIGS. 15A-15C, arms 1710, 1720, 1730, and 1740 may be made from any flexible biocompatible metal that can transition between two shapes, such as a shape-memory alloy (e.g., nitinol) or stainless steel. Spider clip 1700 is capable of transitioning between an open position (see FIG. 15A), in which the distal ends of its arms 1710, 1720, 1730, and 1740 are spaced apart, and a closed position (see FIG. 15C), in which the distal ends of arms 1710, 1720, 1730, and 1740 are gathered together. For embodiments made from a shape-memory alloy, the clip can be configured to transition from the open position to the closed position when the metal is warmed to approximately body temperature, such as when the clip is placed into the cardiac tissue. For embodiments made from other types of metal, such as stainless steel, the clip is configured in its closed position, but may be transitioned into an open position when pressure is exerted on the head of the clip. Such pressure causes the arms to bulge outward, thereby causing the distal ends of the arms to separate.

In this way, spider clip 1700 may be used to seal a wound or hole in a tissue, such as a hole through the atrial wall. For example, FIG. 15B shows spider clip 1700 engaged by rod 1750 within engagement catheter 1760. As shown, engagement catheter 1760 has a bell-shaped suction port 1765, which, as disclosed herein, has aspirated cardiac tissue 1770. Cardiac tissue 1770 includes a hole 1775 therethrough, and suction port 1765 fits over hole 1775 so as to expose hole 1775 to spider clip 1700.

Rod 1750 pushes spider clip 1700 through engagement catheter 1760 to advance spider clip 1700 toward cardiac tissue 1770. Rod 1750 simply engages head 1705 by pushing against it, but in other embodiments, the rod may be reversibly attached to the head using a screw-type system. In such embodiments, the rod may be attached and detached from the head simply by screwing the rod into, or unscrewing the rod out of, the head, respectively.

In at least some embodiments, the spider clip is held in its open position during advancement through the engagement catheter by the pressure exerted on the head of the clip by the rod. This pressure may be opposed by the biasing of the legs against the engagement catheter during advancement.

Referring to FIG. 15C, spider clip 1700 approaches cardiac tissue 1770 and eventually engages cardiac tissue 1770 such that the distal end of each of arms 1710, 1720, 1730, and 1740 contacts cardiac tissue 1670. Rod 1750 is disengaged from spider clip 1700, and spider clip 1700 transitions to its closed position, thereby drawing the distal ends of arms 1710, 1720, 1730, and 1740 together. As the distal ends of the arms are drawn together, the distal ends grip portions of cardiac tissue 1770, thereby collapsing the tissue between arms 1710, 1720, 1730, and 1740 such that hole 1775 is effectively closed.

Rod 1750 is then withdrawn, and engagement catheter 1760 is disengaged from cardiac tissue 1770. The constriction of cardiac tissue 1770 holds hole 1775 closed so that blood does not leak through hole 1775 after engagement catheter 1760 is removed. After a relatively short time, the body's natural healing processes permanently close hole 1775. Spider clip 1700 may remain in the body indefinitely.

Figure 16A:
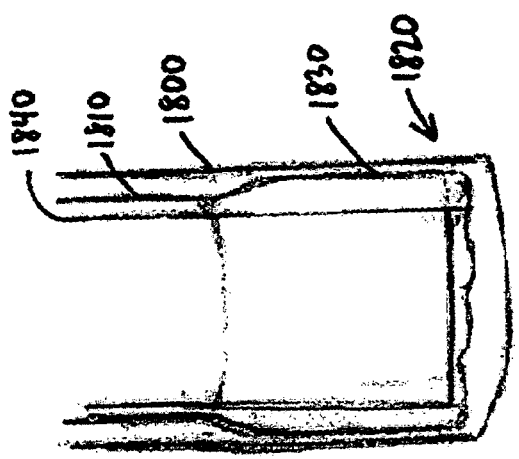
FIG. 16A shows an embodiment of a portion of an apparatus for engaging a tissue having a skirt positioned substantially within a sleeve, as disclosed herein.
Figure 16B:
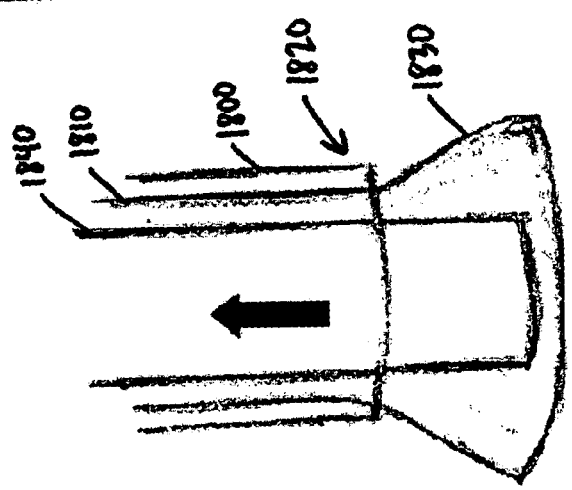
FIG. 16B shows another embodiment of a portion of an apparatus for engaging a tissue, as disclosed herein.
Figure 16C:
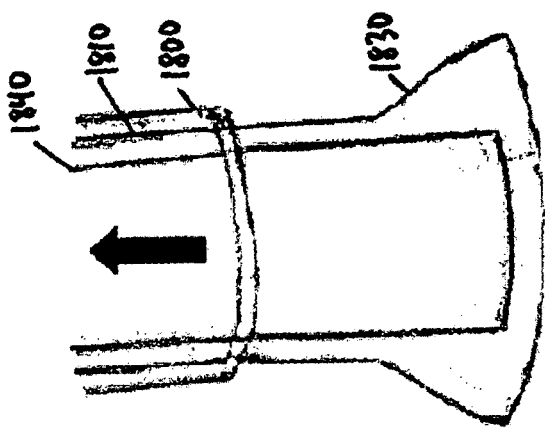
FIG. 16C shows an embodiment of a portion of an apparatus for engaging a tissue having a skirt positioned substantially outside of a sleeve, as disclosed herein.

FIGS. 16A, 16B, and 16C show an embodiment of a portion of an apparatus for engaging a tissue as disclosed herein. As shown in FIG. 16A, a sleeve 1800 is present around at least a portion of an engagement catheter 1810. Sleeve 1800, as described herein, may comprise a rigid or flexible tube having a lumen therethrough, appearing around the outside of engagement catheter 1810 and slidingly engaging engagement catheter 1810. In at least the embodiment shown in FIG. 16A, the distal end 1820 of engagement catheter 1810 comprises a skirt 1830, shown in FIG. 16A as being housed within sleeve 1800. A delivery catheter 1840 may be present within engagement catheter 1810 as shown to facilitate the delivery of a product (gas, liquid, and/or particulate(s)) to a target site. In this embodiment, delivery catheter 1840 is present at least partially within the lumen of engagement catheter 1810, and engagement catheter is placed at least partially within the lumen of sleeve 1800.

Referring now to FIG. 16B, an embodiment of an apparatus as shown in FIG. 16A or similar to the embodiment shown in FIG. 16A is shown with sleeve 1800 being "pulled back" from the distal end of engagement catheter 1810. As shown in FIG. 16B, as sleeve 1800 is pulled back (in the direction of the arrow), skirt 1830 becomes exposed, and as sleeve 1800 is no longer present around skirt 1830, skirt 1830 may optionally expand into a frusto-conical ("bell-shaped") skirt 1830. Skirt 1830 may be reversibly deformed (collapsed) when present within the lumen of sleeve 1800 as shown in FIG. 16A and in FIG. 18A described in further detail herein. It can be appreciated that many alternative configurations of skirt 1830 to the frusto-conical configuration may exist, including an irregular frusto-conical configuration, noting that a configuration of skirt 1830 having a distal portion (closest to a tissue to be engaged) larger than a proximal position may benefit from suction of a larger surface area of a tissue as described in further detail herein.

FIG. 16C shows an embodiment of an apparatus described herein having an expanded skirt 1830. As shown in FIG. 16C, sleeve 1800 has been pulled back (in the direction of the arrow) so that the expanded configuration of skirt 1830 may be present to engage a tissue (not shown).

FIGS. 17A and 17B shown alternative embodiments of a portion of an apparatus for engaging a tissue as described herein. FIGS. 17A and 17B each show a sleeve 1800, an engagement catheter 1810 having a skirt 1830, and a delivery catheter 1840. In each figure, skirt 1830 is shown engaging a surface of a tissue 1850. In the embodiments shown in FIGS. 17A and 17B, the relative sizes of the sleeves 1800, engagement catheters 1810, and delivery catheters 1840 are similar as shown, but the relative sizes of the skirts 1830 of the engagement catheters 1810 are clearly different. The exemplary embodiment of the portion of an apparatus for engaging a tissue shown in FIG. 17A comprises a skirt 1830 of the same or substantially similar relative size as the engagement catheter 1810, meaning that the diameters of the engagement catheter 1810 and the skirt 1830 shown in FIG. 17A are approximately the same. Conversely, the exemplary embodiment of the portion of an apparatus for engaging a tissue shown in FIG. 17B comprises a skirt 1830 notably larger than the engagement catheter 1810, meaning that the diameters of the engagement catheter 1810 and the skirt 1830 at its widest point shown in FIG. 17B are notably different. As shown in FIG. 17B, as skirt 1830 extends from engagement catheter 1810 to tissue 1850, the diameter of skirt 1830 increases. As such, skirt 1830 of the embodiment shown in FIG. 17B may engage a larger surface area of a tissue (shown by 1860) than the embodiment of the skirt 1830 shown in FIG. 17A. The ability to engage a larger surface area of a tissue 1850 by skirt 1830 allows a better reversible engagement of a tissue 1850 when a vacuum is provided as described in detail herein. This improved suction allows a person using such an apparatus to more effectively engage a tissue 1850 than would otherwise be possible when skirt 1830 engages a smaller surface area of a tissue.

FIGS. 18A and 18B show perspective views of an embodiment of a portion of an apparatus for engaging a tissue. FIG. 18A represents an embodiment whereby a skirt 1830 of an engagement catheter 1810 is positioned substantially within a sleeve 1800. FIG. 18B represents an embodiment whereby a skirt 1830 of an engagement catheter 1810 is positioned outside of s 1800. As such, the positioning of skirt 1830 within sleeve 1800 can be seen in the embodiments of FIGS. 16A and 18A, and the positioning of skirt 1830 outside of sleeve 1800 can be seen in the embodiments of FIGS. 16C and 18B.

As shown in FIG. 18A, skirt 1830 of engagement catheter 1810 is positioned within sleeve 1800, whereby the configuration of skirt 1830 is collapsed so that skirt 1830 may fit within sleeve 1800. As sleeve 1800 moves in the direction of the arrow shown in FIG. 18B, skirt 1830 becomes exposed and its configuration is allowed to expand because there are no constraints provided by the inner wall of sleeve 1800.

The embodiments shown in FIGS. 18A and 18B also show an exemplary embodiment of a configuration of an engagement catheter 1810. As shown in FIG. 18B, engagement catheter 1810 defines a number of apertures (representing lumens) present at the distal end of engagement catheter 1810 (at the proximal end of skirt 1830), including, but not limited to, one or more vacuum ports 1870 (representing the aperture at or near the distal end of a vacuum tube), and a delivery port 1880 (representing the aperture at or near the distal end of a delivery tube). A vacuum source (not shown) may be coupled to a suction port located at a proximal end of one or more vacuum tubes as described herein, whereby gas, fluid, and/or particulate(s) may be introduced into one or more vacuum ports 1870 by the introduction of a vacuum at a vacuum port. Gas, fluid, and/or particulate(s) may be introduced from delivery aperture 1880 to a tissue (not shown in FIGS. 18A or 18B).

As shown by the exemplary embodiments of FIGS. 17A and 17B, the ability for a user of such an apparatus for engaging a tissue to obtain proper suction depends at least in part on the relative placement of skirt 1830 and delivery catheter 1840 at or near a tissue 1850. As described in detail herein regarding the exemplary embodiment shown in FIG. 5D, if a vacuum source provides suction through one or more vacuum ports 1870 (shown in FIGS. 18A and 18B), but skirt 1830 has not effectively engaged a tissue 1850, gas, fluid, and/or particulate(s) in the area of tissue 1850 and/or gas, fluid and/or particulate(s) delivered via delivery catheter 1840 to the area of tissue 1850 may be aspirated by one or more vacuum ports 1870. In a situation where skirt 1830 has effectively engaged a tissue 1850 but where delivery catheter 1840 has not engaged a tissue 1850, any gas, liquid, and/or particulate(s) delivered by delivery catheter 1840 may be aspirated by one or more vacuum ports 1870. In a situation where skirt 1830 and delivery catheter 1840 have effectively engaged a tissue 1850, most, if not all, of any gas, liquid, and/or particulate(s) delivered by delivery catheter 1840 to tissue 1850 would not be aspirated by one or more vacuum ports 1870 as the placement of delivery catheter 1840 on or within tissue 1850 would provide direct delivery at or within tissue 1850.

Figure 19:
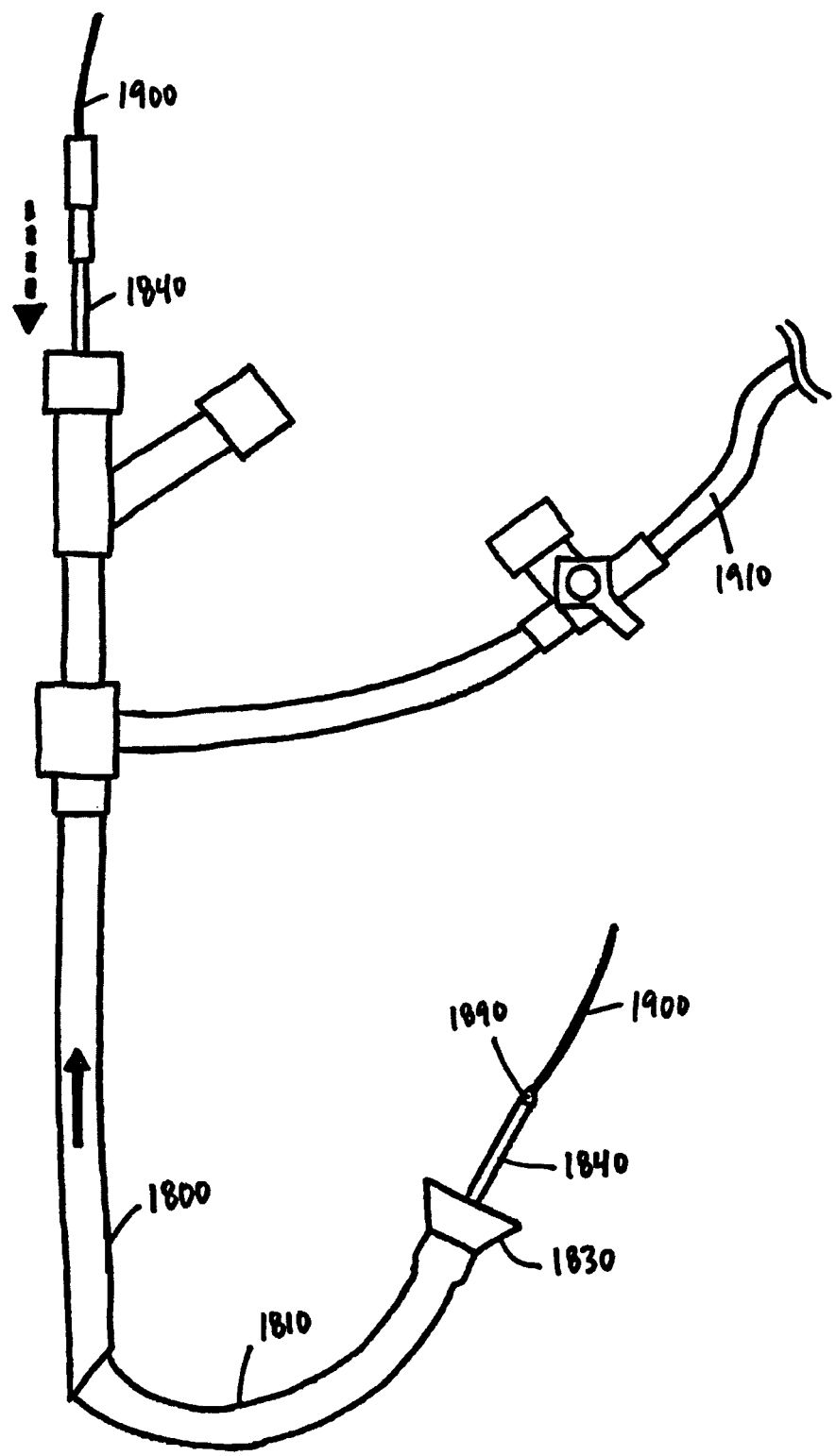
FIG. 19 shows an embodiment of a system for engaging a tissue, as disclosed herein.

An exemplary embodiment of a system and/or device for engaging a tissue as described herein is shown in FIG. 19. As shown in FIG. 19, an exemplary apparatus shows a sleeve 1800 which has been moved in the direction of the arrow to reveal skirt 1830 at the distal end of engagement catheter 1810, allowing skirt to resume an expanded, frusto-conical configuration. As shown in this embodiment, delivery catheter 1840 has been introduced at the proximal end of the apparatus (in the direction shown by the dashed arrow), allowing delivery catheter 1840 to exit out of a delivery lumen (not shown) at the distal end of engagement catheter 1840. A needle 1890 may be present at the distal end of delivery catheter 1840, facilitating the potential puncture of a tissue (not shown) to allow the distal end of delivery catheter 1840 to enter a tissue.

In addition, and as shown in the exemplary embodiment of FIG. 19, a lead 1900 may be introduced into delivery catheter 1840 (in the direction shown by the dashed arrow), whereby the distal end of lead 1900 may exit an aperture of needle 1890 and optionally enter a tissue and/or a lumen of a tissue. As described herein, any number of suitable types of leads 1900 may be used with the delivery catheters described herein, including sensing leads and/or pacing leads. A vacuum source 1910 may also provide a source of vacuum to such an apparatus to allow skirt 1830 to engage a tissue using suction.

The exemplary embodiment of an apparatus for engaging a tissue as shown in FIG. 19 comprises an engagement catheter 1810 having a curvature. Such a curved engagement catheter 1810 allows a user of such an apparatus, for example, to insert a portion of the apparatus into a body or tissue from one direction, and engage a tissue with skirt 1830, delivery catheter 1840, needle 1890, and/or lead 1900 from another direction. For example, a user may introduce a portion of an apparatus from one side of the heart, and the apparatus may engage the heart from a different direction than the direction of introduction of the apparatus.

It can also be appreciated that an exemplary embodiment of an apparatus of the present disclosure may be used to engage an internal portion of an organ. As previously referenced herein, such an apparatus may be used to engage the surface of a tissue. However, it can be appreciated that such a tissue may be an outer surface of any number of tissues, including, but not limited to, a heart, lungs, intestine, stomach, or any number of other organs or tissues. It can also be appreciated that some of these types of organs or tissues, including the heart for example, may have one or more internal tissue surfaces capable of being engaged by an apparatus of the present disclosure. For example, a user of such an apparatus may use the apparatus to engage the septum of the heart dividing one side of the heart from another. Such use may facilitate the delivery of a gas, liquid, and/or particulate(s) to a particular side of the heart, as such a targeted delivery may provide beneficial effects, including, but not limited to, the ability to deliver a lead to pace the inner wall of the left side of the heart.

Referring now to FIGS. 20A, 20B, and 20C, embodiments of a portion of an apparatus for engaging a tissue according to the present disclosure are shown. As shown in FIG. 20A, an exemplary embodiment of a portion of an apparatus for engaging a tissue comprises sleeve 1800 slidingly engaging engagement catheter 1810, and when sleeve 1800 is slid in the direction of the arrow shown, skirt 1830 is revealed, having an expanded, optionally frusto-conical configuration as shown. Delivery catheter 1840 may exit out of a delivery lumen (not shown), with needle 1890 present at the distal end of delivery catheter 1840. As shown in the embodiment of FIG. 20A, lead 1900 is present, exiting out of an aperture of needle 1890.

FIGS. 20B and 20C show a closer view of an embodiment of a portion of an apparatus for engaging a tissue according to the present disclosure than is shown in FIG. 20A. As shown in FIGS. 20B and 20C, aperture 1920 of needle 1890 is shown, and as shown in FIG. 20C, lead 1900 may exit aperture 1920 of needle 1890.

Referring now to FIGS. 5A, 5B, 5C, and 5D, there is shown another embodiment of an engagement catheter as disclosed herein. Engagement catheter 700 is an elongated tube having a proximal end 710 and a distal end 720, as well as two lumens 730, 740 extending between proximal end 710 and distal end 720. Lumens 730, 740 are formed by concentric inner wall 750 and outer wall 760, as particularly shown in FIGS. 5B and 5C. At proximal end 710, engagement catheter 700 includes a vacuum port 770, which is attached to lumen 730 so that a vacuum source can be attached to vacuum port 770 to create suction in lumen 730, thereby forming a suction channel. At distal end 720 of catheter 700, a suction port 780 is attached to lumen 730 so that suction port 780 can be placed in contact with heart tissue 775 (see FIG. 5D) for aspirating the tissue, thereby forming a vacuum seal between suction port 780 and tissue 775 when the vacuum source is attached and engaged. The vacuum seal enables suction port 780 to grip, stabilize, and retract tissue 775. For example, attaching a suction port to an interior atrial wall using a vacuum source enables the suction port to retract the atrial wall from the pericardial sac surrounding the heart, which enlarges the pericardial space between the atrial wall and the pericardial sac.

As shown in FIG. 5C, two internal lumen supports 810, 820 are located within lumen 730 and are attached to inner wall 750 and outer wall 760 to provide support to the walls. These lumen supports divide lumen 730 into two suction channels. Although internal lumen supports 810, 820 extend from distal end 720 of catheter 700 along a substantial portion of the length of catheter 700, internal lumen supports 810, 820 may or may not span the entire length of catheter 700. Indeed, as shown in FIGS. 5A, 5B, and 5C, internal lumen supports 810, 820 do not extend to proximal end 710 to ensure that the suction from the external vacuum source is distributed relatively evenly around the circumference of catheter 700. Although the embodiment shown in FIG. 5C includes two internal lumen supports, other embodiments may have just one internal support or even three or more such supports.

Figure 5D:
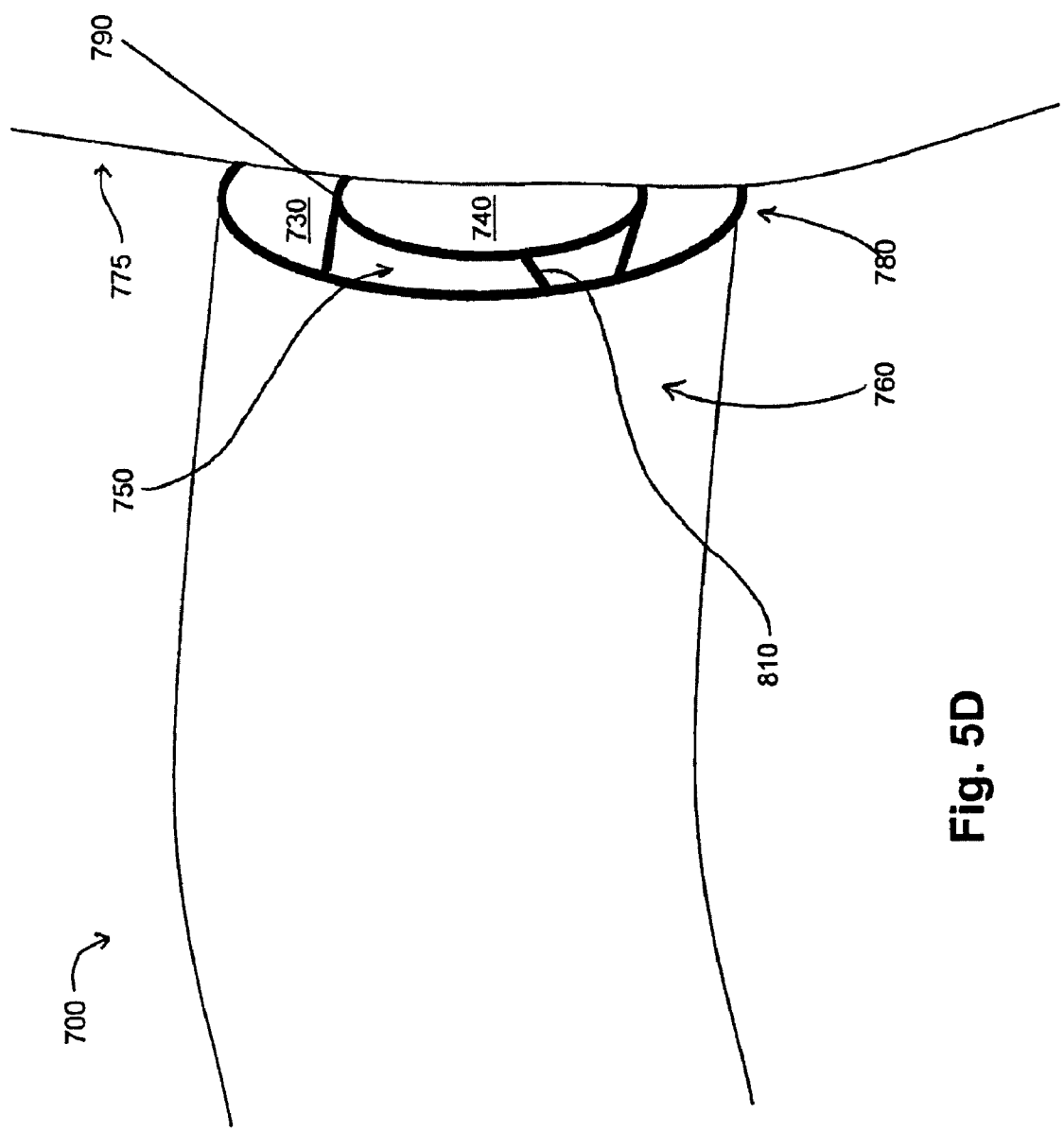
FIG. 5D shows the engagement catheter shown in FIG. 5A approaching a heart wall from inside of the heart.

FIG. 5D shows engagement catheter 700 approaching heart tissue 775 for attachment thereto. It is important for the clinician performing the procedure to know when the suction port has engaged the tissue of the atrial wall or the atrial appendage. For example, in reference to FIG. 5D, it is clear that suction port 780 has not fully engaged tissue 775 such that a seal is formed. However, because suction port 780 is not usually seen during the procedure, the clinician may determine when the proper vacuum seal between the atrial tissue and the suction port has been made by monitoring the amount of blood that is aspirated, by monitoring the suction pressure with a pressure sensor/regulator, or both. For example, as engagement catheter 700 approaches the atrial wall tissue (such as tissue 775) and is approximately in position, the suction can be activated through lumen 730. A certain level of suction (e.g., 10 mmHg) can be imposed and measured with a pressure sensor/regulator. As long as catheter 700 does not engage the wall, some blood will be aspirated into the catheter and the suction pressure will remain the same. However, when catheter 700 engages or attaches to the wall of the heart (depicted as tissue 775 in FIG. 5D), minimal blood is aspirated and the suction pressure will start to gradually increase. Each of these signs can alert the clinician (through alarm or other means) as an indication of engagement. The pressure regulator is then able to maintain the suction pressure at a preset value to prevent over-suction of the tissue.

An engagement catheter, such as engagement catheter 700, may be configured to deliver a fluid or other substance to tissue on the inside of a wall of the heart, including an atrial wall or a ventricle wall. For example, lumen 740 shown in FIGS. 5A and 5C includes an injection channel 790 at distal end 720. Injection channel 790 dispenses to the targeted tissue a substance flowing through lumen 740. As shown in FIG. 5D, injection channel 790 is the distal end of lumen 740. However, in other embodiments, the injection channel may be ring-shaped (see FIG. 2C) or have some other suitable configuration.

Substances that can be locally administered with an engagement catheter include preparations for gene or cell therapy, drugs, and adhesives that are safe for use in the heart. The proximal end of lumen 740 has a fluid port 800, which is capable of attachment to an external fluid source for supply of the fluid to be delivered to the targeted tissue. Indeed, after withdrawal of a needle from the targeted tissue, as discussed herein, an adhesive may be administered to the targeted tissue by the engagement catheter for sealing the puncture wound left by the needle withdrawn from the targeted tissue.

Referring now to FIGS. 6A, 6B, and 6C, there is shown a delivery catheter 850 comprising an elongated hollow tube 880 having a proximal end 860, a distal end 870, and a lumen 885 along the length of the catheter. Extending from distal end 870 is a hollow needle 890 in communication with lumen 885. Needle 890 is attached to distal end 870 in the embodiment of FIGS. 6A, 6B, and 6C, but, in other embodiments, the needle may be removably attached to, or otherwise located at, the distal end of the catheter (see FIG. 1A). In the embodiment shown in FIGS. 6A, 6B, and 6C, as in certain other embodiments having an attached needle, the junction (i.e., site of attachment) between hollow tube 880 and needle 890 forms a security notch 910 circumferentially around needle 890 to prevent needle 890 from over-perforation. Thus, when a clinician inserts needle 890 through an atrial wall to gain access to the pericardial space, the clinician will not, under normal conditions, unintentionally perforate the pericardial sac with needle 890 because the larger diameter of hollow tube 880 (as compared to that of needle 890) at security notch 910 hinders further needle insertion. Although security notch 910 is formed by the junction of hollow tube 880 and needle 890 in the embodiment shown in FIGS. 6A, 6B, and 6C, other embodiments may have a security notch that is configured differently. For example, a security notch may include a band, ring, or similar device that is attached to the needle a suitable distance from the tip of the needle. Like security notch 910, other security notch embodiments hinder insertion of the needle past the notch itself by presenting a larger profile than the profile of the needle such that the notch does not easily enter the hole in the tissue caused by entry of the needle.

It is useful for the clinician performing the procedure to know when the needle has punctured the atrial tissue. This can be done in several ways. For example, the delivery catheter can be connected to a pressure transducer to measure pressure at the tip of the needle. Because the pressure is lower and much less pulsatile in the pericardial space than in the atrium, the clinician can recognize immediately when the needle passes through the atrial tissue into the pericardial space.

Alternatively, as shown in FIG. 6B, needle 890 may be connected to a strain gauge 915 as part of the catheter assembly. When needle 890 contacts tissue (not shown), needle 890 will be deformed. The deformation will be transmitted to strain gauge 915 and an electrical signal will reflect the deformation (through a classical wheatstone bridge), thereby alerting the clinician. Such confirmation of the puncture of the wall can prevent over-puncture and can provide additional control of the procedure.

In some embodiments, a delivery catheter, such as catheter 850 shown in FIGS. 6A, 6B, and 6C, is used with an engagement catheter, such as catheter 700 shown in FIGS. 5A, 5B, 5C, and 5D, to gain access to the pericardial space between the heart wall and the pericardial sac. For example, engagement catheter 700 may be inserted into the vascular system and advanced such that the distal end of the engagement catheter is within the atrium. The engagement catheter may be attached to the targeted tissue on the interior of a wall of the atrium using a suction port as disclosed herein. A standard guide wire may be inserted through the lumen of the delivery catheter as the delivery catheter is inserted through the inner lumen of the engagement catheter, such as lumen 740 shown in FIGS. 5B and 5C. Use of the guide wire enables more effective navigation of the delivery catheter 850 and prevents the needle 890 from damaging the inner wall 750 of the engagement catheter 700. When the tip of the delivery catheter with the protruding guide wire reaches the atrium, the wire is pulled back, and the needle is pushed forward to perforate the targeted tissue. The guide wire is then advanced through the perforation into the pericardial space, providing access to the pericardial space through the atrial wall.

Referring again to FIGS. 6A, 6B, and 6C, lumen 885 of delivery catheter 850 may be used for delivering fluid into the pericardial space after needle 890 is inserted through the atrial wall or the atrial appendage. After puncture of the wall or appendage, a guide wire (not shown) may be inserted through needle lumen 900 into the pericardial space to maintain access through the atrial wall or appendage. Fluid may then be introduced to the pericardial space in a number of ways. For example, after the needle punctures the atrial wall or appendage, the needle is generally withdrawn. If the needle is permanently attached to the delivery catheter, as in the embodiment shown in FIGS. 6A and 6B, then delivery catheter 850 would be withdrawn and another delivery catheter (without an attached needle) would be introduced over the guide wire into the pericardial space. Fluid may then be introduced into the pericardial space through the lumen of the second delivery catheter.

In some embodiments, however, only a single delivery catheter is used. In such embodiments, the needle is not attached to the delivery catheter, but instead may be a needle wire (see FIG. 1A). In such embodiments, the needle is withdrawn through the lumen of the delivery catheter, and the delivery catheter may be inserted over the guide wire into the pericardial space. Fluid is then introduced into the pericardial space through the lumen of the delivery catheter.

The various embodiments disclosed herein may be used by clinicians, for example: (1) to deliver genes, cells, drugs, etc.; (2) to provide catheter access for epicardial stimulation; (3) to evacuate fluids acutely (e.g., in cases of pericardial tampondae) or chronically (e.g., to alleviate effusion caused by chronic renal disease, cancer, etc.); (4) to perform transeptal puncture and delivery of a catheter through the left atrial appendage for electrophysiological therapy, biopsy, etc.; (5) to deliver a magnetic glue or ring through the right atrial appendage to the aortic root to hold a percutaneous aortic valve in place; (6) to deliver a catheter for tissue ablation, e.g., to the pulmonary veins, or right atrial and epicardial surface of the heart for atrial and ventricular arrythmias; (7) to deliver and place epicardial, right atrial, and right and left ventricle pacing leads (as discussed herein); (8) to occlude the left atrial appendage through percutaneous approach; and (9) to visualize the pericardial space with endo-camera or scope to navigate the epicardial surface of the heart for therapeutic delivery, diagnosis, lead placement, mapping, etc. Many other applications, not explicitly listed here, are also possible and within the scope of the present disclosure.

Figure 7:
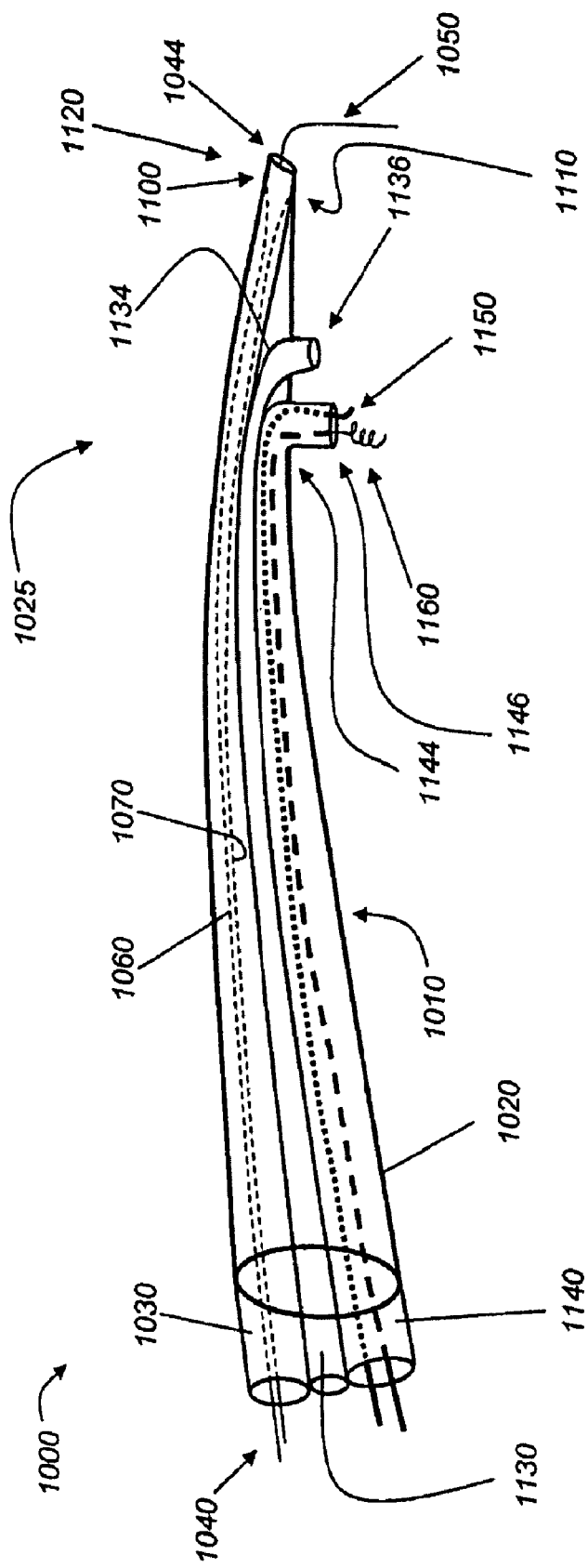
FIG. 7 shows an embodiment of a delivery catheter as disclosed herein.

Referring now to FIG. 7, there is shown a delivery catheter 1000. Delivery catheter 1000 includes an elongated tube 1010 having a wall 1020 extending from a proximal end (not shown) of tube 1010 to a distal end 1025 of tube 1010. Tube 1010 includes two lumens, but other embodiments of delivery catheters may have fewer than, or more than, two lumens, depending on the intended use of the delivery catheter. Tube 1010 also includes a steering channel 1030, in which a portion of steering wire system 1040 is located. Steering channel 1030 forms orifice 1044 at distal end 1025 of tube 1010 and is sized to fit over a guide wire 1050.

Figure 8:
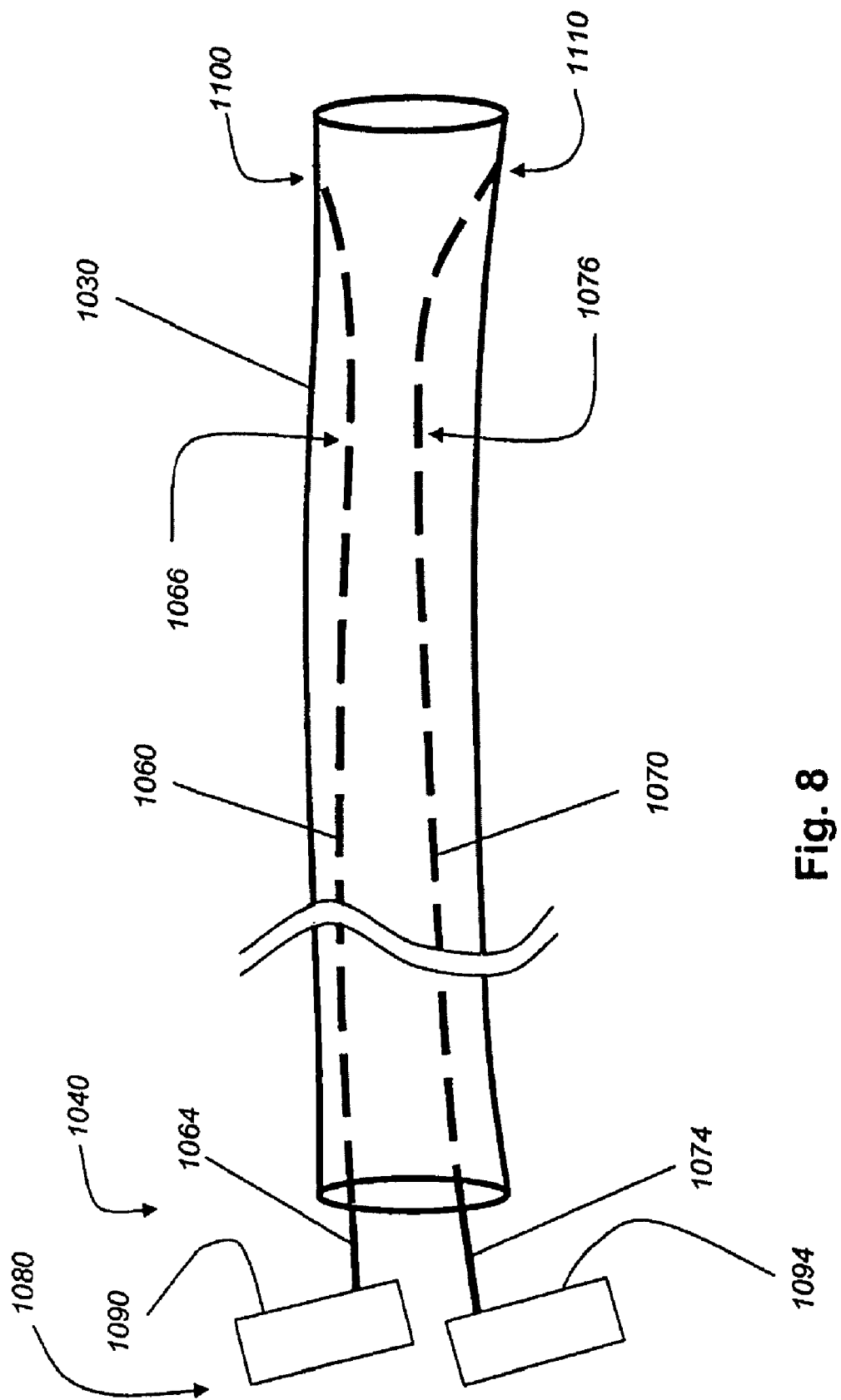
FIG. 8 shows an embodiment of a steering wire system within a steering channel.

FIG. 8 shows in more detail steering wire system 1040 within steering channel 1030 (which is shown cut away from the remainder of the delivery catheter). Steering wire system 1040 is partially located in steering channel 1030 and comprises two steering wires 1060 and 1070 and a controller 1080, which, in the embodiment shown in FIG. 8, comprises a first handle 1090 and a second handle 1094. First handle 1090 is attached to proximal end 1064 of steering wire 1060, and second handle 1094 is attached to proximal end 1074 of steering wire 1070. Distal end 1066 of steering wire 1060 is attached to the wall of the tube of the delivery catheter within steering channel 1030 at attachment 1100, and distal end 1076 of steering wire 1070 is attached to the wall of the tube of the delivery catheter within steering channel 1030 at attachment 1110. As shown in FIG. 7, attachment 1100 and attachment 1110 are located on opposing sides of steering channel 1030 near distal tip 1120 of delivery catheter 1000.

Figure 11:
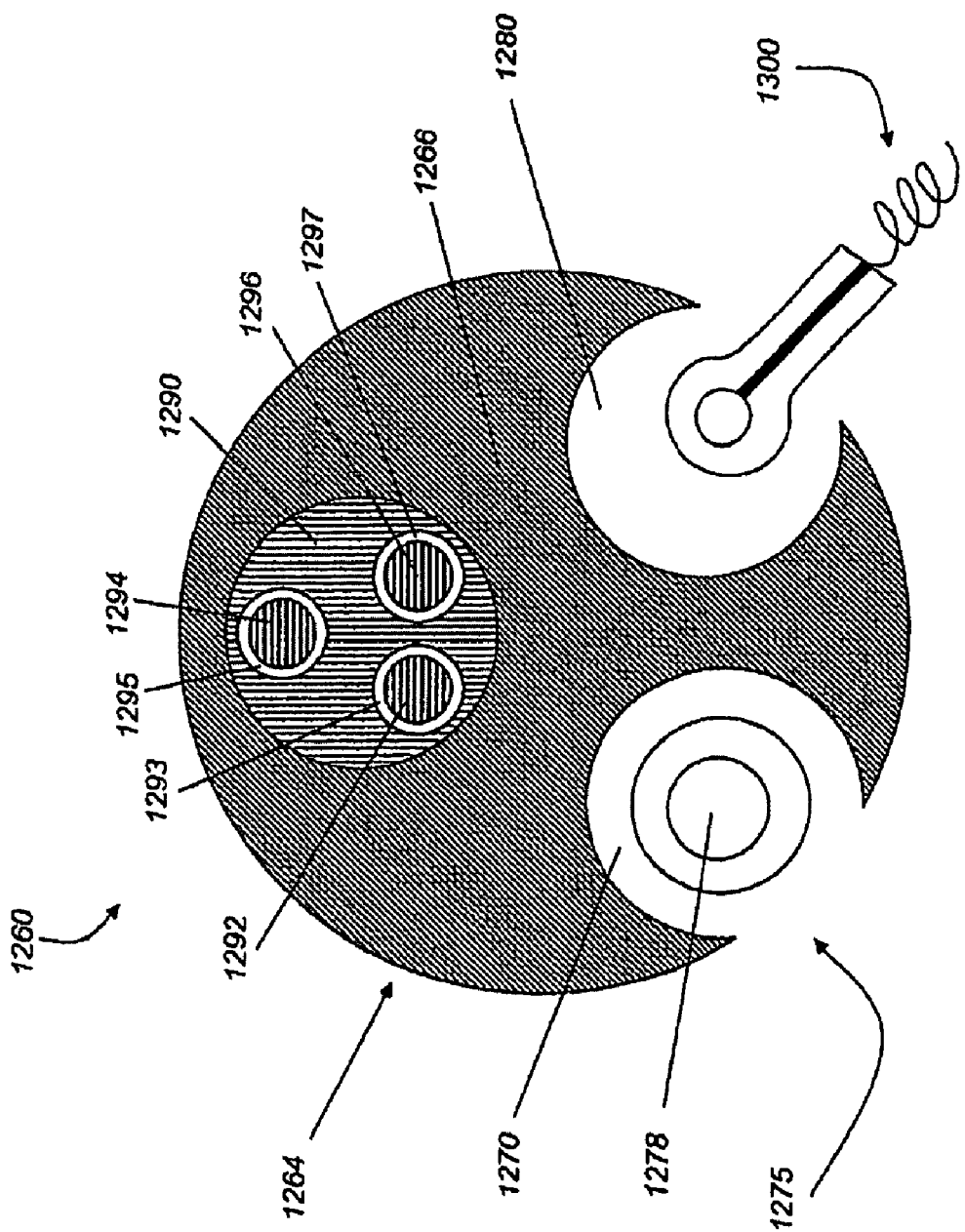
FIG. 11 shows a cross-sectional view of another embodiment of a delivery catheter as disclosed herein.
Figure 12:
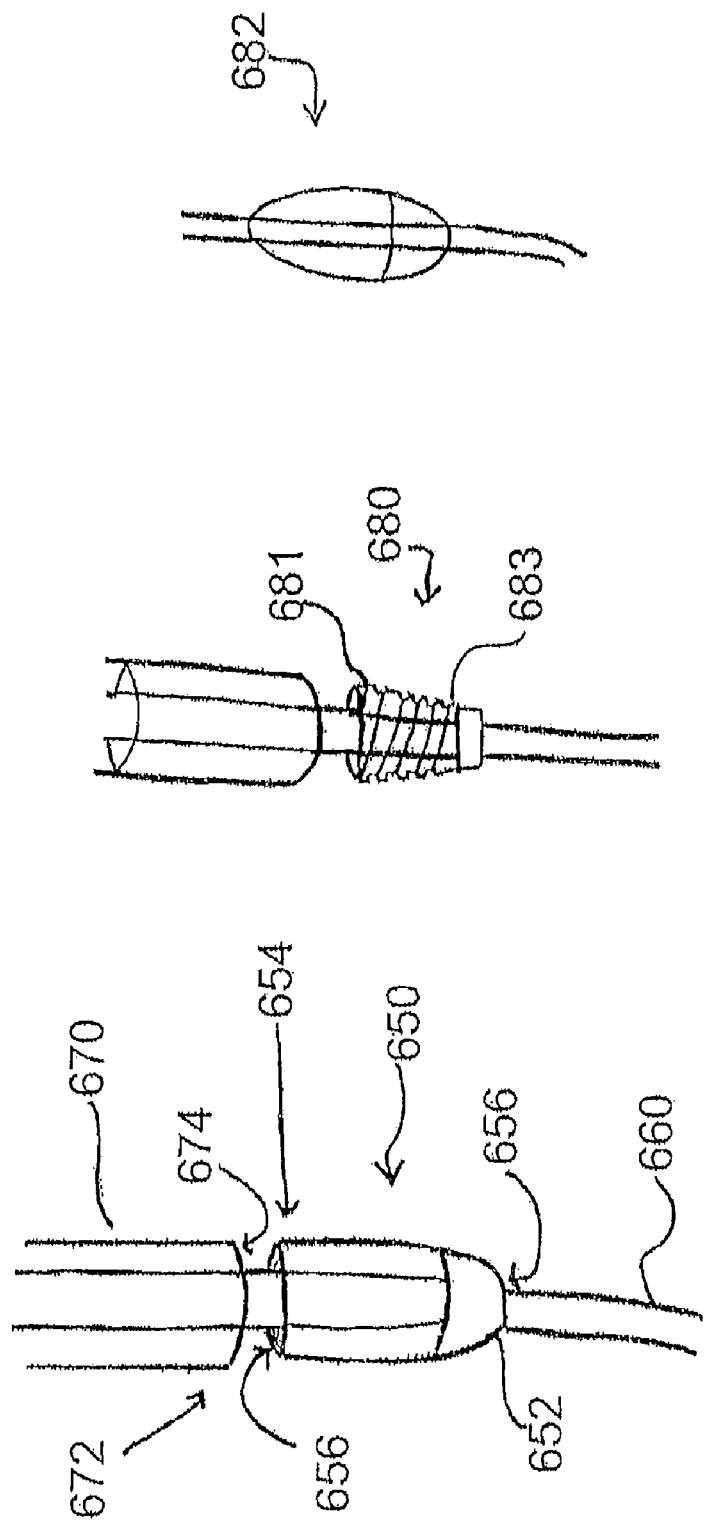
FIG. 12A shows an embodiment of a system for closing a hole in cardiac tissue, as disclosed herein.
FIG. 12B shows another embodiment of a system for closing a hole in cardiac tissue, as disclosed herein.
FIG. 12C shows another embodiment of a system for closing a hole in cardiac tissue, as disclosed herein.

In the embodiment of FIG. 8, steering wires 1060 and 1070 are threaded as a group through steering channel 1030. However, the steering wire systems of other embodiments may include steering wires that are individually threaded through smaller lumens within the steering channel. For example, FIG. 11 shows a cross-sectional view of a delivery catheter 1260 having an elongated tube 1264 comprising a wall 1266, a steering channel 1290, a first lumen 1270, and a second lumen 1280. Delivery catheter 1260 further includes a steering wire 1292 within a steering wire lumen 1293, a steering wire 1294 within a steering wire lumen 1295, and a steering wire 1296 within a steering wire lumen 1297. Each of steering wire lumens 1293, 1295, and 1297 is located within steering channel 1290 and is formed from wall 1266. Each of steering wires 1292, 1294, and 1296 is attached to wall 1266 within steering channel 1290. As will be explained, the attachment of each steering wire to the wall may be located near the distal tip of the delivery catheter, or may be located closer to the middle of the delivery catheter.

Referring now to FIGS. 7 and 8, steering wire system 1040 can be used to control distal tip 1120 of delivery catheter 1000. For example, when first handle 1090 is pulled, steering wire 1060 pulls distal tip 1120, which bends delivery catheter 1000, causing tip deflection in a first direction. Similarly, when second handle 1094 is pulled, steering wire 1070 pulls distal tip 1120 in the opposite direction, which bends delivery catheter 1000, causing tip deflection in the opposite direction. Thus, delivery catheter 1000 can be directed (i.e., steered) through the body using steering wire system 1040.

Although steering wire system 1040 has only two steering wires, other embodiments of steering wire systems may have more than two steering wires. For example, some embodiments of steering wire systems may have three steering wires (see FIG. 11), each of which is attached to the steering channel at a different attachment. Other embodiments of steering wire systems may have four steering wires. Generally, more steering wires give the clinician more control for directing the delivery catheter because each additional steering wire enables the user to deflect the tip of the delivery catheter in an additional direction. For example, four steering wires could be used to direct the delivery catheter in four different directions (e.g., up, down, right, and left).

If a steering wire system includes more than two steering wires, the delivery catheter may be deflected at different points in the same direction. For instance, a delivery catheter with three steering wires may include two steering wires for deflection in a certain direction and a third steering wire for reverse deflection (i.e., deflection in the opposite direction). In such an embodiment, the two steering wires for deflection are attached at different locations along the length of the delivery catheter. Referring now to FIGS. 9A-9C, there is shown a steering wire system 1350 within steering channel 1360 (which is shown cut away from the remainder of the delivery catheter) in different states of deflection. Steering wire system 1350 is partially located in steering channel 1360 and comprises three steering wires 1370, 1380, and 1390 and a controller 1400, which, in the embodiment shown in FIGS. 9A-9C, comprises a handle 1410. Handle 1410 is attached to proximal end 1374 of steering wire 1370, proximal end 1384 of steering wire 1380, and proximal end 1394 of steering wire 1390. Distal end 1376 of steering wire 1370 is attached to the wall of the tube of the delivery catheter within steering channel 1360 at attachment 1378, which is near the distal tip of the delivery catheter (not shown). Distal end 1386 of steering wire 1380 is attached to the wall of the tube of the delivery catheter within steering channel 1360 at attachment 1388, which is near the distal tip of the delivery catheter (not shown). Attachment 1378 and attachment 1388 are located on opposing sides of steering channel 1360 such that steering wires 1370 and 1380, when tightened (as explained below), would tend to deflect the delivery catheter in opposite directions. Distal end 1396 of steering wire 1390 is attached to the wall of the tube of the delivery catheter within steering channel 1360 at attachment 1398, which is located on the delivery catheter at a point closer to the proximal end of the delivery catheter than attachments 1378 and 1388. Attachment 1398 is located on the same side of steering channel 1360 as attachment 1388, such that steering wires 1380 and 1390, when tightened (as explained below), would tend to deflect the delivery catheter in the same direction. However, because attachment 1398 is closer to the proximal end of the delivery catheter than is attachment 1388, the tightening of steering wire 1390 tends to deflect the delivery catheter at a point closer to the proximal end of the delivery catheter than does the tightening of steering wire 1380. Thus, as shown in FIG. 9A, the tightening of steering wire 1390 causes a deflection in the delivery catheter approximately at point 1410. The tightening of steering wire 1380 at the same time causes a further deflection in the delivery catheter approximately at point 1420, as shown in FIG. 9B. The tightening of steering wire 1370, therefore, causes a reverse deflection, returning the delivery catheter to its original position (see FIG. 9C).

Referring again to FIG. 7, elongated tube 1010 further includes lumen 1130 and lumen 1140. Lumen 1130 extends from approximately the proximal end (not shown) of tube 1010 to or near distal end 1025 of tube 1010. Lumen 1130 has a bend 1134, relative to tube 1010, at or near distal end 1025 of tube 1010 and an outlet 1136 through wall 1020 of tube 1010 at or near distal end 1025 of tube 1010. Similarly, lumen 1140 has a bend 1144, relative to tube 1010, at or near distal end 1025 of tube 1010 and an outlet 1146 through wall 1020 of tube 1010 at or near distal end 1025 of tube 1010. In the embodiment shown in FIG. 7, lumen 1130 is configured as a laser Doppler tip, and lumen 1140 is sized to accept a retractable sensing lead 1150 and a pacing lead 1160 having a tip at the distal end of the lead. The fiberoptic laser Doppler tip detects and measures blood flow (by measuring the change in wavelength of light emitted by the tip), which helps the clinician to identify—and then avoid—blood vessels during lead placement. Sensing lead 1150 is designed to detect electrical signals in the heart tissue so that the clinician can avoid placing a pacing lead into electrically nonresponsive tissue, such as scar tissue. Pacing lead 1160 is a screw-type lead for placement onto the cardiac tissue, and its tip, which is an electrode, has a substantially screw-like shape. Pacing lead 1160 is capable of operative attachment to a CRT device (not shown) for heart pacing. Although lead 1160 is used for cardiac pacing, any suitable types of leads may be used with the delivery catheters described herein, including sensing leads.

Each of bend 1134 of lumen 1130 and bend 1144 of lumen 1140 forms an approximately 90-degree angle, which allows respective outlets 1136 and 1146 to face the external surface of the heart as the catheter is maneuvered in the pericardial space. However, other embodiments may have bends forming other angles, smaller or larger than 90-degrees, so long as the lumen provides proper access to the external surface of the heart from the pericardial space. Such angles may range, for example, from about 25-degrees to about 155-degrees. In addition to delivering leads and Doppler tips, lumen 1130 and lumen 1140 may be configured to allow, for example, the taking of a cardiac biopsy, the delivery of gene cell treatment or pharmacological agents, the delivery of biological glue for ventricular reinforcement, implementation of ventricular epicardial suction in the acute myocardial infarction and border zone area, the removal of fluid in treatment of pericardial effusion or cardiac tamponade, or the ablation of cardiac tissue in treatment of atrial fibrillation.

For example, lumen 1130 could be used to deliver a catheter needle for intramyocardial injection of gene cells, stems, biomaterials, growth factors (such as cytokinase, fibroblast growth factor, or vascular endothelial growth factor) and/or biodegradable synthetic polymers, RGD-liposome biologic glue, or any other suitable drug or substance for treatment or diagnosis. For example, suitable biodegradable synthetic polymer may include polylactides, polyglycolides, polycaprolactones, polyanhydrides, polyamides, and polyurethanes. In certain embodiments, the substance comprises a tissue inhibitor, such as a metalloproteinase (e.g., metalloproteinase 1).

The injection of certain substances (such as biopolymers and RGD-liposome biologic glue) is useful in the treatment of chronic heart failure to reinforce and strengthen the left ventricular wall. Thus, using the embodiments disclosed herein, the injection of such substances into the cardiac tissue from the pericardial space alleviates the problems and risks associated with delivery via the transthoracic approach. For instance, once the distal end of the delivery catheter is advanced to the pericardial space, as disclosed herein, a needle is extended through a lumen of the delivery catheter into the cardiac tissue and the substance is injected through the needle into the cardiac tissue.

The delivery of substances into the cardiac tissue from the pericardial space can be facilitated using a laser Doppler tip. For example, when treating ventricular wall thinning, the laser Doppler tip located in lumen 1140 of the embodiment shown in FIG. 7 can be used to measure the thickness of the left ventricular wall during the procedure (in real time) to determine the appropriate target area for injection.

Figure 10:
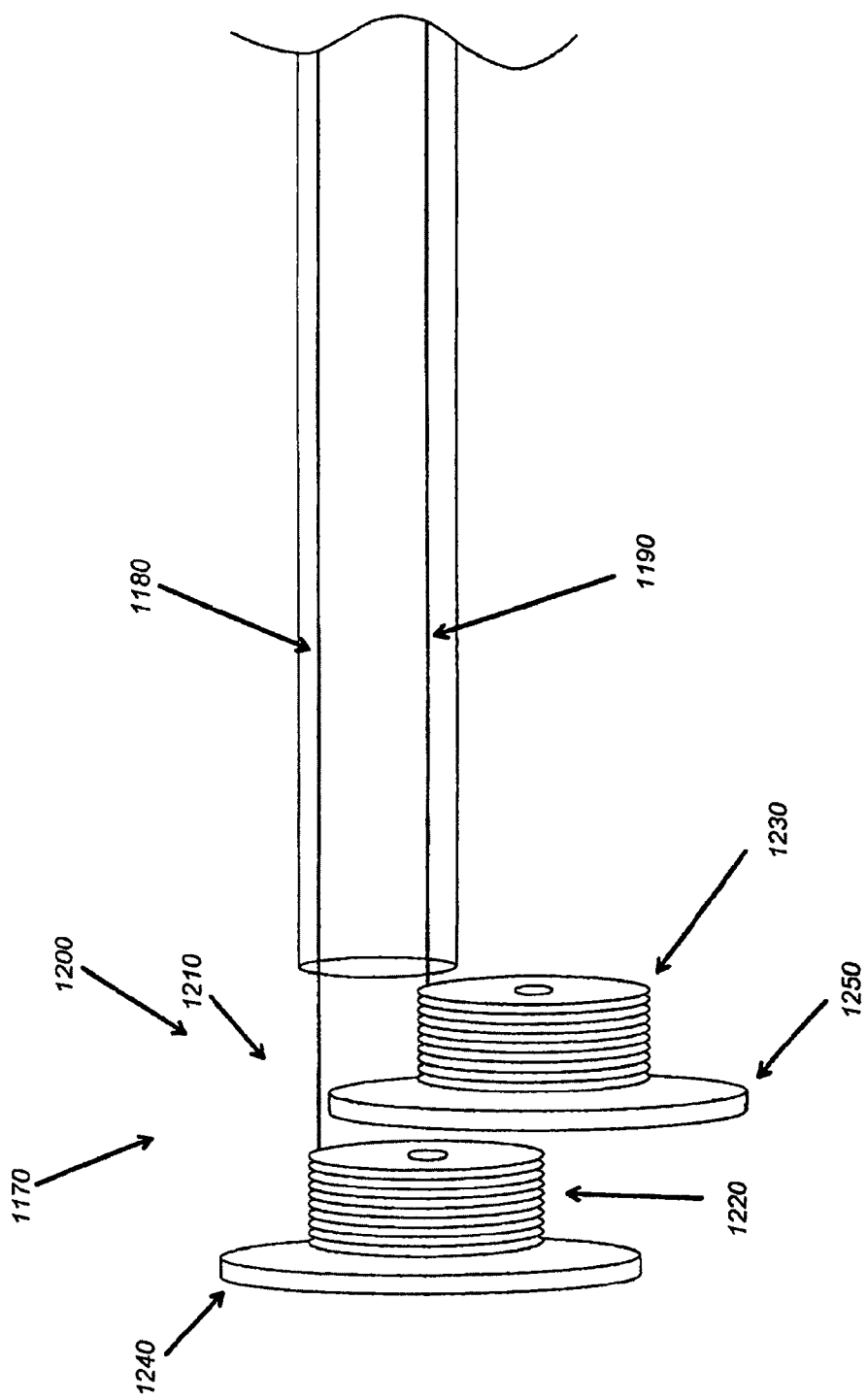
FIG. 10 shows a portion of another embodiment of a steering wire system.

Referring again to FIG. 8, although controller 1080 comprises first handle 1090 and second handle 1094, other embodiments of the controller may include different configurations. For example, instead of using handles, a controller may include any suitable torque system for controlling the steering wires of the steering wire system. Referring now to FIG. 10, there is shown a portion of a steering wire system 1170 having steering wire 1180, steering wire 1190, and controller 1200. Controller 1200 comprises a torque system 1210 having a first rotatable spool 1220, which is capable of collecting and dispensing steering wire 1180 upon rotation. For example, when first rotatable spool 1220 rotates in a certain direction, steering wire 1180 is collected onto spool 1220, thereby tightening steering wire 1180. When spool 1220 rotates in the opposite direction, steering wire 1180 is dispensed from spool 1220, thereby loosening steering wire 1180. Torque system 1210 also has a second rotatable spool 1230, which is capable of collecting and dispensing steering wire 1190 upon rotation, as described above.

Torque system 1210 further includes a first rotatable dial 1240 and a second rotatable dial 1250. First rotatable dial 1240 is attached to first rotatable spool 1220 such that rotation of first rotatable dial 1240 causes rotation of first rotatable spool 1220. Similarly, second rotatable dial 1250 is attached to second rotatable spool 1230 such that rotation of second rotatable dial 1250 causes rotation of second rotatable spool 1230. For ease of manipulation of the catheter, torque system 1210, and specifically first and second rotatable dials 1240 and 1250, may optionally be positioned on a catheter handle (not shown) at the proximal end of tube 1010.

Steering wire system 1170 can be used to direct a delivery catheter through the body in a similar fashion as steering wire system 1140. Thus, for example, when first rotatable dial 1240 is rotated in a first direction (e.g., clockwise), steering wire 1180 is tightened and the delivery catheter is deflected in a certain direction. When first rotatable dial 1240 is rotated in the other direction (e.g., counterclockwise), steering wire 1180 is loosened and the delivery catheter straightens to its original position. When second rotatable dial 1250 is rotated in one direction (e.g., counterclockwise), steering wire 1190 is tightened and the delivery catheter is deflected in a direction opposite of the first deflection. When second rotatable dial 1250 is rotated in the other direction (e.g., clockwise), steering wire 1190 is loosened and the delivery catheter is straightened to its original position.

Certain other embodiments of steering wire system may comprise other types of torque system, so long as the torque system permits the clinician to reliably tighten and loosen the various steering wires. The magnitude of tightening and loosening of each steering wire should be controllable by the torque system.

Referring again to FIG. 11, there is shown a cross-sectional view of delivery catheter 1260. Delivery catheter 1260 includes tube 1265, a first lumen 1270, a second lumen 1280, and a steering channel 1290. Steering wires 1292, 1294, and 1296 are shown within steering channel 1290. First lumen 1270 has outlet 1275, which can be used to deliver a microcamera system (not shown) or a laser Doppler tip 1278. Second lumen 1280 is sized to deliver a pacing lead 1300, as well as a sensing lead (not shown).

Treatment of cardiac tamponade, by the removal of a pericardial effusion, may be accomplished using an apparatus of the present disclosure as described below. A typical procedure would involve the percutaneous intravascular insertion of a portion of an apparatus into a body, which can be performed under local or general anesthesia. A portion of the apparatus may then utilize an approach described herein or otherwise known by a user of the apparatus to enter the percutaneous intravascular pericardial sac. It can be appreciated that such an apparatus may be used to access other spaces within a body to remove fluid and/or deliver a gas, liquid, and/or particulate(s) as described herein, and that such an apparatus is not limited to heart access and removal of pericardial effusions.

Exemplary embodiments of a portion of such an apparatus are shown in FIGS. 21A and 21B. As shown in FIG. 21A, a perforated drainage catheter 2100 is provided. Perforated drainage catheter 2100 comprises a tube defining at least one suction/injection aperture 2110, and as shown in the embodiment in FIG. 21A, perforated drainage catheter 2100 defines multiple suction/injection apertures 2110. Suction/injection apertures 2110 are operably connected to an internal lumen defined within perforated delivery catheter 2100. It can be appreciated that the portion of perforated drainage catheter 2100 as shown in FIGS. 21A and 21B may be coupled to one or more portions of a system for engaging a tissue as described herein. As such, one or more portions of a system for engaging a tissue may be used to define a system for removing fluid as described herein.

It can be appreciated that the internal lumen within perforated delivery catheter 2100 may define multiple internal channels. For example, perforated delivery catheter 2100 may define two channels, one channel operably coupled to one or more suction/injection apertures 2110 to allow for a vacuum source coupled to one end of the channel to provide suction via the suction/injection apertures 2110, and one channel operably coupled to one or more other suction/injection channels to allow for the injection of gas, liquid, and/or particulate(s) to a target site.

As described in further detail below, when perforated drainage catheter 2100 enters a space in a body, for example a pericardial sac, perforated drainage catheter 2100 may be used to remove fluid by the use of suction through one or more suction/injection apertures 2110. Perforated drainage catheter 2100 may also be used to deliver gas, liquid, and/or particulate(s) to a target site through one or more suction/injection apertures 2110.

Another exemplary embodiment of a portion of a perforated drainage catheter 2100 is shown in FIG. 21B. As shown in FIG. 21B, perforated drainage catheter 2100 comprises a tube with multiple suction/injection apertures 2110. However, in this exemplary embodiment, perforated drainage catheter 2100 comprises a number of concave grooves 2120 extending a portion of a length of perforated drainage catheter 2100, whereby the suction/injection apertures 2110 are provided at the recessed portions therein. Concave grooves 2120, when positioned at least partially around the circumference of perforated drainage catheter 2100, define one or more ridges 2130 extending a portion of a length of perforated drainage catheter 2100. Said ridges 2130 of perforated drainage catheter 2100, when positioned at or near a tissue (not shown), aid to prevent a tissue from coming in direct contact with one or more suction/injection apertures 2110. For example, when perforated drainage catheter 2100 is used in a manner described herein and when a vacuum is coupled to perforated drainage catheter 2100, suction from one or more suction/injection apertures 2110 positioned within one or more concave grooves 2120 would allow for the removal of fluid present in the area of perforated drainage catheter 2100. Ridges 2130 would aid to prevent or minimize tissue adhesion and/or contact with the one or more suction/injection apertures 2110.

A procedure using perforated drainage catheter 2100 may be performed by inserting perforated drainage catheter 2100 into a pericardial sac, following the cardiac surface using, for example, fluoroscopy and/or echodoppler visualization techniques. When perforated drainage catheter 2100 is inserted into a pericardial sac, a pericardial effusion present within the pericardial sac, may be removed by, for example, gentle suction using a syringe. In one example, a 60 cc syringe may be used to remove the effusion with manual gentle suction. When the effusion has been removed, the patients hemodynamic parameters may be monitored to determine the effectiveness of the removal of the effusion. When the pericardial sac is empty, determined by, for example, fluoroscopy or echodoppler visualization, the acute pericardial effusion catheter may be removed, or it may be used for local treatment to introduce, for example, an antibiotic, chemotherapy, or another drug as described below.

Figure 22:
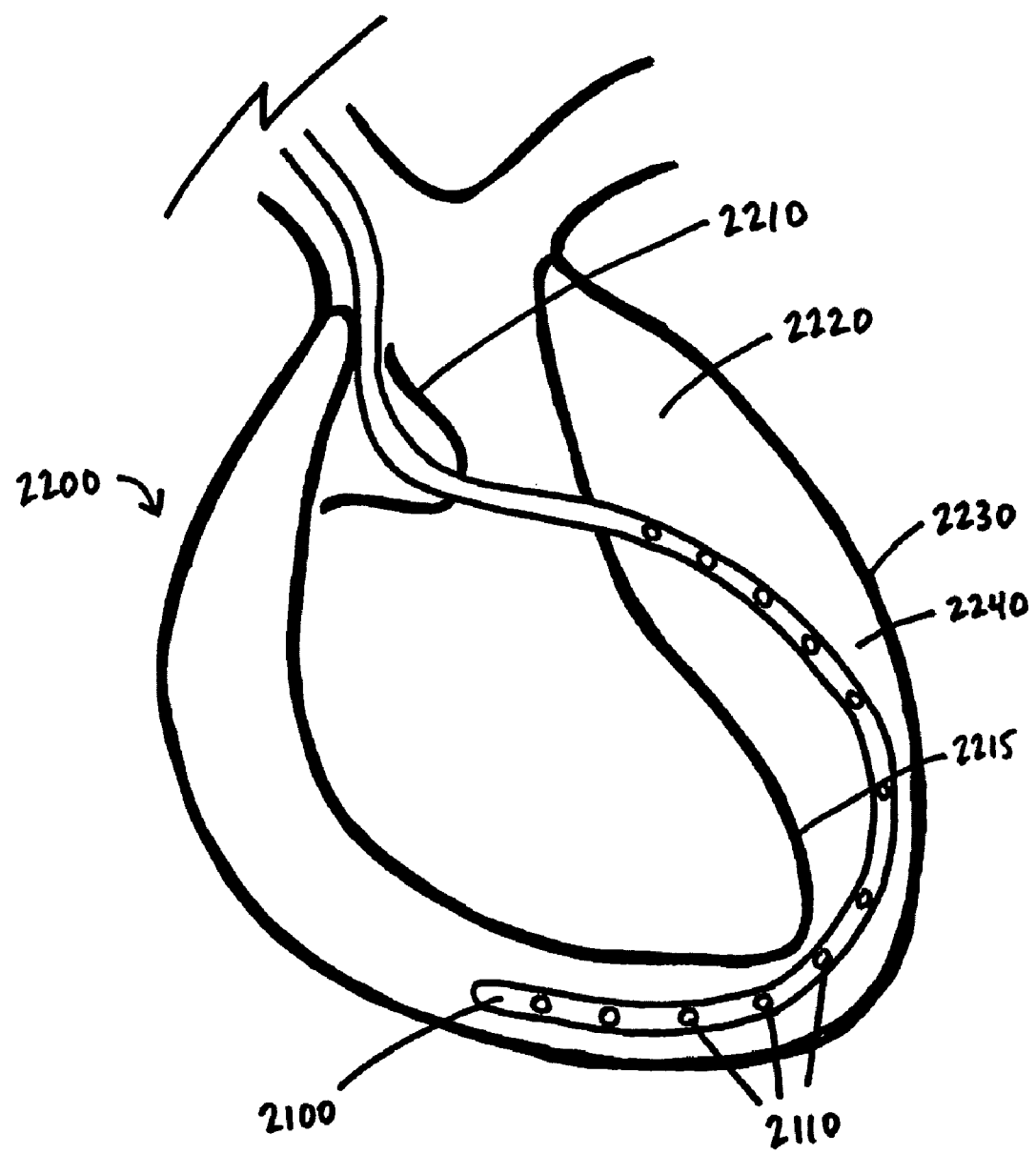
FIG. 22 shows an embodiment of a portion of an apparatus for removing fluid from a tissue inserted within a heart, as disclosed herein.

An exemplary embodiment of a portion of a perforated drainage catheter 2100 present within a pericardial sac is shown in FIG. 22. As shown in FIG. 22, perforated drainage catheter 2100 is first inserted into the heart 2200 using one or more of the techniques and/or procedures described herein, and is placed through the right atrial appendage 2210, the visceral pericardium 2215, and into the pericardial sac 2220. The outer portion of the pericardial sac 2220 is defined by the parietal pericardium 2230. A pericardial effusion 2240 (fluid within the pericardial sac 2220) may then be removed using perforated drainage catheter 2100. When a vacuum source (not shown) is coupled to the proximal end of a portion of a system for removing fluid (comprising, in part, perforated drainage catheter 2100 and one or more other components of a system for engaging a tissue as described herein), the introduction of a vacuum to perforated drainage catheter 2100 allows the pericardial effusion 2240 (the fluid) to be withdrawn from the pericardial sac 2220 into one or more suction/injection apertures 2110 defined along a length of suction/injection apertures 2110.

When perforated drainage catheter 2100 is used to remove some or all of a pericardial effusion (or other fluid present within a space within a body), it may also be used to deliver a gas, liquid, and/or particulate(s) at or near the space where the fluid was removed. For example, the use of perforated drainage catheter 2100 to remove a pericardial effusion may increase the risk of infection. As such, perforated drainage catheter 2100 may be used to rinse the pericardial sac (or other space present within a body) with water and/or any number of beneficial solutions, and may also be used to deliver one or more antibiotics to provide an effective systemic antibiotic therapy for the patient. While the intrapericardial instillation of antibiotics (e.g., gentamycin) is useful, it is typically not sufficient by itself, and as such, it may be combined with general antibiotics treatment for a more effective treatment.

Additional methods to treat neoplastic pericardial effusions without tamponade may be utilized using a device, system and/or method of the present disclosure. For example, a systemic antineoplastic treatment may be performed to introduce drugs to inhibit and/or prevent the development of tumors. If a non-emergency condition exists (e.g., not a cardiac tamponade), a system and/or method of the present disclosure may be used to perform a pericardiocentesis. In addition, the present disclosure allows for the intrapericardial instillation of a cytostatic/sclerosing agent. It can be appreciated that using one or more of the devices, systems and/or methods disclosed herein, the prevention of recurrences may be achieved by intrapericardial instillation of sclerosing agents, cytotoxic agents, or immunomodulators, noting that the intrapericardial treatment may be tailored to the type of the tumor. Regarding chronic autoreactive pericardial effusions, the intrapericardial instillation of crystalloid glucocorticoids could avoid systemic side effects, while still allowing high local dose application.

A pacing lead may be placed on the external surface of the heart using an engagement catheter and a delivery catheter as disclosed herein. For example, an elongated tube of an engagement catheter is extended into a blood vessel so that the distal end of the tube is in contact with a targeted tissue on the interior of a wall of the heart. As explained above, the targeted tissue may be on the interior of the atrial wall or the atrial appendage. Suction is initiated to aspirate a portion of the targeted tissue to retract the cardiac wall away from the pericardial sac that surrounds the heart, thereby enlarging a pericardial space between the pericardial sac and the cardiac wall. A needle is then inserted through a lumen of the tube and advanced to the heart. The needle is inserted into the targeted tissue, causing a perforation of the targeted tissue. The distal end of a guide wire is inserted through the needle into the pericardial space to secure the point of entry through the cardiac wall. The needle is then withdrawn from the targeted tissue.

A delivery catheter, as described herein, is inserted into the lumen of the tube of the engagement catheter and over the guide wire. The delivery catheter may be a 14 Fr. radiopaque steering catheter. The distal end of the delivery catheter is advanced over the guide wire through the targeted tissue into the pericardial space. Once in the pericardial space, the delivery catheter is directed using a steering wire system as disclosed herein. In addition, a micro-camera system may be extended through the lumen of the delivery catheter to assist in the direction of the delivery catheter to the desired location in the pericardial space. Micro-camera systems suitable for use with the delivery catheter are well-known in the art. Further, a laser Doppler system may be extended through the lumen of the delivery catheter to assist in the direction of the delivery catheter. The delivery catheter is positioned such that the outlet of one of the lumens of the delivery catheter is adjacent to the external surface of the heart (e.g., the external surface of an atrium or a ventricle). A pacing lead is extended through the lumen of the delivery catheter onto the external surface of the heart. The pacing lead may be attached to the external surface of the heart, for example, by screwing the lead into the cardiac tissue. In addition, the pacing lead may be placed deeper into the cardiac tissue, for example in the subendocardial tissue, by screwing the lead further into the tissue. After the lead is placed in the proper position, the delivery catheter is withdrawn from the pericardial space and the body. The guide wire is withdrawn from the pericardial space and the body, and the engagement catheter is withdrawn from the body.

The disclosed embodiments can be used for subendocardial, as well as epicardial, pacing. While the placement of the leads is epicardial, the leads can be configured to have a long screw-like tip that reaches near the subendocardial wall. The tip of the lead can be made to be conducting and stimulatory to provide the pacing to the subendocardial region. In general, the lead length can be selected to pace transmurally at any site through the thickness of the heart wall. Those of skill in the art can decide whether epicardial, subendocardial, or some transmural location stimulation of the muscle is best for the patient in question.

While various embodiments of devices, systems, and methods for accessing the heart tissue have been described in considerable detail herein, the embodiments are merely offered by way of non-limiting examples of the disclosure described herein. Many variations and modifications of the embodiments described herein will be apparent to one of ordinary skill in the art in light of this disclosure. It will therefore be understood by those skilled in the art that various changes and modifications may be made, and equivalents may be substituted for elements thereof without departing from the scope of the disclosure. Indeed, this disclosure is not intended to be exhaustive or to limit the scope of the disclosure. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that the disclosure will include, and this description and the appended claims will encompass, all modifications and changes apparent to those of ordinary skill in the art based on this disclosure.

We claim:

1. A system for use with a vacuum source for engaging a tissue, the system comprising:
   an engagement catheter comprising a proximal end, a distal end, first and second lumens extending between the proximal end and the distal end, an injection channel formed along a length of the engagement catheter, the injection channel being ring-shaped at its distal end and having at its distal end at least one opening for administering a substance to a targeted tissue, and a skirt operatively connected to the distal end, the skirt comprising a proximal end having a circumference substantially similar to an outer circumference of the engagement catheter, the skirt further comprising a distal end having a circumference larger than the outer circumference of the engagement catheter;
   a delivery catheter comprising a proximal end, a distal end, and a hollow tube extending between the proximal end and the distal end, the delivery catheter configured such that the hollow tube is capable of insertion into the second lumen of the engagement catheter;
   a needle located at the distal end of the delivery catheter; and
   a vacuum port located at the proximal end of the engagement catheter, the vacuum port being operatively connected to the first lumen of the engagement catheter and capable of operative connection to a vacuum source;
   wherein the first lumen of the engagement catheter includes a suction port located at or near the distal end of the engagement catheter, the suction port configured to allow the distal end of the skirt to removably engage a surface of a bodily tissue such that the skirt is capable of forming a reversible seal with the surface of the tissue when a vacuum source is operatively attached to the vacuum port.

2. The system of claim 1, wherein the system is capable of enlarging a pericardial space between the bodily tissue and a pericardial sac that surrounds a heart by retracting the targeted tissue away from the pericardial sac.

3. The system of claim 1, wherein the tissue engaged by the system is a heart.

4. The system of claim 3, wherein the system is capable of enlarging a pericardial space between the heart and a pericardial sac when the skirt is attached to an interior wall of the heart.

5. The system of claim 1, wherein the skirt comprises a deformable configuration, and wherein the deformable configuration of the skirt is capable of expanding to an expanded configuration.

6. The system of claim 1, further comprising a sleeve comprising a proximal end, a distal end, and a lumen extending between the proximal end and the distal end, wherein the sleeve is positioned around the engagement catheter, wherein the sleeve slidingly engages the engagement catheter.

7. The system of claim 6, wherein the sleeve may be positioned at the distal end of the engagement catheter, and wherein the sleeve at least partially surrounds the skirt.

8. The system of claim 7, wherein the deformable configuration of the skirt is collapsed when at least partially surrounded by the sleeve.

9. The system of claim 6, wherein the sleeve is positioned along the engagement catheter so not to surround the skirt, wherein the skirt is capable of expanding to an expanded configuration.

10. The system of claim 1, wherein the needle is positioned to be capable of piercing the targeted tissue when the hollow tube is inserted into the second lumen and the suction port is attached to the targeted tissue, such that, when the targeted tissue is pierced, access to the pericardial space is achieved.

11. The system of claim 2, further comprising a guide wire for insertion into the pericardial space, wherein the needle comprises a hollow needle in communication with the hollow tube, and wherein the guide wire is capable of insertion through the hollow tube and the hollow needle into the pericardial space.

12. The system of claim 1, wherein the engagement catheter the injection channel is in fluid communication with the second lumen of the engagement catheter.

13. The system of claim 1, wherein the substance comprises an adhesive.

14. The system of claim 1, wherein the injection channel is capable of operable attachment to an external fluid source at the proximal end of the injection channel, such that fluid from the external fluid source can flow through the injection channel to the targeted tissue when the external fluid source is operatively attached to the injection channel.

15. The system of claim 1, wherein the needle comprises a needle wire for piercing the targeted tissue.

16. The system of claim 1, wherein the needle comprises a pressure tip needle.

17. The system of claim 1, wherein the engagement catheter comprises a curvature along a length of the engagement catheter.

18. The system of claim 17, wherein the curvature of the engagement catheter forms an angle that is approximately forty-five degrees.

19. The system of claim 17, wherein the curvature of the engagement catheter forms an angle that is approximately ninety degrees, so that a portion of the engagement catheter is approximately perpendicular to another portion of the engagement catheter.

20. The system of claim 17, wherein the curvature of the engagement catheter forms an angle so that a portion of the engagement catheter is approximately parallel to another portion of the engagement catheter.

21. An engagement catheter for use with a vacuum source for engaging a tissue, the engagement catheter comprising:

an elongated tube comprising a proximal end, a distal end, an outer wall positioned circumferentially along the length of the tube, and an inner wall positioned circumferentially along the length of the tube, wherein the outer wall and the inner wall form at least one suction channel along the length of the tube between the outer wall and the inner wall, the elongated tube further defining a delivery catheter lumen configured to receive a delivery catheter and an injection channel formed along a length of the elongated tube, the injection channel being ring-shaped at its distal end and having at its distal end at least one opening for administering a substance to a targeted tissue;

a skirt operatively connected to the distal end of the tube, the skirt comprising a proximal end having a circumference substantially similar to an outer circumference of the tube, the skirt further comprising a distal end having a circumference larger than the circumference of the tube;

a vacuum port in communication with the proximal end of the tube, the vacuum port being operatively connected to the at least one suction channel and capable of operative connection to the vacuum source; and a suction port in communication with the at least one suction channel at the distal end of the tube, the suction port configured to allow the distal end of the skirt to removably engage a surface of a bodily tissue such that the skirt is capable of forming a reversible seal with the surface of the tissue when a vacuum source is operatively attached to the vacuum port.

22. The engagement catheter of claim 21, wherein the skirt comprises a deformable configuration, and wherein the deformable configuration of the skirt is capable of expanding to an expanded configuration.

23. The engagement catheter of claim 22, wherein the expanded configuration is a frusto-conical configuration.

24. The engagement catheter of claim 22, wherein the expanded configuration is a an irregular frusto-conical configuration.

25. The engagement catheter of claim 22, wherein the skirt has a collapsed configuration when the skirt is at least partially surrounded by a sleeve, and wherein the skirt has an expanded configuration when the skirt is not surrounded by the sleeve.

26. The engagement catheter of claim 21, wherein the skirt is capable of enlarging a pericardial space between a heart and a pericardial sac when the skirt is attached to an interior wall of the heart.

27. The engagement catheter of claim 21, further comprising at least one internal lumen support positioned within the at least one suction channel and attached to the outer wall and the inner wall, the at least one internal lumen support extending from the distal end of the tube along at least a substantial portion of the length of the tube.

28. The engagement catheter of claim 27, wherein the at least one internal lumen support comprises two internal lumen supports, and the at least one suction channel comprises two suction channels.

29. The engagement catheter of claim 21, wherein the injection channel is capable of operable attachment to an external fluid source at the proximal end of the injection channel, such that fluid from the external fluid source can flow through the injection channel to the targeted tissue when the external fluid source is operatively attached to the injection channel.

30. A method of engaging a tissue, the method comprising the steps of:

providing a system, comprising:

an engagement catheter comprising a proximal end, a distal end, first and second lumens extending between the proximal end and the distal end, an injection channel formed along a length of the engagement catheter, the injection channel being ring-shaped at its distal end and having at its distal end at least one opening for administering a substance to a targeted tissue, and a skirt operatively connected to the distal end, the skirt comprising a proximal end having a circumference substantially similar to an outer circumference of the engagement catheter, the skirt further comprising a distal end having a circumference larger than the outer circumference of the engagement catheter;

a delivery catheter comprising a proximal end, a distal end, and a hollow tube extending between the proximal end and the distal end, the delivery catheter configured such that the hollow tube is capable of insertion into the second lumen of the engagement catheter;

a needle located at the distal end of the delivery catheter; and a vacuum port located at the proximal end of the engagement catheter, the vacuum port being operatively connected to the first lumen of the engagement catheter and capable of operative connection to the vacuum source;

wherein the first lumen of the engagement catheter includes a suction port located at or near the distal end of the engagement catheter, the suction port configured to allow the distal end of the skirt to removably engage a surface of a targeted tissue such that the skirt is capable of forming a reversible seal with the surface of the targeted tissue when a vacuum source is operatively attached to the vacuum port; and inserting the engagement catheter into a body such that the distal end of the engagement catheter is positioned at or near the targeted tissue.

31. The method of claim 30, wherein the system is capable of enlarging a pericardial space between the targeted tissue and a pericardial sac that surrounds a heart by retracting the targeted tissue away from the pericardial sac.

32. The method of claim 31, wherein the step of inserting the engagement catheter into a body comprises the insertion of the engagement catheter such that the distal end of the engagement catheter is positioned inside the heart and the skirt is in contact with the targeted tissue on the interior of a wall of the heart.

33. The method of claim 32, further comprising the step of operatively connecting a vacuum source to the vacuum port such that the skirt is reversibly attached to the targeted tissue on the interior of a wall of the heart.

34. The method of claim 33, further comprising the step of inserting the delivery catheter into the second lumen of the engagement catheter.

35. The method of claim 34, further comprising the step of piercing the targeted tissue on the interior of a wall of the heart with the needle.

36. The method of claim 35, further comprising the step of administering a substance into the pericardial space.

37. The method of claim 35, further comprising the steps of withdrawing the needle from the targeted tissue and administering a substance to the targeted tissue after withdrawal of the needle.

38. The method of claim 37, wherein the substance comprises an adhesive for sealing a puncture wound in the targeted tissue.

39. The method of claim 30, wherein the targeted tissue comprises a portion of an atrial wall.

40. The method of claim 30, wherein the targeted tissue comprises a portion of an atrial appendage.

41. The method of claim 35, further comprising the step of accessing the pericardial space by inserting a guide wire through the wall of the heart into the pericardial space.

* * * * *